(12) United States Patent
Yates et al.

(10) Patent No.: US 9,554,854 B2
(45) Date of Patent: Jan. 31, 2017

(54) DETECTING SHORT CIRCUITS IN ELECTROSURGICAL MEDICAL DEVICES

(71) Applicant: Ethicon Endo-Surgery, Inc., Cincinnati, OH (US)

(72) Inventors: David C. Yates, West Chester, OH (US); Eitan T. Wiener, Cincinnati, OH (US); Robert A. Kemerling, Mason, OH (US); Benjamin J. Danziger, Cincinnati, OH (US); Gavin M. Monson, Oxford, OH (US)

(73) Assignee: Ethicon Endo-Surgery, LLC, Guaynabo, PR (US)

( * ) Notice: Subject to any disclaimer, the term of this patent is extended or adjusted under 35 U.S.C. 154(b) by 267 days.

(21) Appl. No.: 14/218,558

(22) Filed: Mar. 18, 2014

(65) Prior Publication Data

US 2015/0265347 A1  Sep. 24, 2015

(51) Int. Cl.
  *A61B 18/12* (2006.01)
  *A61B 18/18* (2006.01)

(52) U.S. Cl.
  CPC ........... *A61B 18/18* (2013.01); *A61B 18/1206* (2013.01)

(58) Field of Classification Search
  CPC ..................... A61B 18/1206; A61B 18/18
  See application file for complete search history.

(56) References Cited

U.S. PATENT DOCUMENTS

| | | | |
|---|---|---|---|
| 2,366,274 A | 1/1945 | Luth et al. | |
| 2,458,152 A | 1/1949 | Eakins | |
| 2,510,693 A | 6/1950 | Green | |
| 2,867,039 A | 1/1959 | Zach | |
| 3,166,971 A | 1/1965 | Stoecker | |
| 3,525,912 A | 8/1970 | Wallin | |
| 3,580,841 A | 5/1971 | Cadotte et al. | |
| 3,703,651 A | 11/1972 | Blowers | |
| 3,777,760 A | 12/1973 | Essner | |

(Continued)

FOREIGN PATENT DOCUMENTS

| | | |
|---|---|---|
| DE | 4300307 A1 | 7/1994 |
| DE | 19608716 C1 | 4/1997 |

(Continued)

OTHER PUBLICATIONS

Douglas, S.C. "Introduction to Adaptive Filter". Digital Signal Processing Handbook. Ed. Vijay K. Madisetti and Douglas B. Williams. Boca Raton: CRC Press LLC, 1999.

(Continued)

*Primary Examiner* — Daniel Fowler

(57) ABSTRACT

Various embodiments are directed to an electrosurgical systems and methods for providing an electrosurgical signal to a patient. An electrosurgical signal defining a plurality of pulses may be provided to first and second electrodes. A first reading may be received indicating an impedance between the first and second electrodes taken at a first point of a first pulse of the electrosurgical signal. A second reading may indicate the impedance a first point of a second pulse of the electrosurgical signal, where the first point of the first pulse and the first point of the second pulse are at equivalent positions within the first and second pulses. Based on a comparison of the first reading and the second reading, a short circuit may be determined and a signal indicating the short circuit may be generated.

9 Claims, 26 Drawing Sheets

(56) References Cited

U.S. PATENT DOCUMENTS

| | | |
|---|---|---|
| 4,005,714 A | 2/1977 | Hiltebrandt |
| 4,034,762 A | 7/1977 | Cosens et al. |
| 4,058,126 A | 11/1977 | Leveen |
| 4,203,430 A | 5/1980 | Takahashi |
| 4,220,154 A | 9/1980 | Semm |
| 4,237,441 A | 12/1980 | van Konynenburg et al. |
| 4,281,785 A | 8/1981 | Brooks |
| 4,304,987 A | 12/1981 | van Konynenburg |
| 4,463,759 A | 8/1984 | Garito et al. |
| 4,492,231 A | 1/1985 | Auth |
| 4,535,773 A | 8/1985 | Yoon |
| 4,545,926 A | 10/1985 | Fouts, Jr. et al. |
| 4,550,870 A | 11/1985 | Krumme et al. |
| 4,582,236 A | 4/1986 | Hirose |
| 4,617,927 A | 10/1986 | Manes |
| 4,735,603 A | 4/1988 | Goodson et al. |
| 4,761,871 A | 8/1988 | O'Connor et al. |
| 4,830,462 A | 5/1989 | Karny et al. |
| 4,849,133 A | 7/1989 | Yoshida et al. |
| 4,860,745 A | 8/1989 | Farin et al. |
| 4,878,493 A | 11/1989 | Pasternak et al. |
| 4,880,015 A | 11/1989 | Nierman |
| 4,910,389 A | 3/1990 | Sherman et al. |
| 4,920,978 A | 5/1990 | Colvin |
| 4,936,842 A | 6/1990 | D'Amelio et al. |
| 5,020,514 A | 6/1991 | Heckele |
| 5,061,269 A | 10/1991 | Muller |
| 5,099,840 A | 3/1992 | Goble et al. |
| 5,104,025 A | 4/1992 | Main et al. |
| 5,106,538 A | 4/1992 | Barma et al. |
| 5,108,383 A | 4/1992 | White |
| 5,156,633 A | 10/1992 | Smith |
| 5,160,334 A | 11/1992 | Billings et al. |
| 5,190,541 A | 3/1993 | Abele et al. |
| 5,196,007 A | 3/1993 | Ellman et al. |
| 5,205,459 A | 4/1993 | Brinkerhoff et al. |
| 5,217,460 A | 6/1993 | Knoepfler |
| 5,234,428 A | 8/1993 | Kaufman |
| 5,258,006 A | 11/1993 | Rydell et al. |
| 5,285,945 A | 2/1994 | Brinkerhoff et al. |
| 5,290,286 A | 3/1994 | Parins |
| 5,309,927 A | 5/1994 | Welch |
| 5,312,023 A | 5/1994 | Green et al. |
| 5,318,563 A * | 6/1994 | Malis ............... A61B 18/12 606/34 |
| 5,318,564 A | 6/1994 | Eggers |
| 5,318,589 A | 6/1994 | Lichtman |
| 5,326,013 A | 7/1994 | Green et al. |
| 5,330,471 A | 7/1994 | Eggers |
| 5,330,502 A | 7/1994 | Hassler et al. |
| 5,339,723 A | 8/1994 | Huitema |
| 5,342,359 A | 8/1994 | Rydell |
| 5,361,583 A | 11/1994 | Huitema |
| 5,383,874 A | 1/1995 | Jackson et al. |
| 5,387,207 A | 2/1995 | Dyer et al. |
| 5,389,098 A | 2/1995 | Tsuruta et al. |
| 5,395,312 A | 3/1995 | Desai |
| 5,395,363 A | 3/1995 | Billings et al. |
| 5,395,364 A | 3/1995 | Anderhub et al. |
| 5,396,266 A | 3/1995 | Brimhall |
| 5,396,900 A | 3/1995 | Slater et al. |
| 5,403,312 A | 4/1995 | Yates et al. |
| 5,417,709 A | 5/1995 | Slater |
| 5,428,504 A | 6/1995 | Bhatla |
| 5,429,131 A | 7/1995 | Scheinman et al. |
| 5,443,463 A | 8/1995 | Stern et al. |
| 5,445,638 A | 8/1995 | Rydell et al. |
| 5,451,227 A | 9/1995 | Michaelson |
| 5,456,684 A | 10/1995 | Schmidt et al. |
| 5,458,598 A | 10/1995 | Feinberg et al. |
| 5,465,895 A | 11/1995 | Knodel et al. |
| 5,472,443 A | 12/1995 | Cordis et al. |
| 5,476,479 A | 12/1995 | Green et al. |
| 5,478,003 A | 12/1995 | Green et al. |
| 5,480,409 A | 1/1996 | Riza |
| 5,484,436 A | 1/1996 | Eggers et al. |
| 5,486,189 A | 1/1996 | Mudry et al. |
| 5,496,317 A | 3/1996 | Goble et al. |
| 5,504,650 A | 4/1996 | Katsui et al. |
| 5,509,922 A | 4/1996 | Aranyi et al. |
| 5,511,556 A | 4/1996 | DeSantis |
| 5,520,704 A | 5/1996 | Castro et al. |
| 5,522,839 A | 6/1996 | Pilling |
| 5,531,744 A | 7/1996 | Nardella et al. |
| 5,540,681 A | 7/1996 | Strul et al. |
| 5,542,916 A | 8/1996 | Hirsch et al. |
| 5,558,671 A * | 9/1996 | Yates ............... A61B 17/07207 606/34 |
| 5,563,179 A | 10/1996 | Stone et al. |
| 5,569,164 A | 10/1996 | Lurz |
| 5,571,121 A | 11/1996 | Heifetz |
| 5,573,534 A | 11/1996 | Stone |
| 5,584,830 A | 12/1996 | Ladd et al. |
| 5,599,350 A | 2/1997 | Schulze et al. |
| 5,607,450 A | 3/1997 | Zvenyatsky et al. |
| 5,611,813 A | 3/1997 | Lichtman |
| 5,618,307 A | 4/1997 | Donlon et al. |
| 5,624,452 A | 4/1997 | Yates |
| 5,632,432 A | 5/1997 | Schulze et al. |
| 5,647,871 A | 7/1997 | Levine et al. |
| 5,658,281 A | 8/1997 | Heard |
| 5,662,667 A | 9/1997 | Knodel |
| 5,665,085 A | 9/1997 | Nardella |
| 5,665,100 A | 9/1997 | Yoon |
| 5,674,219 A | 10/1997 | Monson et al. |
| 5,674,220 A | 10/1997 | Fox et al. |
| 5,688,270 A | 11/1997 | Yates et al. |
| 5,693,051 A | 12/1997 | Schulze et al. |
| 5,709,680 A | 1/1998 | Yates et al. |
| 5,711,472 A | 1/1998 | Bryan |
| 5,713,896 A | 2/1998 | Nardella |
| 5,716,366 A | 2/1998 | Yates |
| 5,720,742 A | 2/1998 | Zacharias |
| 5,720,744 A | 2/1998 | Eggleston et al. |
| 5,735,848 A | 4/1998 | Yates et al. |
| 5,743,906 A | 4/1998 | Parins et al. |
| 5,752,973 A | 5/1998 | Kieturakis |
| 5,755,717 A | 5/1998 | Yates et al. |
| 5,762,255 A | 6/1998 | Chrisman et al. |
| 5,779,701 A | 7/1998 | McBrayer et al. |
| 5,782,834 A | 7/1998 | Lucey et al. |
| 5,792,135 A | 8/1998 | Madhani et al. |
| 5,792,138 A | 8/1998 | Shipp |
| 5,796,188 A | 8/1998 | Bays |
| 5,797,941 A | 8/1998 | Schulze et al. |
| 5,800,432 A | 9/1998 | Swanson |
| 5,800,449 A | 9/1998 | Wales |
| 5,805,140 A | 9/1998 | Rosenberg et al. |
| 5,807,393 A | 9/1998 | Williamson, IV et al. |
| 5,810,811 A | 9/1998 | Yates et al. |
| 5,817,033 A | 10/1998 | DeSantis et al. |
| 5,817,084 A | 10/1998 | Jensen |
| 5,817,093 A | 10/1998 | Williamson, IV et al. |
| 5,827,323 A | 10/1998 | Klieman |
| 5,836,909 A | 11/1998 | Cosmescu |
| 5,836,943 A * | 11/1998 | Miller, III ......... A61B 18/1206 606/34 |
| 5,836,990 A * | 11/1998 | Li ..................... A61N 1/08 607/28 |
| 5,853,412 A | 12/1998 | Mayenberger |
| 5,876,401 A | 3/1999 | Schulze et al. |
| 5,878,193 A | 3/1999 | Wang et al. |
| 5,880,668 A | 3/1999 | Hall |
| 5,891,142 A | 4/1999 | Eggers et al. |
| 5,906,625 A | 5/1999 | Bito et al. |
| 5,910,129 A * | 6/1999 | Koblish ............. A61B 18/1492 604/159 |
| 5,921,956 A | 7/1999 | Grinberg et al. |
| 5,929,846 A | 7/1999 | Rosenberg et al. |
| 5,984,938 A | 11/1999 | Yoon |
| 6,003,517 A | 12/1999 | Sheffield et al. |
| 6,013,052 A | 1/2000 | Durman et al. |
| 6,024,741 A | 2/2000 | Williamson, IV et al. |
| 6,024,744 A | 2/2000 | Kese et al. |

(56) References Cited

U.S. PATENT DOCUMENTS

| | | | |
|---|---|---|---|
| 6,033,399 A | 3/2000 | Gines | |
| 6,039,734 A | 3/2000 | Goble | |
| 6,050,996 A | 4/2000 | Schmaltz et al. | |
| 6,063,098 A | 5/2000 | Houser et al. | |
| 6,068,629 A | 5/2000 | Haissaguerre et al. | |
| 6,074,389 A | 6/2000 | Levine et al. | |
| 6,091,995 A | 7/2000 | Ingle et al. | |
| 6,099,483 A | 8/2000 | Palmer et al. | |
| 6,099,550 A | 8/2000 | Yoon | |
| H1904 H | 10/2000 | Yates et al. | |
| 6,132,368 A | 10/2000 | Cooper | |
| 6,144,402 A | 11/2000 | Norsworthy et al. | |
| 6,152,923 A | 11/2000 | Ryan | |
| 6,154,198 A | 11/2000 | Rosenberg | |
| 6,162,208 A | 12/2000 | Hipps | |
| 6,174,309 B1 | 1/2001 | Wrublewski et al. | |
| 6,176,857 B1 | 1/2001 | Ashley | |
| 6,190,386 B1 | 2/2001 | Rydell | |
| 6,206,876 B1 | 3/2001 | Levine et al. | |
| 6,228,080 B1 | 5/2001 | Gines | |
| 6,231,565 B1 | 5/2001 | Tovey et al. | |
| 6,259,230 B1 | 7/2001 | Chou | |
| 6,277,117 B1 | 8/2001 | Tetzlaff et al. | |
| 6,292,700 B1 | 9/2001 | Morrison et al. | |
| 6,325,799 B1 | 12/2001 | Goble | |
| 6,340,878 B1 | 1/2002 | Oglesbee | |
| 6,364,888 B1 | 4/2002 | Niemeyer et al. | |
| 6,387,109 B1 | 5/2002 | Davison et al. | |
| 6,391,026 B1 | 5/2002 | Hung et al. | |
| 6,398,779 B1 | 6/2002 | Buysse et al. | |
| H2037 H | 7/2002 | Yates et al. | |
| 6,419,675 B1 | 7/2002 | Gallo, Sr. | |
| 6,430,446 B1 | 8/2002 | Knowlton | |
| 6,443,968 B1 | 9/2002 | Holthaus et al. | |
| 6,458,128 B1 | 10/2002 | Schulze | |
| 6,464,689 B1 * | 10/2002 | Qin | A61B 18/1485 606/1 |
| 6,464,702 B2 | 10/2002 | Schulze et al. | |
| 6,480,796 B2 | 11/2002 | Wiener | |
| 6,491,690 B1 | 12/2002 | Goble et al. | |
| 6,500,112 B1 | 12/2002 | Khouri | |
| 6,500,176 B1 | 12/2002 | Truckai et al. | |
| 6,503,248 B1 | 1/2003 | Levine | |
| 6,511,480 B1 | 1/2003 | Tetzlaff et al. | |
| 6,514,252 B2 | 2/2003 | Nezhat et al. | |
| 6,517,565 B1 | 2/2003 | Whitman et al. | |
| 6,531,846 B1 | 3/2003 | Smith | |
| 6,533,784 B2 | 3/2003 | Truckai et al. | |
| 6,537,272 B2 | 3/2003 | Christopherson et al. | |
| 6,537,291 B2 | 3/2003 | Friedman et al. | |
| 6,551,309 B1 | 4/2003 | LePivert | |
| 6,554,829 B2 | 4/2003 | Schulze et al. | |
| 6,558,376 B2 | 5/2003 | Bishop | |
| 6,562,037 B2 | 5/2003 | Paton et al. | |
| 6,572,639 B1 | 6/2003 | Ingle et al. | |
| 6,575,969 B1 | 6/2003 | Rittman, III et al. | |
| 6,582,451 B1 | 6/2003 | Marucci et al. | |
| 6,584,360 B2 | 6/2003 | Francischelli et al. | |
| 6,585,735 B1 | 7/2003 | Frazier et al. | |
| 6,589,200 B1 | 7/2003 | Schwemberger et al. | |
| 6,602,252 B2 | 8/2003 | Mollenauer | |
| 6,619,529 B2 | 9/2003 | Green et al. | |
| 6,620,161 B2 | 9/2003 | Schulze et al. | |
| 6,622,731 B2 | 9/2003 | Daniel et al. | |
| 6,623,482 B2 | 9/2003 | Pendekanti et al. | |
| 6,635,057 B2 | 10/2003 | Harano et al. | |
| 6,644,532 B2 | 11/2003 | Green et al. | |
| 6,651,669 B1 | 11/2003 | Burnside | |
| 6,656,177 B2 | 12/2003 | Truckai et al. | |
| 6,656,198 B2 | 12/2003 | Tsonton et al. | |
| 6,662,127 B2 | 12/2003 | Wiener et al. | |
| 6,673,248 B2 | 1/2004 | Chowdhury | |
| 6,679,882 B1 | 1/2004 | Kornerup | |
| 6,695,840 B2 | 2/2004 | Schulze | |
| 6,722,552 B2 | 4/2004 | Fenton, Jr. | |
| 6,746,443 B1 | 6/2004 | Morley et al. | |
| 6,752,815 B2 | 6/2004 | Beaupre | |
| 6,770,072 B1 | 8/2004 | Truckai et al. | |
| 6,773,409 B2 | 8/2004 | Truckai et al. | |
| 6,773,435 B2 | 8/2004 | Schulze et al. | |
| 6,775,575 B2 | 8/2004 | Bommannan et al. | |
| 6,783,524 B2 | 8/2004 | Anderson et al. | |
| 6,789,939 B2 | 9/2004 | Schrödinger et al. | |
| 6,796,981 B2 | 9/2004 | Wham et al. | |
| 6,800,085 B2 | 10/2004 | Selmon et al. | |
| 6,802,843 B2 | 10/2004 | Truckai et al. | |
| 6,811,842 B1 | 11/2004 | Ehrnsperger et al. | |
| 6,821,273 B2 | 11/2004 | Mollenauer | |
| 6,835,199 B2 | 12/2004 | McGuckin, Jr. et al. | |
| 6,840,938 B1 | 1/2005 | Morley et al. | |
| 6,860,880 B2 | 3/2005 | Treat et al. | |
| 6,877,647 B2 | 4/2005 | Green et al. | |
| 6,905,497 B2 | 6/2005 | Truckai et al. | |
| 6,908,463 B2 | 6/2005 | Treat et al. | |
| 6,913,579 B2 | 7/2005 | Truckai et al. | |
| 6,926,716 B2 | 8/2005 | Baker et al. | |
| 6,929,622 B2 | 8/2005 | Chian | |
| 6,929,644 B2 | 8/2005 | Truckai et al. | |
| 6,953,461 B2 | 10/2005 | McClurken et al. | |
| 6,977,495 B2 | 12/2005 | Donofrio | |
| 6,994,709 B2 | 2/2006 | Iida | |
| 7,000,818 B2 | 2/2006 | Shelton, IV et al. | |
| 7,011,657 B2 | 3/2006 | Truckai et al. | |
| 7,041,102 B2 | 5/2006 | Truckai et al. | |
| 7,052,496 B2 | 5/2006 | Yamauchi | |
| 7,055,731 B2 | 6/2006 | Shelton, IV et al. | |
| 7,063,699 B2 | 6/2006 | Hess et al. | |
| 7,066,936 B2 | 6/2006 | Ryan | |
| 7,070,597 B2 | 7/2006 | Truckai et al. | |
| 7,077,853 B2 | 7/2006 | Kramer et al. | |
| 7,083,618 B2 | 8/2006 | Couture et al. | |
| 7,083,619 B2 | 8/2006 | Truckai et al. | |
| 7,087,054 B2 | 8/2006 | Truckai et al. | |
| 7,094,235 B2 | 8/2006 | Francischelli et al. | |
| 7,101,371 B2 | 9/2006 | Dycus et al. | |
| 7,101,372 B2 | 9/2006 | Dycus et al. | |
| 7,101,373 B2 | 9/2006 | Dycus et al. | |
| 7,112,201 B2 | 9/2006 | Truckai et al. | |
| 7,118,570 B2 | 10/2006 | Tetzlaff et al. | |
| 7,125,409 B2 | 10/2006 | Truckai et al. | |
| 7,131,970 B2 | 11/2006 | Moses et al. | |
| 7,137,980 B2 | 11/2006 | Buysse et al. | |
| 7,143,925 B2 | 12/2006 | Shelton, IV et al. | |
| 7,147,138 B2 | 12/2006 | Shelton, IV | |
| 7,156,846 B2 | 1/2007 | Dycus et al. | |
| 7,160,296 B2 | 1/2007 | Pearson et al. | |
| 7,169,146 B2 | 1/2007 | Truckai et al. | |
| 7,169,156 B2 | 1/2007 | Hart | |
| 7,179,271 B2 | 2/2007 | Friedman et al. | |
| 7,186,253 B2 | 3/2007 | Truckai et al. | |
| 7,189,233 B2 | 3/2007 | Truckai et al. | |
| 7,195,631 B2 | 3/2007 | Dumbauld | |
| 7,207,471 B2 | 4/2007 | Heinrich et al. | |
| 7,220,951 B2 | 5/2007 | Truckai et al. | |
| 7,225,964 B2 | 6/2007 | Mastri et al. | |
| 7,226,448 B2 | 6/2007 | Bertolero et al. | |
| 7,232,440 B2 | 6/2007 | Dumbauld et al. | |
| 7,235,073 B2 | 6/2007 | Levine et al. | |
| 7,241,294 B2 | 7/2007 | Reschke | |
| 7,251,531 B2 | 7/2007 | Mosher et al. | |
| 7,252,667 B2 | 8/2007 | Moses et al. | |
| 7,267,677 B2 | 9/2007 | Johnson et al. | |
| 7,267,685 B2 | 9/2007 | Butaric et al. | |
| 7,273,483 B2 | 9/2007 | Wiener et al. | |
| 7,287,682 B1 | 10/2007 | Ezzat et al. | |
| 7,300,450 B2 | 11/2007 | Vleugels et al. | |
| 7,303,557 B2 | 12/2007 | Wham et al. | |
| 7,307,313 B2 | 12/2007 | Ohyanagi et al. | |
| 7,309,849 B2 | 12/2007 | Truckai et al. | |
| 7,311,709 B2 | 12/2007 | Truckai et al. | |
| 7,329,257 B2 | 2/2008 | Kanehira et al. | |
| 7,354,440 B2 | 4/2008 | Truckai et al. | |
| 7,357,287 B2 | 4/2008 | Shelton, IV et al. | |
| 7,364,577 B2 | 4/2008 | Wham et al. | |

(56) References Cited

U.S. PATENT DOCUMENTS

| | | |
|---|---|---|
| 7,367,976 B2 | 5/2008 | Lawes et al. |
| 7,371,227 B2 | 5/2008 | Zeiner |
| RE40,388 E | 6/2008 | Gines |
| 7,381,209 B2 | 6/2008 | Truckai et al. |
| 7,384,420 B2 | 6/2008 | Dycus et al. |
| 7,396,356 B2 | 7/2008 | Mollenauer |
| 7,403,224 B2 | 7/2008 | Fuller et al. |
| 7,404,508 B2 | 7/2008 | Smith et al. |
| 7,407,077 B2 | 8/2008 | Ortiz et al. |
| 7,416,101 B2 | 8/2008 | Shelton, IV et al. |
| 7,422,139 B2 | 9/2008 | Shelton, IV et al. |
| 7,435,582 B2 | 10/2008 | Zimmermann et al. |
| 7,441,684 B2 | 10/2008 | Shelton, IV et al. |
| 7,442,193 B2 | 10/2008 | Shields et al. |
| 7,445,621 B2 | 11/2008 | Dumbauld et al. |
| 7,464,846 B2 | 12/2008 | Shelton, IV et al. |
| 7,473,253 B2 | 1/2009 | Dycus et al. |
| 7,488,319 B2 | 2/2009 | Yates |
| 7,491,201 B2 | 2/2009 | Shields et al. |
| 7,494,501 B2 | 2/2009 | Ahlberg et al. |
| 7,498,080 B2 | 3/2009 | Tung et al. |
| 7,506,791 B2 | 3/2009 | Omaits et al. |
| 7,510,107 B2 | 3/2009 | Timm et al. |
| 7,513,025 B2 | 4/2009 | Fischer |
| 7,517,349 B2 | 4/2009 | Truckai et al. |
| 7,524,320 B2 | 4/2009 | Tierney et al. |
| 7,540,872 B2 | 6/2009 | Schechter et al. |
| 7,543,730 B1 | 6/2009 | Marczyk |
| 7,550,216 B2 | 6/2009 | Ofer et al. |
| 7,553,309 B2 | 6/2009 | Buysse et al. |
| 7,559,452 B2 | 7/2009 | Wales et al. |
| 7,582,086 B2 | 9/2009 | Privitera et al. |
| 7,586,289 B2 | 9/2009 | Andruk et al. |
| 7,588,176 B2 | 9/2009 | Timm et al. |
| 7,594,925 B2 | 9/2009 | Danek et al. |
| 7,597,693 B2 | 10/2009 | Garrison |
| 7,604,150 B2 | 10/2009 | Boudreaux |
| 7,621,930 B2 | 11/2009 | Houser |
| 7,628,791 B2 | 12/2009 | Garrison et al. |
| 7,628,792 B2 | 12/2009 | Guerra |
| 7,632,267 B2 | 12/2009 | Dahla |
| 7,632,269 B2 | 12/2009 | Truckai et al. |
| 7,641,653 B2 | 1/2010 | Dalla Betta et al. |
| 7,641,671 B2 | 1/2010 | Crainich |
| 7,644,848 B2 | 1/2010 | Swayze et al. |
| 7,645,277 B2 | 1/2010 | McClurken et al. |
| 7,648,499 B2 | 1/2010 | Orszulak et al. |
| 7,658,311 B2 | 2/2010 | Boudreaux |
| 7,665,647 B2 | 2/2010 | Shelton, IV et al. |
| 7,666,206 B2 | 2/2010 | Taniguchi et al. |
| 7,670,334 B2 | 3/2010 | Hueil et al. |
| 7,691,095 B2 | 4/2010 | Bednarek et al. |
| 7,691,098 B2 | 4/2010 | Wallace et al. |
| 7,703,459 B2 | 4/2010 | Saadat et al. |
| 7,703,653 B2 | 4/2010 | Shah et al. |
| 7,708,751 B2 | 5/2010 | Hughes et al. |
| 7,717,915 B2 | 5/2010 | Miyazawa |
| 7,722,527 B2 | 5/2010 | Bouchier et al. |
| 7,722,607 B2 | 5/2010 | Dumbauld et al. |
| 7,726,537 B2 | 6/2010 | Olson et al. |
| 7,753,904 B2 | 7/2010 | Shelton, IV et al. |
| 7,753,908 B2 | 7/2010 | Swanson |
| 7,762,445 B2 | 7/2010 | Heinrich et al. |
| 7,766,210 B2 | 8/2010 | Shelton, IV et al. |
| 7,766,910 B2 | 8/2010 | Hixson et al. |
| 7,770,775 B2 | 8/2010 | Shelton, IV et al. |
| 7,775,972 B2 | 8/2010 | Brock et al. |
| 7,776,037 B2 | 8/2010 | Odom |
| 7,780,651 B2 | 8/2010 | Madhani et al. |
| 7,780,663 B2 | 8/2010 | Yates et al. |
| 7,784,663 B2 | 8/2010 | Shelton, IV |
| 7,789,883 B2 | 9/2010 | Takashino et al. |
| 7,803,156 B2 | 9/2010 | Eder et al. |
| 7,806,891 B2 | 10/2010 | Nowlin et al. |
| 7,810,693 B2 | 10/2010 | Broehl et al. |
| 7,815,641 B2 | 10/2010 | Dodde et al. |
| 7,819,298 B2 | 10/2010 | Hall et al. |
| 7,819,299 B2 | 10/2010 | Sheltoin, IV et al. |
| 7,819,872 B2 | 10/2010 | Johnson et al. |
| 7,824,401 B2 | 11/2010 | Manzo et al. |
| 7,832,408 B2 | 11/2010 | Shelton, IV et al. |
| 7,832,612 B2 | 11/2010 | Baxter, III et al. |
| 7,845,537 B2 | 12/2010 | Shelton, IV et al. |
| 7,846,159 B2 | 12/2010 | Morrison et al. |
| 7,846,160 B2 | 12/2010 | Payne et al. |
| 7,861,906 B2 | 1/2011 | Doll et al. |
| 7,879,035 B2 | 2/2011 | Garrison et al. |
| 7,879,070 B2 | 2/2011 | Ortiz et al. |
| 7,896,875 B2 | 3/2011 | Heim et al. |
| 7,901,400 B2 | 3/2011 | Wham et al. |
| 7,909,220 B2 | 3/2011 | Viola |
| 7,919,184 B2 | 4/2011 | Mohapatra et al. |
| 7,922,061 B2 | 4/2011 | Shelton, IV et al. |
| 7,922,651 B2 | 4/2011 | Yamada et al. |
| 7,931,649 B2 | 4/2011 | Couture et al. |
| 7,935,114 B2 | 5/2011 | Takashino et al. |
| 7,951,165 B2 | 5/2011 | Golden et al. |
| 7,955,331 B2 | 6/2011 | Truckai et al. |
| 7,963,963 B2 | 6/2011 | Francischelli et al. |
| 7,967,602 B2 | 6/2011 | Lindquist |
| 7,981,113 B2 | 7/2011 | Truckai et al. |
| 7,997,278 B2 | 8/2011 | Utley et al. |
| 8,020,743 B2 | 9/2011 | Shelton, IV |
| 8,038,693 B2 | 10/2011 | Allen |
| 8,056,720 B2 | 11/2011 | Hawkes |
| 8,058,771 B2 | 11/2011 | Giordano et al. |
| 8,061,014 B2 | 11/2011 | Smith et al. |
| 8,070,036 B1 | 12/2011 | Knodel et al. |
| 8,105,323 B2 | 1/2012 | Buysse et al. |
| 8,128,624 B2 | 3/2012 | Couture et al. |
| 8,136,712 B2 | 3/2012 | Zingman |
| 8,141,762 B2 | 3/2012 | Bedi et al. |
| 8,157,145 B2 | 4/2012 | Shelton, IV et al. |
| 8,197,472 B2 | 6/2012 | Lau et al. |
| 8,197,479 B2 | 6/2012 | Olson et al. |
| 8,197,502 B2 | 6/2012 | Smith et al. |
| 8,221,415 B2 | 7/2012 | Francischelli |
| 8,236,020 B2 | 8/2012 | Smith et al. |
| 8,241,235 B2 | 8/2012 | Kahler et al. |
| 8,246,615 B2 | 8/2012 | Behnke |
| 8,246,618 B2 | 8/2012 | Bucciaglia et al. |
| 8,251,994 B2 | 8/2012 | McKenna et al. |
| 8,262,563 B2 | 9/2012 | Bakos et al. |
| 8,267,300 B2 | 9/2012 | Boudreaux |
| 8,277,446 B2 | 10/2012 | Heard |
| 8,277,447 B2 | 10/2012 | Garrison et al. |
| 8,282,669 B2 | 10/2012 | Gerber et al. |
| 8,287,528 B2 | 10/2012 | Wham et al. |
| 8,292,886 B2 | 10/2012 | Kerr et al. |
| 8,298,232 B2 | 10/2012 | Unger |
| 8,303,583 B2 | 11/2012 | Hosier et al. |
| 8,323,310 B2 | 12/2012 | Kingsley |
| 8,333,778 B2 | 12/2012 | Smith et al. |
| 8,333,779 B2 | 12/2012 | Smith et al. |
| 8,334,468 B2 | 12/2012 | Palmer et al. |
| 8,338,726 B2 | 12/2012 | Palmer et al. |
| 8,357,158 B2 | 1/2013 | McKenna et al. |
| 8,372,099 B2 | 2/2013 | Deville et al. |
| 8,372,101 B2 | 2/2013 | Smith et al. |
| 8,377,059 B2 | 2/2013 | Deville et al. |
| 8,377,085 B2 | 2/2013 | Smith et al. |
| 8,397,971 B2 | 3/2013 | Yates et al. |
| 8,403,948 B2 | 3/2013 | Deville et al. |
| 8,403,949 B2 | 3/2013 | Palmer et al. |
| 8,403,950 B2 | 3/2013 | Palmer et al. |
| 8,414,577 B2 | 4/2013 | Boudreaux et al. |
| 8,418,349 B2 | 4/2013 | Smith et al. |
| 8,419,757 B2 | 4/2013 | Smith et al. |
| 8,419,758 B2 | 4/2013 | Smith et al. |
| 8,425,545 B2 | 4/2013 | Smith et al. |
| 8,430,876 B2 | 4/2013 | Kappus et al. |
| 8,435,257 B2 | 5/2013 | Smith et al. |
| 8,439,939 B2 | 5/2013 | Deville et al. |
| 8,444,662 B2 | 5/2013 | Palmer et al. |

(56) References Cited

U.S. PATENT DOCUMENTS

| | | |
|---|---|---|
| 8,444,664 B2 | 5/2013 | Balanev et al. |
| 8,453,906 B2 | 6/2013 | Huang et al. |
| 8,460,288 B2 | 6/2013 | Tamai et al. |
| 8,460,292 B2 | 6/2013 | Truckai et al. |
| 8,480,703 B2 | 7/2013 | Nicholas et al. |
| 8,485,413 B2 | 7/2013 | Scheib et al. |
| 8,486,057 B2 | 7/2013 | Behnke, II |
| 8,496,682 B2 | 7/2013 | Guerra et al. |
| 8,535,311 B2 | 9/2013 | Schall |
| 8,535,340 B2 | 9/2013 | Allen |
| 8,535,341 B2 | 9/2013 | Allen |
| 8,540,128 B2 | 9/2013 | Shelton, IV et al. |
| 8,562,598 B2 | 10/2013 | Falkenstein et al. |
| 8,562,604 B2 | 10/2013 | Nishimura |
| 8,568,390 B2 | 10/2013 | Mueller |
| 8,568,412 B2 | 10/2013 | Brandt et al. |
| 8,569,997 B2 | 10/2013 | Lee |
| 8,574,231 B2 | 11/2013 | Boudreaux et al. |
| 8,591,506 B2 | 11/2013 | Wham et al. |
| D695,407 S | 12/2013 | Price et al. |
| 8,613,383 B2 | 12/2013 | Beckman et al. |
| 8,623,011 B2 | 1/2014 | Spivey |
| 8,623,027 B2 | 1/2014 | Price et al. |
| 8,623,044 B2 | 1/2014 | Timm et al. |
| 8,628,529 B2 | 1/2014 | Aldridge et al. |
| 8,632,461 B2 | 1/2014 | Glossop |
| 8,647,350 B2 | 2/2014 | Mohan et al. |
| 8,663,220 B2 | 3/2014 | Wiener et al. |
| 8,663,222 B2 | 3/2014 | Anderson et al. |
| 8,684,253 B2 | 4/2014 | Giordano et al. |
| 8,685,020 B2 | 4/2014 | Weizman et al. |
| 8,696,665 B2 | 4/2014 | Hunt et al. |
| 8,702,609 B2 | 4/2014 | Hadjicostis |
| 8,702,704 B2 | 4/2014 | Shelton, IV et al. |
| 8,709,035 B2 | 4/2014 | Johnson et al. |
| 8,715,270 B2 | 5/2014 | Weitzner et al. |
| 8,715,277 B2 | 5/2014 | Weizman |
| 8,734,443 B2 | 5/2014 | Hixson et al. |
| 8,747,238 B2 | 6/2014 | Shelton, IV et al. |
| 8,747,351 B2 | 6/2014 | Schultz |
| 8,747,404 B2 | 6/2014 | Boudreaux et al. |
| 8,752,264 B2 | 6/2014 | Ackley et al. |
| 8,752,749 B2 | 6/2014 | Moore et al. |
| 8,753,338 B2 | 6/2014 | Widenhouse et al. |
| 8,764,747 B2 | 7/2014 | Cummings et al. |
| 8,790,342 B2 | 7/2014 | Stulen et al. |
| 8,795,276 B2 | 8/2014 | Dietz et al. |
| 8,795,327 B2 | 8/2014 | Dietz et al. |
| 8,834,466 B2 | 9/2014 | Cummings et al. |
| 8,834,518 B2 | 9/2014 | Faller et al. |
| 8,845,630 B2 | 9/2014 | Mehta et al. |
| 8,888,776 B2 | 11/2014 | Dietz et al. |
| 8,888,809 B2 | 11/2014 | Davison et al. |
| 8,906,016 B2 | 12/2014 | Boudreaux et al. |
| 8,926,607 B2 | 1/2015 | Norvell et al. |
| 8,926,608 B2 | 1/2015 | Bacher et al. |
| 8,931,682 B2 | 1/2015 | Timm et al. |
| 8,939,974 B2 | 1/2015 | Boudreaux et al. |
| 8,951,248 B2 | 2/2015 | Messerly et al. |
| 8,956,349 B2 | 2/2015 | Aldridge et al. |
| 8,979,843 B2 | 3/2015 | Timm et al. |
| 8,979,844 B2 | 3/2015 | White et al. |
| 8,979,890 B2 | 3/2015 | Boudreaux |
| 8,986,302 B2 | 3/2015 | Aldridge et al. |
| 8,992,422 B2 | 3/2015 | Spivey et al. |
| 9,005,199 B2 | 4/2015 | Beckman et al. |
| 9,011,437 B2 | 4/2015 | Woodruff et al. |
| 9,028,494 B2 | 5/2015 | Shelton, IV et al. |
| 9,028,519 B2 | 5/2015 | Yates et al. |
| 9,044,243 B2 | 6/2015 | Johnson et al. |
| 9,044,256 B2 | 6/2015 | Cadeddu et al. |
| 9,055,961 B2 | 6/2015 | Manzo et al. |
| 9,060,770 B2 | 6/2015 | Shelton, IV et al. |
| 9,072,535 B2 | 7/2015 | Shelton, IV et al. |
| 9,072,536 B2 | 7/2015 | Shelton, IV et al. |
| 9,101,385 B2 | 8/2015 | Shelton, IV et al. |
| 9,119,957 B2 | 9/2015 | Gantz et al. |
| 9,125,662 B2 | 9/2015 | Shelton, IV |
| 9,149,324 B2 | 10/2015 | Huang et al. |
| 9,149,325 B2 | 10/2015 | Worrell et al. |
| 9,179,912 B2 | 11/2015 | Yates et al. |
| 9,192,380 B2 | 11/2015 | (Tarinelli) Racenet et al. |
| 9,192,431 B2 | 11/2015 | Woodruff et al. |
| 9,198,714 B2 | 12/2015 | Worrell et al. |
| 9,204,879 B2 | 12/2015 | Shelton, IV |
| 9,226,751 B2 | 1/2016 | Shelton, IV et al. |
| 9,226,767 B2 | 1/2016 | Stulen et al. |
| 9,237,891 B2 | 1/2016 | Shelton, IV |
| 9,259,265 B2 | 2/2016 | Harris et al. |
| 9,265,926 B2 | 2/2016 | Strobl et al. |
| 9,277,962 B2 | 3/2016 | Koss et al. |
| 9,283,027 B2 | 3/2016 | Monson et al. |
| 9,283,045 B2 | 3/2016 | Rhee et al. |
| 9,295,514 B2 | 3/2016 | Shelton, IV et al. |
| 9,314,292 B2 | 4/2016 | Trees et al. |
| 9,326,788 B2 | 5/2016 | Batross et al. |
| 9,333,025 B2 | 5/2016 | Monson et al. |
| 9,351,754 B2 | 5/2016 | Vakharia et al. |
| 9,375,232 B2 | 6/2016 | Hunt et al. |
| 9,408,660 B2 | 8/2016 | Strobl et al. |
| 2002/0022836 A1 | 2/2002 | Goble et al. |
| 2002/0049551 A1 | 4/2002 | Friedman et al. |
| 2002/0165541 A1 | 11/2002 | Whitman |
| 2003/0014053 A1 | 1/2003 | Nguyen et al. |
| 2003/0105474 A1 | 6/2003 | Bonutti |
| 2003/0114851 A1 | 6/2003 | Truckai et al. |
| 2003/0130693 A1 | 7/2003 | Levin et al. |
| 2003/0139741 A1 | 7/2003 | Goble et al. |
| 2003/0158548 A1 | 8/2003 | Phan et al. |
| 2003/0216722 A1 | 11/2003 | Swanson |
| 2003/0229344 A1 | 12/2003 | Dycus et al. |
| 2004/0019350 A1 | 1/2004 | O'Brien et al. |
| 2004/0054364 A1 | 3/2004 | Aranyi et al. |
| 2004/0092992 A1 | 5/2004 | Adams et al. |
| 2004/0138621 A1 | 7/2004 | Jahns et al. |
| 2004/0167508 A1 | 8/2004 | Wham et al. |
| 2004/0193148 A1 | 9/2004 | Wham et al. |
| 2004/0193150 A1 | 9/2004 | Sharkey et al. |
| 2004/0232196 A1 | 11/2004 | Shelton, IV et al. |
| 2004/0249374 A1 | 12/2004 | Tetzlaff et al. |
| 2004/0260273 A1 | 12/2004 | Wan |
| 2005/0015125 A1 | 1/2005 | Mioduski et al. |
| 2005/0033278 A1 | 2/2005 | McClurken et al. |
| 2005/0085809 A1 | 4/2005 | Mucko et al. |
| 2005/0090817 A1 | 4/2005 | Phan |
| 2005/0103819 A1 | 5/2005 | Racenet et al. |
| 2005/0131390 A1 | 6/2005 | Heinrich et al. |
| 2005/0165429 A1 | 7/2005 | Douglas et al. |
| 2005/0171522 A1 | 8/2005 | Christopherson |
| 2005/0203507 A1 | 9/2005 | Truckai et al. |
| 2005/0256405 A1 | 11/2005 | Makin et al. |
| 2005/0261581 A1 | 11/2005 | Hughes et al. |
| 2005/0267464 A1 | 12/2005 | Truckai et al. |
| 2006/0052778 A1 | 3/2006 | Chapman et al. |
| 2006/0058825 A1 | 3/2006 | Ogura et al. |
| 2006/0064086 A1 | 3/2006 | Odom |
| 2006/0069388 A1 | 3/2006 | Truckai et al. |
| 2006/0159731 A1 | 7/2006 | Shoshan |
| 2006/0270916 A1 | 11/2006 | Skwarek et al. |
| 2006/0293656 A1 | 12/2006 | Shadduck et al. |
| 2007/0027469 A1 | 2/2007 | Smith et al. |
| 2007/0073185 A1 | 3/2007 | Nakao |
| 2007/0073341 A1 | 3/2007 | Smith et al. |
| 2007/0106158 A1 | 5/2007 | Madan et al. |
| 2007/0106317 A1 | 5/2007 | Shelton, IV et al. |
| 2007/0146113 A1 | 6/2007 | Truckai et al. |
| 2007/0173803 A1 | 7/2007 | Wham et al. |
| 2007/0173813 A1 | 7/2007 | Odom |
| 2007/0175949 A1 | 8/2007 | Shelton, IV et al. |
| 2007/0185474 A1 | 8/2007 | Nahen |
| 2007/0191713 A1 | 8/2007 | Eichmann et al. |
| 2007/0191830 A1 | 8/2007 | Cromton, Jr. et al. |
| 2007/0203483 A1 | 8/2007 | Kim et al. |
| 2007/0208312 A1 | 9/2007 | Norton et al. |

(56) References Cited

U.S. PATENT DOCUMENTS

| | | |
|---|---|---|
| 2007/0232920 A1 | 10/2007 | Kowalski et al. |
| 2007/0232926 A1 | 10/2007 | Stulen et al. |
| 2007/0232927 A1 | 10/2007 | Madan et al. |
| 2007/0232928 A1 | 10/2007 | Wiener et al. |
| 2007/0236213 A1 | 10/2007 | Paden et al. |
| 2007/0239025 A1 | 10/2007 | Wiener et al. |
| 2007/0260242 A1 | 11/2007 | Dycus et al. |
| 2007/0265613 A1 | 11/2007 | Edelstein et al. |
| 2008/0015575 A1 | 1/2008 | Odom et al. |
| 2008/0071269 A1 | 3/2008 | Hilario et al. |
| 2008/0114355 A1 | 5/2008 | Whayne et al. |
| 2008/0147058 A1 | 6/2008 | Horrell et al. |
| 2008/0147062 A1 | 6/2008 | Truckai et al. |
| 2008/0167522 A1 | 7/2008 | Giordano et al. |
| 2008/0188755 A1 | 8/2008 | Hart |
| 2008/0188851 A1 | 8/2008 | Truckai et al. |
| 2008/0188912 A1 | 8/2008 | Stone et al. |
| 2008/0214967 A1 | 9/2008 | Aranyi et al. |
| 2008/0221565 A1 | 9/2008 | Eder et al. |
| 2008/0262491 A1 | 10/2008 | Swoyer et al. |
| 2008/0269862 A1 | 10/2008 | Elmouelhi et al. |
| 2008/0281315 A1 | 11/2008 | Gines |
| 2008/0294158 A1 | 11/2008 | Pappone et al. |
| 2008/0300588 A1 | 12/2008 | Groth et al. |
| 2009/0012516 A1 | 1/2009 | Curtis et al. |
| 2009/0048589 A1 | 2/2009 | Takashino et al. |
| 2009/0076506 A1 | 3/2009 | Baker |
| 2009/0076534 A1 | 3/2009 | Shelton, IV et al. |
| 2009/0099582 A1 | 4/2009 | Isaacs et al. |
| 2009/0112229 A1 | 4/2009 | Omori et al. |
| 2009/0125026 A1 | 5/2009 | Rioux et al. |
| 2009/0125027 A1 | 5/2009 | Fischer |
| 2009/0138003 A1 | 5/2009 | Deville et al. |
| 2009/0138006 A1 | 5/2009 | Bales et al. |
| 2009/0182332 A1 | 7/2009 | Long et al. |
| 2009/0206140 A1 | 8/2009 | Scheib et al. |
| 2009/0209979 A1 | 8/2009 | Yates et al. |
| 2009/0248002 A1 | 10/2009 | Takashino et al. |
| 2009/0248021 A1 | 10/2009 | McKenna |
| 2009/0320268 A1 | 12/2009 | Cunningham et al. |
| 2009/0326530 A1 | 12/2009 | Orban, III et al. |
| 2010/0032470 A1 | 2/2010 | Hess et al. |
| 2010/0036370 A1 | 2/2010 | Mirel et al. |
| 2010/0036380 A1 | 2/2010 | Taylor et al. |
| 2010/0076433 A1 | 3/2010 | Taylor et al. |
| 2010/0081863 A1 | 4/2010 | Hess et al. |
| 2010/0081864 A1 | 4/2010 | Hess et al. |
| 2010/0081880 A1 | 4/2010 | Widenhouse et al. |
| 2010/0081881 A1 | 4/2010 | Murray et al. |
| 2010/0081882 A1 | 4/2010 | Hess et al. |
| 2010/0081883 A1 | 4/2010 | Murray et al. |
| 2010/0081995 A1 | 4/2010 | Widenhouse et al. |
| 2010/0094323 A1 | 4/2010 | Isaacs et al. |
| 2010/0168620 A1 | 7/2010 | Klimovitch et al. |
| 2010/0222752 A1 | 9/2010 | Collins, Jr. et al. |
| 2010/0237132 A1 | 9/2010 | Measamer et al. |
| 2010/0264194 A1 | 10/2010 | Huang et al. |
| 2010/0274278 A1 | 10/2010 | Fleenor et al. |
| 2011/0015627 A1 | 1/2011 | DiNardo et al. |
| 2011/0082486 A1 | 4/2011 | Messerly et al. |
| 2011/0087214 A1 | 4/2011 | Giordano et al. |
| 2011/0087215 A1 | 4/2011 | Aldridge et al. |
| 2011/0087216 A1 | 4/2011 | Aldridge et al. |
| 2011/0087217 A1 | 4/2011 | Yates et al. |
| 2011/0087220 A1 | 4/2011 | Felder et al. |
| 2011/0118754 A1 | 5/2011 | Dachs, II et al. |
| 2011/0155781 A1 | 6/2011 | Swensgard et al. |
| 2011/0224668 A1 | 9/2011 | Johnson et al. |
| 2011/0238056 A1* | 9/2011 | Koss ................ A61B 18/1233 606/33 |
| 2011/0276049 A1 | 11/2011 | Gerhardt |
| 2011/0276057 A1 | 11/2011 | Conlon et al. |
| 2011/0284014 A1 | 11/2011 | Cadeddu et al. |
| 2011/0290856 A1 | 12/2011 | Shelton, IV et al. |
| 2011/0292378 A1* | 12/2011 | Brown ................ A61B 18/20 356/73.1 |
| 2011/0295269 A1 | 12/2011 | Swensgard et al. |
| 2011/0295295 A1 | 12/2011 | Shelton, IV et al. |
| 2011/0301605 A1 | 12/2011 | Horner |
| 2011/0306967 A1 | 12/2011 | Payne et al. |
| 2011/0313415 A1 | 12/2011 | Fernandez et al. |
| 2012/0016413 A1 | 1/2012 | Timm et al. |
| 2012/0022519 A1 | 1/2012 | Huang et al. |
| 2012/0022526 A1 | 1/2012 | Aldridge et al. |
| 2012/0078139 A1* | 3/2012 | Aldridge ........ A61B 17/320092 601/2 |
| 2012/0078243 A1 | 3/2012 | Worrell et al. |
| 2012/0078244 A1 | 3/2012 | Worrell et al. |
| 2012/0078247 A1 | 3/2012 | Worrell et al. |
| 2012/0078248 A1 | 3/2012 | Worrell et al. |
| 2012/0083783 A1 | 4/2012 | Davison et al. |
| 2012/0109186 A1 | 5/2012 | Parrott et al. |
| 2012/0116265 A1 | 5/2012 | Houser et al. |
| 2012/0116379 A1 | 5/2012 | Yates et al. |
| 2012/0116380 A1 | 5/2012 | Madan et al. |
| 2012/0116391 A1 | 5/2012 | Houser et al. |
| 2012/0130256 A1 | 5/2012 | Buysse et al. |
| 2012/0136353 A1 | 5/2012 | Romero |
| 2012/0138660 A1 | 6/2012 | Shelton, IV |
| 2012/0150170 A1 | 6/2012 | Buysse et al. |
| 2012/0150192 A1 | 6/2012 | Dachs, II et al. |
| 2012/0172859 A1 | 7/2012 | Condie et al. |
| 2012/0215213 A1* | 8/2012 | Juzkiw ................ A61B 18/14 606/33 |
| 2012/0265196 A1 | 10/2012 | Turner et al. |
| 2013/0023925 A1 | 1/2013 | Mueller |
| 2013/0030433 A1 | 1/2013 | Heard |
| 2013/0079762 A1 | 3/2013 | Twomey et al. |
| 2013/0085496 A1 | 4/2013 | Unger et al. |
| 2013/0103023 A1 | 4/2013 | Monson et al. |
| 2013/0103024 A1 | 4/2013 | Monson et al. |
| 2013/0123776 A1 | 5/2013 | Monson et al. |
| 2013/0158659 A1 | 6/2013 | Bergs et al. |
| 2013/0158660 A1 | 6/2013 | Bergs et al. |
| 2013/0253256 A1 | 9/2013 | Griffith et al. |
| 2013/0253502 A1 | 9/2013 | Aronow et al. |
| 2013/0338661 A1 | 12/2013 | Behnke, II |
| 2014/0001231 A1 | 1/2014 | Shelton, IV et al. |
| 2014/0001234 A1 | 1/2014 | Shelton, IV et al. |
| 2014/0001235 A1 | 1/2014 | Shelton, IV |
| 2014/0001236 A1 | 1/2014 | Shelton, IV et al. |
| 2014/0005640 A1 | 1/2014 | Shelton, IV et al. |
| 2014/0005653 A1 | 1/2014 | Shelton, IV et al. |
| 2014/0005678 A1 | 1/2014 | Shelton, IV et al. |
| 2014/0005680 A1 | 1/2014 | Shelton, IV et al. |
| 2014/0005681 A1 | 1/2014 | Gee et al. |
| 2014/0005693 A1 | 1/2014 | Shelton, IV et al. |
| 2014/0005694 A1 | 1/2014 | Shelton, IV et al. |
| 2014/0005695 A1 | 1/2014 | Shelton, IV |
| 2014/0005701 A1 | 1/2014 | Olson et al. |
| 2014/0005702 A1 | 1/2014 | Timm et al. |
| 2014/0005703 A1 | 1/2014 | Stulen et al. |
| 2014/0005705 A1 | 1/2014 | Weir et al. |
| 2014/0005718 A1 | 1/2014 | Shelton, IV et al. |
| 2014/0014544 A1 | 1/2014 | Bugnard et al. |
| 2014/0094801 A1 | 4/2014 | Boudreaux et al. |
| 2014/0148806 A1 | 5/2014 | Witt et al. |
| 2014/0194915 A1 | 7/2014 | Johnson et al. |
| 2014/0257284 A1 | 9/2014 | Artale |
| 2014/0316408 A1 | 10/2014 | Davison et al. |
| 2014/0330271 A1 | 11/2014 | Dietz et al. |
| 2014/0343550 A1 | 11/2014 | Faller et al. |
| 2015/0018826 A1 | 1/2015 | Boudreaux |
| 2015/0080876 A1 | 3/2015 | Worrell et al. |
| 2015/0080879 A1 | 3/2015 | Trees et al. |
| 2015/0080891 A1 | 3/2015 | Shelton, IV et al. |
| 2015/0133915 A1 | 5/2015 | Strobl et al. |
| 2015/0190189 A1 | 7/2015 | Yates et al. |
| 2015/0196352 A1 | 7/2015 | Beckman et al. |
| 2015/0230853 A1 | 8/2015 | Johnson et al. |
| 2015/0272602 A1 | 10/2015 | Boudreaux et al. |
| 2015/0272657 A1 | 10/2015 | Yates et al. |
| 2015/0272659 A1 | 10/2015 | Boudreaux et al. |

(56) References Cited

U.S. PATENT DOCUMENTS

| | | |
|---|---|---|
| 2015/0272660 A1 | 10/2015 | Boudreaux et al. |
| 2015/0289925 A1 | 10/2015 | Voegele et al. |
| 2015/0297286 A1 | 10/2015 | Boudreaux et al. |
| 2016/0045248 A1 | 2/2016 | Unger et al. |
| 2016/0051315 A1 | 2/2016 | Boudreaux |
| 2016/0051316 A1 | 2/2016 | Boudreaux |
| 2016/0051317 A1 | 2/2016 | Boudreaux |
| 2016/0058492 A1 | 3/2016 | Yates et al. |
| 2016/0074108 A1 | 3/2016 | Woodruff et al. |
| 2016/0128762 A1 | 5/2016 | Harris et al. |
| 2016/0135875 A1 | 5/2016 | Strobl et al. |
| 2016/0157927 A1 | 6/2016 | Corbett et al. |
| 2016/0175024 A1 | 6/2016 | Yates et al. |
| 2016/0175028 A1 | 6/2016 | Trees et al. |
| 2016/0175029 A1 | 6/2016 | Witt et al. |
| 2016/0175030 A1 | 6/2016 | Boudreaux |
| 2016/0175031 A1 | 6/2016 | Boudreaux |
| 2016/0175032 A1 | 6/2016 | Yang |
| 2016/0228171 A1 | 8/2016 | Boudreaux |

FOREIGN PATENT DOCUMENTS

| | | |
|---|---|---|
| DE | 29623113 U1 | 10/1997 |
| DE | 20004812 U1 | 9/2000 |
| DE | 10201569 A1 | 7/2003 |
| EP | 0340803 B1 | 8/1993 |
| EP | 0630612 A1 | 12/1994 |
| EP | 0705571 A1 | 4/1996 |
| EP | 0557806 B1 | 5/1998 |
| EP | 0640317 B1 | 9/1999 |
| EP | 0722696 B1 | 12/2002 |
| EP | 1293172 B1 | 4/2006 |
| EP | 1704824 A1 | 9/2006 |
| EP | 1749479 A1 | 2/2007 |
| EP | 1767157 A1 | 3/2007 |
| EP | 1878399 A1 | 1/2008 |
| EP | 1915953 A1 | 4/2008 |
| EP | 1532933 B1 | 5/2008 |
| EP | 1707143 B1 | 6/2008 |
| EP | 1943957 A2 | 7/2008 |
| EP | 1435852 B1 | 12/2008 |
| EP | 1849424 B1 | 4/2009 |
| EP | 2042117 A1 | 4/2009 |
| EP | 2060238 A1 | 5/2009 |
| EP | 1810625 B1 | 8/2009 |
| EP | 2090238 A1 | 8/2009 |
| EP | 2090256 A2 | 8/2009 |
| EP | 2092905 A1 | 8/2009 |
| EP | 2105104 A2 | 9/2009 |
| EP | 1747761 B1 | 10/2009 |
| EP | 1769766 B1 | 2/2010 |
| EP | 2151204 A1 | 2/2010 |
| EP | 2153791 A1 | 2/2010 |
| EP | 2243439 A1 | 10/2010 |
| EP | 1510178 B1 | 6/2011 |
| EP | 1728475 B1 | 8/2011 |
| EP | 2353518 A1 | 8/2011 |
| EP | 2316359 B1 | 3/2013 |
| EP | 2578172 A2 | 4/2013 |
| EP | 2508143 B1 | 2/2014 |
| GB | 2472216 A | 2/2011 |
| JP | H 08-229050 A | 9/1996 |
| JP | 2008-018226 A | 1/2008 |
| JP | 5714508 B2 | 5/2015 |
| WO | WO 81/03272 A1 | 11/1981 |
| WO | WO 93/07817 A1 | 4/1993 |
| WO | WO 93/22973 A1 | 11/1993 |
| WO | WO 95/10978 A1 | 4/1995 |
| WO | WO 96/35382 A1 | 11/1996 |
| WO | WO 97/10764 A1 | 3/1997 |
| WO | WO 98/00069 A1 | 1/1998 |
| WO | WO 98/40020 A1 | 9/1998 |
| WO | WO 98/57588 A1 | 12/1998 |
| WO | WO 99/23960 A1 | 5/1999 |
| WO | WO 99/40861 A1 | 8/1999 |
| WO | WO 00/24330 A1 | 5/2000 |
| WO | WO 00/24331 A1 | 5/2000 |
| WO | WO 00/25691 A1 | 5/2000 |
| WO | WO 01/28444 A1 | 4/2001 |
| WO | WO 02/062241 A1 | 8/2002 |
| WO | WO 02/080797 A1 | 10/2002 |
| WO | WO 03/001986 A2 | 1/2003 |
| WO | WO 03/013374 A1 | 2/2003 |
| WO | WO 03/020339 A2 | 3/2003 |
| WO | WO 03/028541 A2 | 4/2003 |
| WO | WO 03/030708 A2 | 4/2003 |
| WO | WO 03/068046 A2 | 8/2003 |
| WO | WO 2004/011037 A2 | 2/2004 |
| WO | WO 2004/032754 A2 | 4/2004 |
| WO | WO 2004/032762 A1 | 4/2004 |
| WO | WO 2004/032763 A2 | 4/2004 |
| WO | WO 2004/078051 A2 | 9/2004 |
| WO | WO 2004/112618 A2 | 12/2004 |
| WO | WO 2005/052959 A2 | 6/2005 |
| WO | WO 2006/021269 A1 | 3/2006 |
| WO | WO 2006/036706 A1 | 4/2006 |
| WO | WO 2006/055166 A2 | 5/2006 |
| WO | WO 2006/119139 A2 | 11/2006 |
| WO | WO 2008/020964 A2 | 2/2008 |
| WO | WO 2008/045348 A2 | 4/2008 |
| WO | WO 2008/099529 A1 | 8/2008 |
| WO | WO 2008/101356 A1 | 8/2008 |
| WO | WO 2009/022614 A1 | 2/2009 |
| WO | WO 2009/036818 A1 | 3/2009 |
| WO | WO 2009/039179 A1 | 3/2009 |
| WO | WO 2009/059741 A1 | 5/2009 |
| WO | WO 2009/082477 A2 | 7/2009 |
| WO | WO 2009/149234 A1 | 12/2009 |
| WO | WO 2010/017266 A1 | 2/2010 |
| WO | WO 2010/104755 A1 | 9/2010 |
| WO | WO 2011/084768 A1 | 7/2011 |
| WO | WO 2011/089717 A1 | 7/2011 |
| WO | WO 2011/144911 A1 | 11/2011 |
| WO | WO 2012/044606 A2 | 4/2012 |
| WO | WO 2012/166510 A1 | 12/2012 |
| WO | WO 2013/034629 A1 | 3/2013 |
| WO | WO 2013/062978 A2 | 5/2013 |
| WO | WO 2013/154157 A1 | 10/2013 |
| WO | WO 2015/197395 A8 | 12/2015 |

OTHER PUBLICATIONS

Jang, J. et al. "Neuro-fuzzy and Soft Computing." Prentice Hall, 1997, pp. 13-89, 199-293, 335-393,453-496, 535-549.

International Search Report and Written Opinion for International Application No. PCT/US2015/018592 dated Aug. 25, 2015 (13 pages).

Weir, C.E., "Rate of shrinkage of tendon collagen—heat, entropy and free energy of activation of the shrinkage of untreated tendon. Effect of acid salt, pickle, and tannage on the activation of tendon collagen." Journal of the American Leather Chemists Association, 44, pp. 108-140 (1949).

Hörmann et al., "Reversible and irreversible denaturation of collagen fibers." Biochemistry, 10, pp. 932-937 (1971).

Henriques. F.C., "Studies in thermal injury V. The predictability and the significance of thermally induced rate processes leading to irreversible epidermal injury." Archives of Pathology, 434, pp. 489-502 (1947).

Arnoczky et al., "Thermal Modification of Conective Tissues: Basic Science Considerations and Clinical Implications," J. Am Acad Orthop Surg, vol. 8, No. 5, pp. 305-313 (Sep./Oct. 2000).

Chen et al., "Heat-induced changes in the mechanics of a collagenous tissue: pseudoelastic behavior at 37° C," Journal of Biomechanics, 31, pp. 211-216 (1998).

Chen et al., "Heat-Induced Changes in the Mechanics of a Collagenous Tissue: Isothermal Free Shrinkage," Transactions of the ASME, vol. 119, pp. 372-378 (Nov. 1997).

Chen et al., "Heat-Induced Changes in the Mechanics of a Collagenous Tissue: Isothermal, Isotonic Shrinkage," Transactions of the ASME, vol. 120, pp. 382-388 (Jun. 1998).

(56) References Cited

OTHER PUBLICATIONS

Chen et al., "Phenomenological Evolution Equations for Heat-Induced Shrinkage of a Collagenous Tissue," IEEE Transactions on Biomedical Engineering, vol. 45, No. 10, pp. 1234-1240 (Oct. 1998).

Harris et al., "Kinetics of Thermal Damage to a Collagenous Membrane Under Biaxial Isotonic Loading," IEEE Transactions on Biomedical Engineering, vol. 51, No. 2, pp. 371-379 (Feb. 2004).

Harris et al., "Altered Mechanical Behavior of Epicardium Due to Isothermal Heating Under Biaxial Isotonic Loads," Journal of Biomechanical Engineering, vol. 125, pp. 381-388 (Jun. 2003).

Hayashi et al., "The Effect of Thermal Heating on the Length and Histologic Properties of the Glenohumeral Joint Capsule," American Journal of Sports Medicine, vol. 25, Issue 1, 11 pages (Jan. 1997), URL: http://www.mdconsult.com/das/article/body/156183648-2/journal&source=MI&sp=1 . . . , accessed Aug. 25, 2009.

Lee et al., "A multi-sample denaturation temperature tester for collagenous biomaterials," Med. Eng. Phy., vol. 17, No. 2, pp. 115-121 (Mar. 1995).

Moran et al., "Thermally Induced Shrinkage of Joint Capsule," Clinical Orthopaedics and Related Research, No. 281, pp. 248-255 (Dec. 2000).

Wall et al., "Thermal modification of collagen," J Shoulder Elbow Surg, No. 8, pp. 339-344 (Jul./Aug. 1999).

Wells et al., "Altered Mechanical Behavior of Epicardium Under Isothermal Biaxial Loading," Transactions of the ASME, Journal of Biomedical Engineering, vol. 126, pp. 492-497 (Aug. 2004).

Gibson, "Magnetic Refrigerator Successfully Tested," U.S. Department of Energy Research News, accessed online on Aug. 6, 2010 at http://www.eurekalert.org/features/doe/2001-11/dl-mrs062802.php (Nov. 1, 2001).

Humphrey, J.D., "Continuum Thermomechanics and the Clinical Treatment of Disease and Injury," Appl. Mech. Rev., vol. 56, No. 2 pp. 231-260 (Mar. 2003).

Kurt Gieck & Reiner Gieck, *Engineering Formulas* § Z.7 (7th ed. 1997).

National Semiconductors Temperature Sensor Handbook—http://www.national.com/appinfo/tempsensors/files/temphb.pdf; accessed online: Apr. 1, 2011.

Glaser and Subak-Sharpe, *Integrated Circuit Engineering*, Addison-Wesley Publishing, Reading, MA (1979). (book—not attached).

Wright, et al., "Time-Temperature Equivalence of Heat-Induced Changes in Cells and Proteins," Feb. 1998. ASME Journal of Biomechanical Engineering, vol. 120, pp. 22-26.

Covidien Brochure, [Value Analysis Brief], LigaSure Advance™ Pistol Grip, dated Rev. Apr. 2010 (7 pages).

Covidien Brochure, LigaSure Impact™ Instrument LF4318, dated Feb. 2013 (3 pages).

Covidien Brochure, LigaSure Atlas™ Hand Switching Instruments, dated Dec. 2008 (2 pages).

Covidien Brochure, The LigaSure™ 5 mm Blunt Tip Sealer/Divider Family, dated Apr. 2013 (2 pages).

Covidien Brochure, The LigaSure Precise™ Instrument, dated Mar. 2011 (2 pages).

Erbe Electrosurgery VIO® 200 S, (2012), p. 7, 12 pages, accessed Mar. 31, 2014 at http://www.erbe-med.com/erbe/media/Marketingmaterialien/85140-170_ERBE_EN_VIO_200_S_D027541.

Sullivan, "Cost-Constrained Selection of Strand Diameter and Number in a Litz-Wire Transformer Winding," IEEE Transactions on Power Electronics, vol. 16, No. 2, Mar. 2001, pp. 281-288.

Sullivan, "Optimal Choice for Number of Strands in a Litz-Wire Transformer Winding," IEEE Transactions on Power Electronics, vol. 14, No. 2, Mar. 1999, pp. 283-291.

https://www.kjmagnetics.com/fieldcalculator.asp, retrieved Jul. 11, 2016, backdated to Nov. 11, 2011 via https://web.archive.org/web/20111116164447/http://www.kjmagnetics.com/fieldcalculator.asp.

U.S. Appl. No. 12/576,529, filed Oct. 9, 2009.

\* cited by examiner

DETECTING SHORT CIRCUITS IN ELECTROSURGICAL MEDICAL DEVICES

BACKGROUND

Electrosurgical instruments are a type of surgical instrument used in many surgical operations. Electrosurgical instruments apply electrical energy to tissue in order to treat tissue. An electrosurgical instrument may comprise an instrument having a distally-mounted end effector comprising one or more electrodes. The end effector can be positioned against tissue such that electrical current is introduced into the tissue. Electrosurgical instruments can be configured for bipolar or monopolar operation. During bipolar operation, current is introduced into and returned from the tissue by active and return electrodes, respectively, of the end effector. During monopolar operation, current is introduced into the tissue by an active (or source) electrode of the end effector and returned through a return electrode (e.g., a grounding pad) separately located on a patient's body. Heat generated by the current flow through the tissue may form hemostatic seals within the tissue and/or between tissues and thus may be particularly useful for sealing blood vessels, for example. The end effector of an electrosurgical instrument sometimes also comprises a cutting member that is moveable relative to the tissue and the electrodes to transect the tissue.

Electrical energy applied by an electrosurgical instrument can be transmitted to the instrument by a generator. The generator may form an electrosurgical signal that is applied to an electrode or electrodes of the electrosurgical instrument. The generator may be external or integral to the electrosurgical instrument. The electrosurgical signal may be in the form of radio frequency ("RF") energy. For example, RF energy may be provided at a frequency range of between 100 kHz and 1 MHz. During operation, an electrosurgical instrument can transmit RF energy through tissue, which causes ionic agitation, or friction, in effect resistive heating, thereby increasing the temperature of the tissue. Because a sharp boundary may be created between the affected tissue and the surrounding tissue, surgeons can operate with a high level of precision and control, without sacrificing un-targeted adjacent tissue. The low operating temperatures of RF energy may be useful for removing, shrinking, or sculpting soft tissue while simultaneously sealing blood vessels. RF energy may work particularly well on connective tissue, which is primarily comprised of collagen and shrinks when contacted by heat.

Short circuits are a recurrent problem for electrosurgical instruments. For example, if a conductive clip, staple or other non-tissue conductive object is present between the electrodes of an electrosurgical instrument and touching both polarities simultaneously, electrosurgical energy can be shunted through the conductive object. Additionally, in the case of bipolar forceps, the electrodes can touch each other during normal usage. This contact shunts electrical energy away from the tissue and the surgeon has to open the forceps and re-grasp the tissue. This can result in several undesirable outcomes including, for example, incomplete tissue effect, excessive heating of the conductive object, a delay of the surgery, clinician inconvenience or frustration, etc. Existing methods for coping with short circuits utilize the generator or other suitable component to determine when the impedance between the electrodes falls below a threshold value, for example, for a threshold amount of time. When such an impedance drop is detected, the generator alerts the clinician, who can then reposition the electrodes and/or remove the conducting object. Existing methods, however, suffer when tissue impedance itself drops during treatment. For example, during electrosurgical treatment, localized tissue impedance can often fall as low as just a few ohms. Existing methods are often inadequate for distinguishing between short circuits and normally occurring low tissue impedance.

SUMMARY

Various embodiments are directed to an electrosurgical system for providing an electrosurgical signal to a patient. The system may comprise a control circuit. The control circuit may be programmed to provide the electrosurgical signal to first and second electrodes, where the electrosurgical signal defines a plurality of pulses. The control circuit may also be programmed to receive a first reading of an impedance between the first and second electrodes taken at a first point of a first pulse of the electrosurgical signal and receive a second reading of the impedance between the first and second electrodes taken at a first point of a second pulse of the electrosurgical signal. The first point of the first pulse and the first point of the second pulse may be at equivalent positions within the first and second pulses. Based on a comparison of the first reading and the second reading, the control circuit may also be programmed to determine that a short circuit is present between the first and second electrodes and generate a signal indicating the short circuit between the first and second electrodes. Embodiments for detecting short circuits utilizing various other methods are also disclosed.

FIGURES

The features of the various embodiments are set forth with particularity in the appended claims. The various embodiments, however, both as to organization and methods of operation, together with advantages thereof, may best be understood by reference to the following description, taken in conjunction with the accompanying drawings as follows:

DESCRIPTION

Reference will now be made in detail to several embodiments, including embodiments showing example implementations of electrosurgical instruments for cutting and coagulating tissue. Wherever practicable similar or like reference numbers may be used in the figures and may indicate similar or like functionality. The figures depict example embodiments of the disclosed electrosurgical instruments and/or methods of use for purposes of illustration only. One skilled in the art will readily recognize from the following description that alternative example embodiments of the structures and methods illustrated herein may be employed without departing from the principles described herein.

Figure 1:
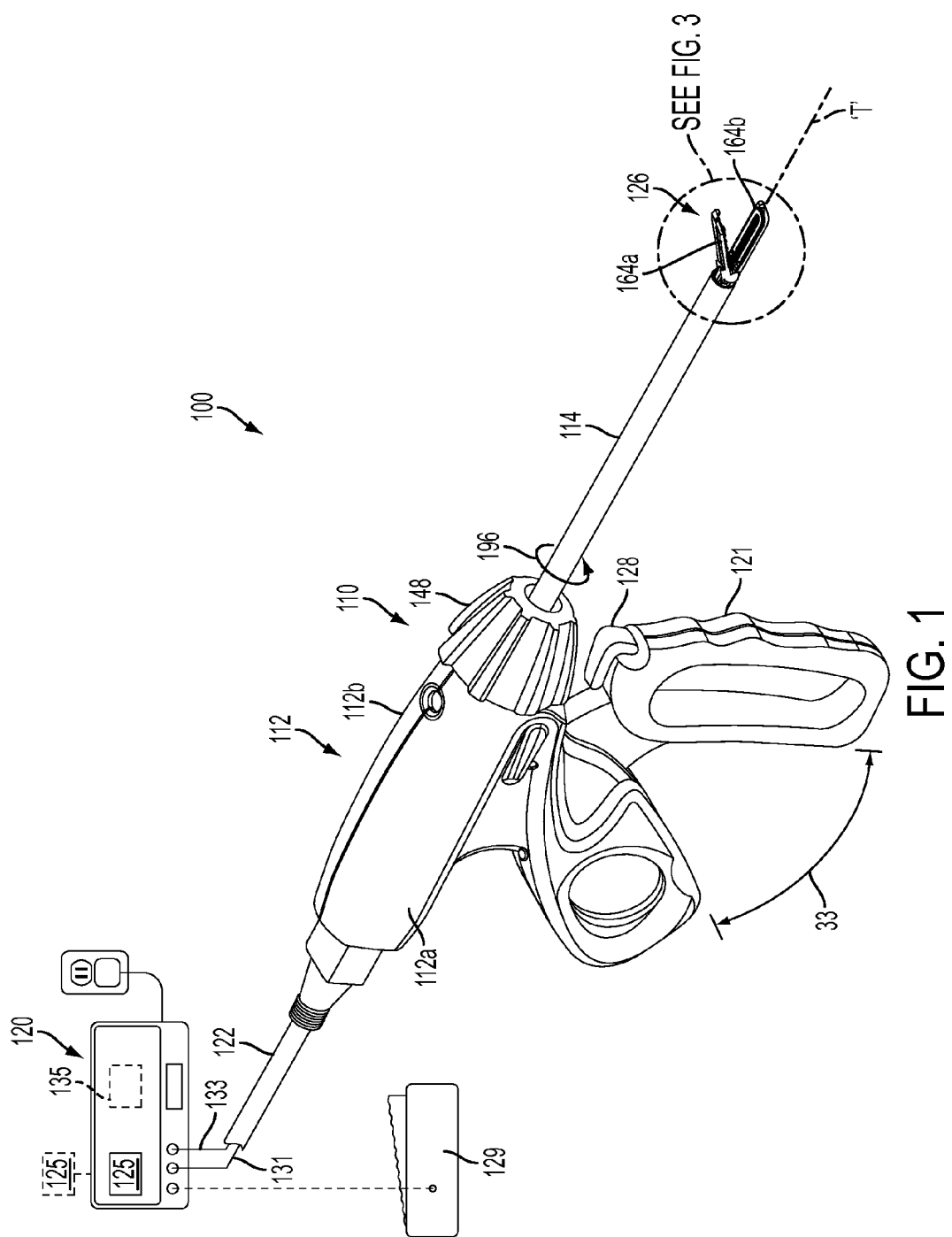
FIG. 1 shows a perspective view of one example embodiment of a surgical system shows a perspective view of one example embodiment of a surgical instrument system comprising an electrosurgical instrument and an external generator.

Electrosurgical instruments utilize therapeutic and/or sub-therapeutic electrical energy to treat tissue and/or provide feedback to the generators. The various electrosurgical instruments described herein are adapted for use in a manual or hand-operated manner, although electrosurgical instruments with the features described herein may be used in robotic applications as well. FIG. 1 shows a perspective view of one example embodiment of a surgical system 100 comprising an electrosurgical instrument 110 and an external generator 120. The electrosurgical instrument 110 may comprise a proximal handle 112, a distal working end or end effector 126 and an introducer or elongated shaft 114 disposed in-between.

The electrosurgical system 100 can be configured to supply energy, such as electrical energy, ultrasonic energy, heat energy, or any combination thereof, to the tissue of a patient either independently or simultaneously, for example. In one example embodiment, the electrosurgical system 100 includes the generator 120 in electrical communication with the electrosurgical instrument 110. The generator 120 is connected to the electrosurgical instrument 110 via a suitable transmission medium such as a cable 122. In one example embodiment, the generator 120 is coupled to a controller, such as a control circuit 125, for example. In various embodiments, the control circuit 125 may be formed integrally with the generator 120 or may be provided as a separate circuit module or device electrically coupled to the generator 120 (shown in phantom to illustrate this option). The control circuit 125 may comprise any suitable analog and/or digital hardware for controlling the generator 102 and/or the instrument 110 in the manner described herein. For example, in some embodiments, the control circuit 125 may comprise at least one processor and operatively associated memory. In some embodiments, the control circuit 125 may comprise a digital signal processor (DSP). Also, in addition to or instead of a processor, the control circuit 125 may comprise various other components including, for example, one or more field programmable gate arrays (FPGA's), application specific integrated circuits (ASIC's), etc.

Although in the presently disclosed embodiment, the generator 120 is shown separate from the electrosurgical instrument 110, in one example embodiment, the generator 120 (and/or the control circuit 125) may be formed integrally with the electrosurgical instrument 110 to form a unitary electrosurgical system 100, where a battery located within the electrosurgical instrument 110 is the energy source and a circuit coupled to the battery produces the suitable electrical energy, ultrasonic energy, or heat energy. One such example is described herein below in connection with FIGS. 7-8C. The generator 120 may comprise an input device 135 located on a front panel of the generator 120 console. The input device 135 may comprise any suitable device that generates signals suitable for programming the operation of the generator 120, such as a keyboard, or input port, for example.

Referring now to the end effector 126, electrodes in the first jaw 164a and the second jaw 164b may be coupled to the generator 120 via the handle 112 and cable 122. The cable 122 may comprise multiple electrical conductors for the application of electrical energy to positive (+) and negative (−) electrodes of the electrosurgical instrument 110. For example, the cable 122 may comprise at least one supply conductor 131 and at least one return conductor 133. In various embodiments, the supply conductor 131 and the return conductor 133 may comprise insulated wires and/or any other suitable type of conductor. In certain embodiments, as described below, the supply conductor 131 and the return conductor 133 may be contained within and/or may comprise the cable 122 extending between, or at least partially between, the generator 120 and the end effector 126 of the electrosurgical instrument 110. In any event, the generator 120 can be configured to apply a sufficient voltage differential between the supply conductor 131 and the return conductor 133 such that sufficient current can be supplied to the end effector 126.

The control circuit 125 may be used to activate the generator 120, which may serve as an electrical source. The generator may create an electrosurgical signal provided to the electrodes of the jaws 164a, 164b via the handle 112. In various embodiments, the generator 120 may comprise an RF or electrosurgical source, an ultrasonic source, a direct current source, and/or any other suitable type of electrical energy source, for example, which may be activated independently or simultaneously.

Figure 2:
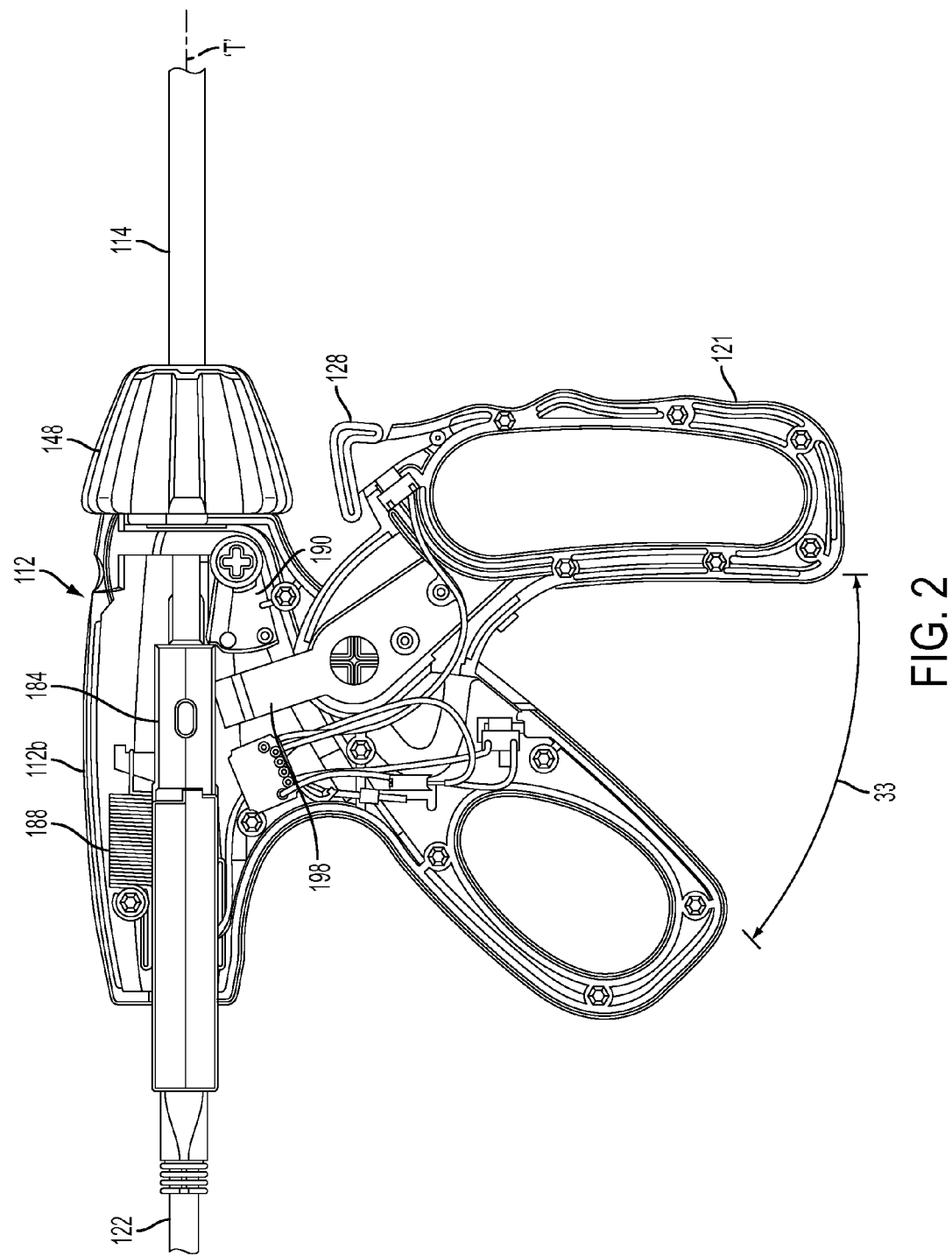
FIG. 2 shows a side view of one example embodiment of the handle of the surgical instrument of FIG. 1 with half of a first handle body removed to illustrate various components within the second handle body.

FIG. 2 shows a side view of one example embodiment of the handle 112 of the surgical instrument 110 with half of a first handle body 112a (see FIG. 1) removed to illustrate various components within the second handle body 112b. The handle 112 may comprise a lever arm 121 (e.g., a trigger) which may be pulled along a path 33. The lever arm 121 may be coupled to an axially moveable member 178 (FIGS. 3-6) disposed within the elongated shaft 114 by a shuttle 184 operably engaged to an extension 198 of lever arm 121. The shuttle 184 may further be connected to a biasing device, such as a spring 188, which may also be connected to the second handle body 112b, to bias the shuttle 184 and thus the axially moveable member 178 in a proximal direction, thereby urging the jaws 164a and 164b to an open position as seen in FIG. 1. Also, referring to FIGS. 1-2, a locking member 190 (see FIG. 2) may be moved by a button 128 (see FIG. 1) between a locked position, where the shuttle 184 is substantially prevented from moving distally as illustrated, and an unlocked position, where the shuttle 184 may be allowed to freely move in the distal direction, toward the elongated shaft 114. The handle 112 can be any type of pistol-grip or other type of handle known in the art that is configured to carry actuator levers, triggers or sliders for actuating the first jaw 164a and the second jaw 164b. In some embodiments, the handle 112 may comprise a pencil-style handle. The elongated shaft 114 may have a cylindrical or rectangular cross-section, for example, and can comprise a thin-wall tubular sleeve that extends from handle 112. The elongated shaft 114 may include a bore extending therethrough for carrying actuator mechanisms, for example, the axially moveable member 178, for actuating the jaws and for carrying electrical leads for delivery of electrical energy to electrosurgical components of the end effector 126.

The end effector 126 may be adapted for capturing and transecting tissue and for contemporaneously welding the captured tissue with controlled application of energy (e.g., RF energy). The first jaw 164a and the second jaw 164b may close to thereby capture or engage tissue about a longitudinal axis "T" defined by the axially moveable member 178. The first jaw 164a and second jaw 164b may also apply compression to the tissue. In some embodiments, the elongated shaft 114, along with the first jaw 164a and second jaw 164b, can be rotated a full 360° degrees, as shown by the arrow 196 (see FIG. 1), relative to the handle 112. For example, a rotation knob 148 may be rotatable about the longitudinal axis of the shaft 114 and may be coupled to the shaft 114 such that rotation of the knob 148 causes corresponding rotation of the shaft 114. The first jaw 164a and the second jaw 164b can remain openable and/or closeable while rotated. Also, in some embodiments, the elongated shaft 114 may be articulable, allowing for a further range of motion. Examples of surgical devices with articulable shafts are provided in U.S. Patent Application Publication No. 2014/0005680, filed on Jun. 28, 2012, entitled, ELECTRODE CONNECTIONS FOR ROTARY DRIVEN SURGICAL TOOLS, the entire disclosure of which is incorporated herein by reference.

Figure 3:
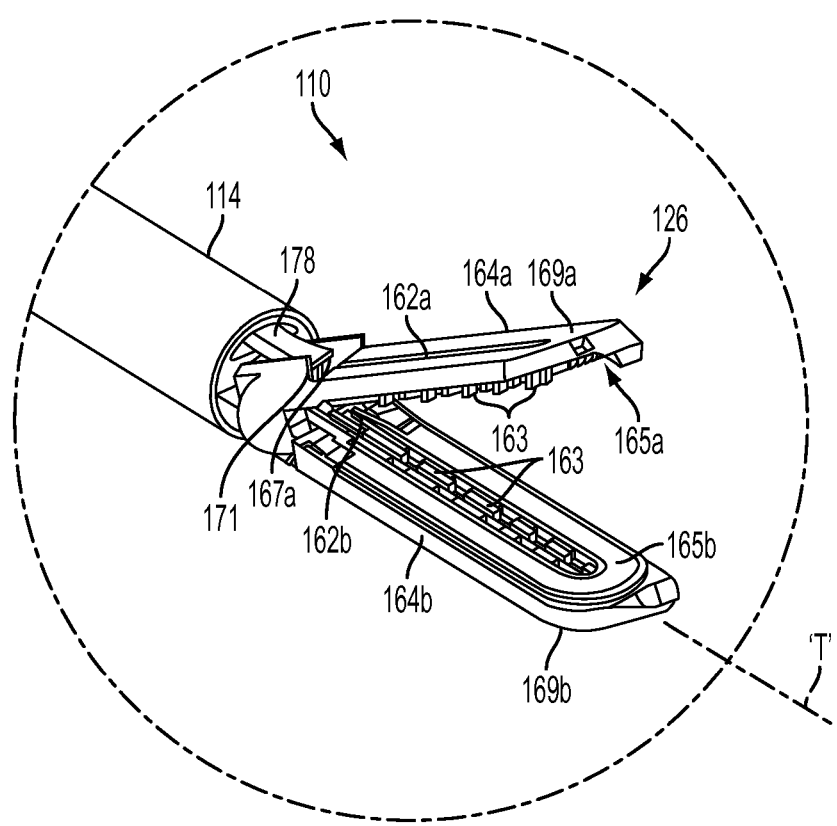
FIG. 3 shows a perspective view of one embodiment of the end effector of the surgical instrument of FIG. 1 with the jaws open and the distal end of an axially moveable member in a retracted position.
Figure 4:
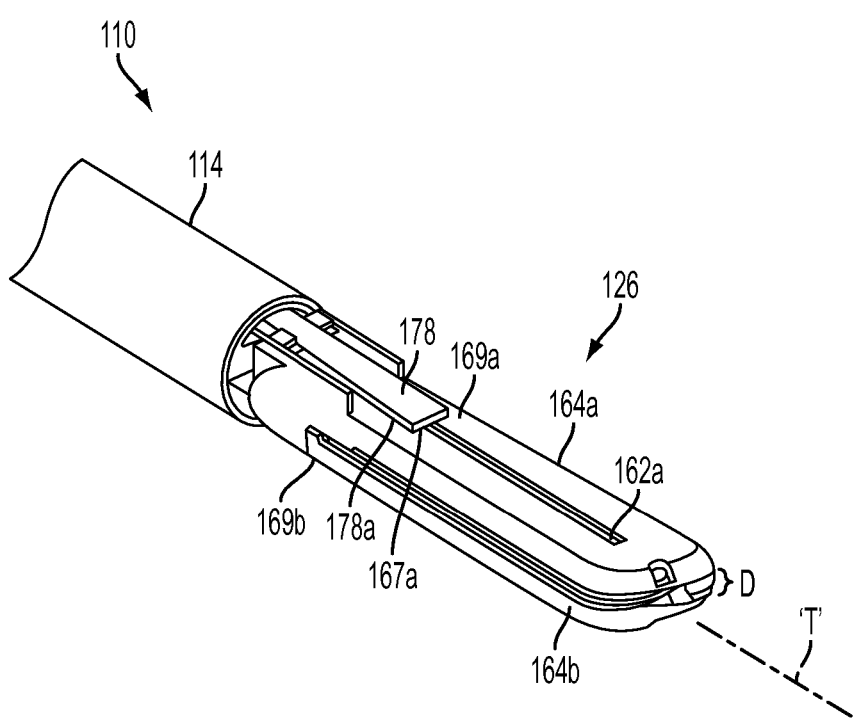
FIG. 4 shows a perspective view of one embodiment of the end effector of the surgical instrument of FIG. 1 with the jaws closed and the distal end of an axially moveable member in a partially advanced position.

FIG. 3 shows a perspective view of one example embodiment of the end effector 126 with the jaws 164a, 164b open and the distal end of the axially moveable member 178 in a retracted position. FIG. 4 shows a perspective view of one embodiment of the end effector 126 with the jaws 164a, 164b closed and the distal end of the axially moveable member 178 in a partially advanced position. As noted above, the end effector 126 may comprise the upper first jaw 164a and the lower second jaw 164b, which may be straight or curved. The first jaw 164a and the second jaw 164b may each comprise an elongated slot or channel 162a and 162b, respectively, disposed outwardly along their respective middle portions. Further, the first jaw 164a and the second jaw 164b may each have tissue-gripping elements, such as teeth 163, disposed on the inner portions of the first jaw 164a and the second jaw 164b. The first jaw 164a may comprise an upper first jaw body with an upper first outward-facing surface 169a and an upper first energy delivery surface 165a. The second jaw 164b may comprise a lower second jaw body with a lower second outward-facing surface 169b and a lower second energy delivery surface 165b. The first energy delivery surface 165a and the second energy delivery surface 165b may both extend in a "U" shape about the distal end of the end effector 126.

Figure 5:
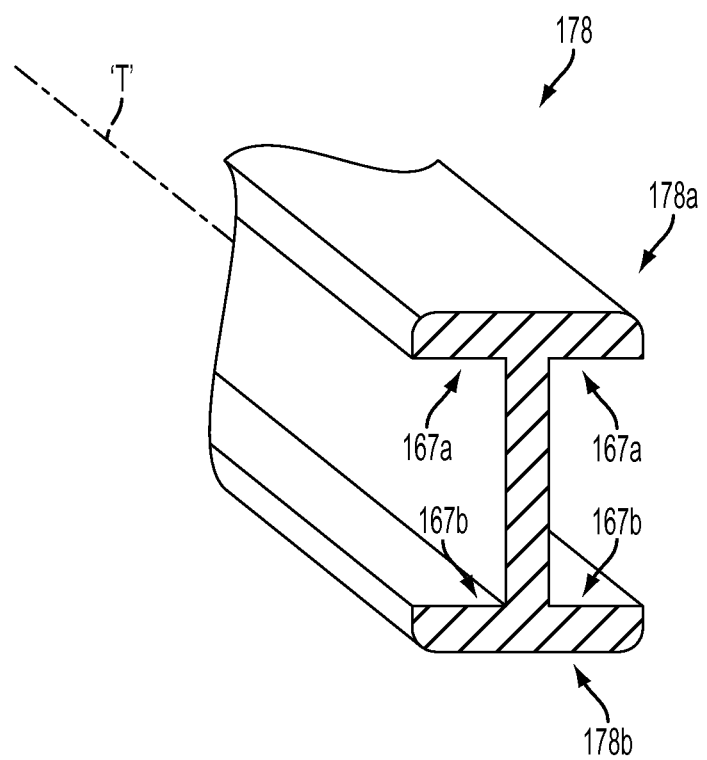
FIG. 5 shows a perspective view of one embodiment of the axially moveable member of the surgical instrument of FIG. 1.

The lever arm 121 of the handle 112 (FIG. 2) may be adapted to actuate the axially moveable member 178, which also may function as a jaw-closing mechanism. For example, the axially moveable member 178 may be urged distally as the lever arm 121 is pulled proximally along the path 33 via the shuttle 184, as shown in FIG. 2 and discussed above. FIG. 5 is a perspective view of one example embodiment of the axially moveable member 178 of the surgical instrument 110. The axially moveable member 178 may comprise one or several pieces, but in any event, may be moveable or translatable with respect to the elongated shaft 114 and/or the jaws 164a, 164b. Also, in at least one example embodiment, the axially moveable member 178 may be made of 17-4 precipitation hardened stainless steel. The distal end of axially moveable member 178 may comprise a flanged "I"-beam configured to slide within the channels 162a and 162b in jaws 164a and 164b. The axially moveable member 178 may slide within the channels 162a, 162b to open and close the first jaw 164a and the second jaw 164b. The distal end of the axially moveable member 178 may also comprise an upper flange or "c"-shaped portion 178a and a lower flange or "c"-shaped portion 178b. The flanges 178a, 178b respectively define inner cam surfaces 167a and 167b for engaging outward facing surfaces of the first jaw 164a and the second jaw 164b. The opening-closing of jaws 164a and 164b can apply very high compressive forces on tissue using cam mechanisms which may include moveable "I-beam" axially moveable member 178 and the outward facing surfaces 169a, 169b of jaws 164a, 164b.

More specifically, referring now to FIGS. 3-5, collectively, the inner cam surfaces 167a and 167b of the distal end of axially moveable member 178 may be adapted to slidably engage the first outward-facing surface 369a and the second outward-facing surface 169b of the first jaw 164a and the second jaw 164b, respectively. The channel 162a within first jaw 164a and the channel 162b within the second jaw 164b may be sized and configured to accommodate the movement of the axially moveable member 178, which may comprise a tissue-cutting element 171, for example, comprising a sharp distal edge. FIG. 4, for example, shows the distal end of the axially moveable member 178 advanced at least partially through channels 162a and 162b (FIG. 3). The advancement of the axially moveable member 178 may close the end effector 126 from the open configuration shown in FIG. 3. In the closed position shown by FIG. 4, the upper first jaw 164a and the lower second jaw 164b define a gap or dimension D between the first energy delivery surface 165a and second energy delivery surface 165b of the first jaw 164a and the second jaw 164b, respectively. In various embodiments, dimension the D can equal from about 0.0005" to about 0.040", for example, and in some embodiments, between about 0.001" to about 0.010", for example. Also, the edges of the first energy delivery surface 165a and the second energy delivery surface 165b may be rounded to prevent the dissection of tissue.

Figure 6:
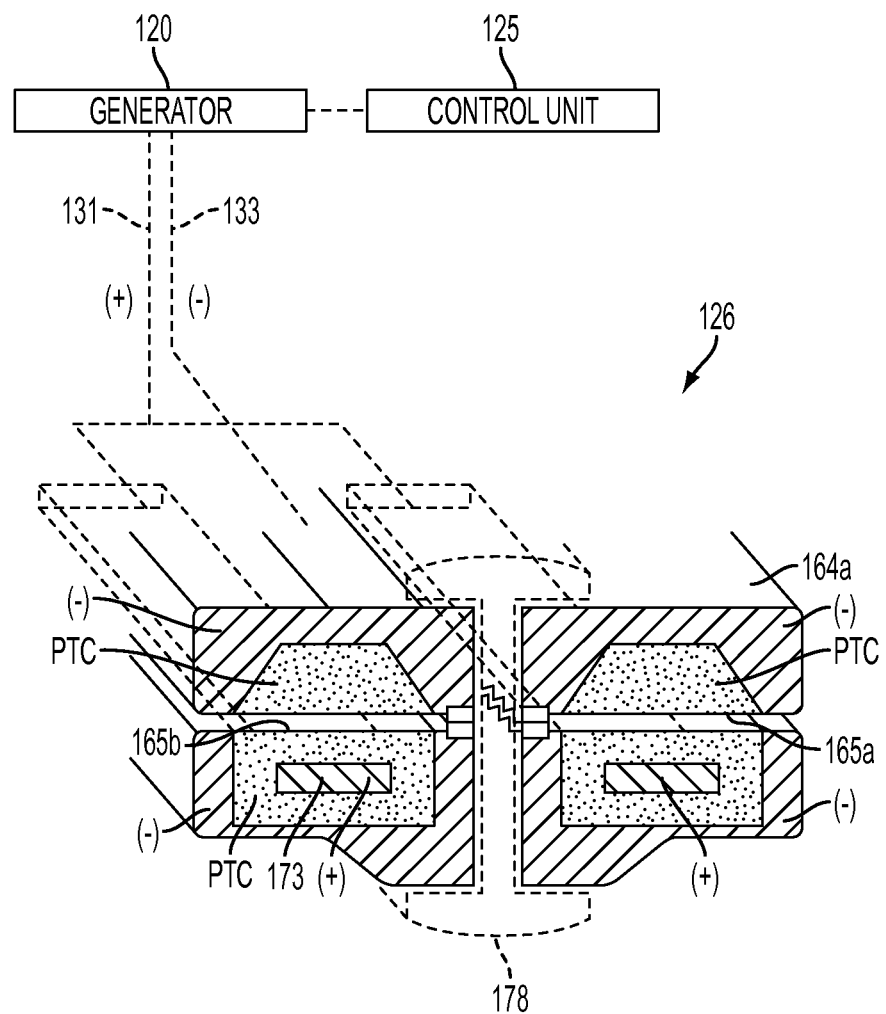
FIG. 6 shows a section view of one embodiment of the end effector of the surgical instrument of FIG. 1.

FIG. 6 is a section view of one example embodiment of the end effector 126 of the surgical instrument 110. The second energy delivery surface 165b of the lower jaw 164b is adapted to deliver energy to tissue, at least in part, through a conductive-resistive matrix, such as a variable resistive PTC body, as discussed in more detail below. At least one of the upper and lower jaws 164a, 164b may carry at least one electrode 173 configured to deliver the energy from the generator 120 to the captured tissue. The first energy delivery surface 165a of the upper jaw 164a may carry a similar conductive-resistive matrix (i.e., a PTC material), or in some embodiments the surface may be a conductive electrode or an insulative layer, for example. Alternatively, the engagement surfaces of the jaws can carry any of the energy delivery components disclosed in U.S. Pat. No. 6,773,409, filed Oct. 22, 2001, entitled ELECTROSURGICAL JAW STRUCTURE FOR CONTROLLED ENERGY DELIVERY, the entire disclosure of which is incorporated herein by reference.

The first energy delivery surface 165a and the second energy delivery surface 165b each may be in electrical communication with the generator 120. The first energy delivery surface 165a and the second energy delivery surface 165b may be configured to contact tissue and deliver electrosurgical energy to captured tissue which are adapted to seal or weld the tissue. The control circuit 125 regulates the electrical energy delivered by electrical generator 120 which in turn delivers electrosurgical energy to the first energy delivery surface 165a and the second energy delivery surface 165b. The energy delivery may be initiated by an activation button 128 (FIG. 2) operably engaged with the lever arm 121 and in electrical communication with the generator 120 via a cable 122. In one example embodiment, the electrosurgical instrument 110 may be energized by the generator 120 by way of a foot switch 129 (FIG. 1). When actuated, the foot switch 129 triggers the generator 120 to deliver electrical energy to the end effector 126, for example. The control circuit 125 may regulate the power generated by the generator 120 during activation. Although the foot switch 129 may be suitable in many circumstances, other suitable types of switches can be used, such as, for example, a thumb switch.

As mentioned above, the electrosurgical energy delivered by electrical generator 120 and regulated, or otherwise controlled, by the control circuit 125 may comprise radio frequency (RF) energy, or other suitable forms of electrical energy. Further, the opposing first and second energy delivery surfaces 165a and 165b may carry variable resistive PTC bodies that are in electrical communication with the generator 120 and the control circuit 125. Additional details regarding electrosurgical end effectors, jaw closing mechanisms, and electrosurgical energy-delivery surfaces are described in the following U.S. patents and published patent applications: U.S. Pat. Nos. 7,087,054; 7,083,619; 7,070,597; 7,041,102; 7,011,657; 6,929,644; 6,926,716; 6,913,579; 6,905,497; 6,802,843; 6,770,072; 6,656,177; 6,533,784; and 6,500,112; and U.S. Pat. App. Pub. Nos. 2010/0036370 and 2009/0076506, all of which are incorporated herein by reference in their entirety and made part of this specification.

In one example embodiment, the generator 120 may be implemented as an electrosurgery unit (ESU) capable of supplying power sufficient to perform bipolar electrosurgery using radio frequency (RF) energy. In one example embodiment, the ESU can be a bipolar ERBE ICC 150 sold by ERBE USA, Inc. of Marietta, Ga. and/or a GEN11 generator sold by Ethicon Endo-Surgery of Cincinnati, Ohio. In some embodiments, such as for bipolar electrosurgery applications, a surgical instrument having an active electrode and a return electrode can be utilized, wherein the active electrode and the return electrode can be positioned against, adjacent to and/or in electrical communication with, the tissue to be treated such that current can flow from the active electrode, through the PTC bodies and to the return electrode through the tissue. Thus, in various embodiments, the electrosurgical system 100 may comprise a supply path and a return path, where the captured tissue being treated completes, or closes, the circuit. In other embodiments, the operator may provide subtherapeutic RF energy levels for purposes of evaluating tissue conditions and providing feedback in the electrosurgical system 100. Such feed back may be employed to control the therapeutic RF energy output of the electrosurgical instrument 110.

During operation of electrosurgical instrument 110, the user generally grasps tissue, supplies energy to the grasped tissue to form a weld or a seal (e.g., by actuating button 128 and/or foot switch 129), and then drives a tissue-cutting element 171 at the distal end of the axially moveable member 178 through the grasped tissue. According to various embodiments, the translation of the axial movement of the axially moveable member 178 may be paced, or otherwise controlled, to aid in driving the axially moveable member 178 at a suitable rate of travel. By controlling the rate of the travel, the likelihood that the captured tissue has been properly and functionally sealed prior to transection with the cutting element 171 is increased.

Figure 7:
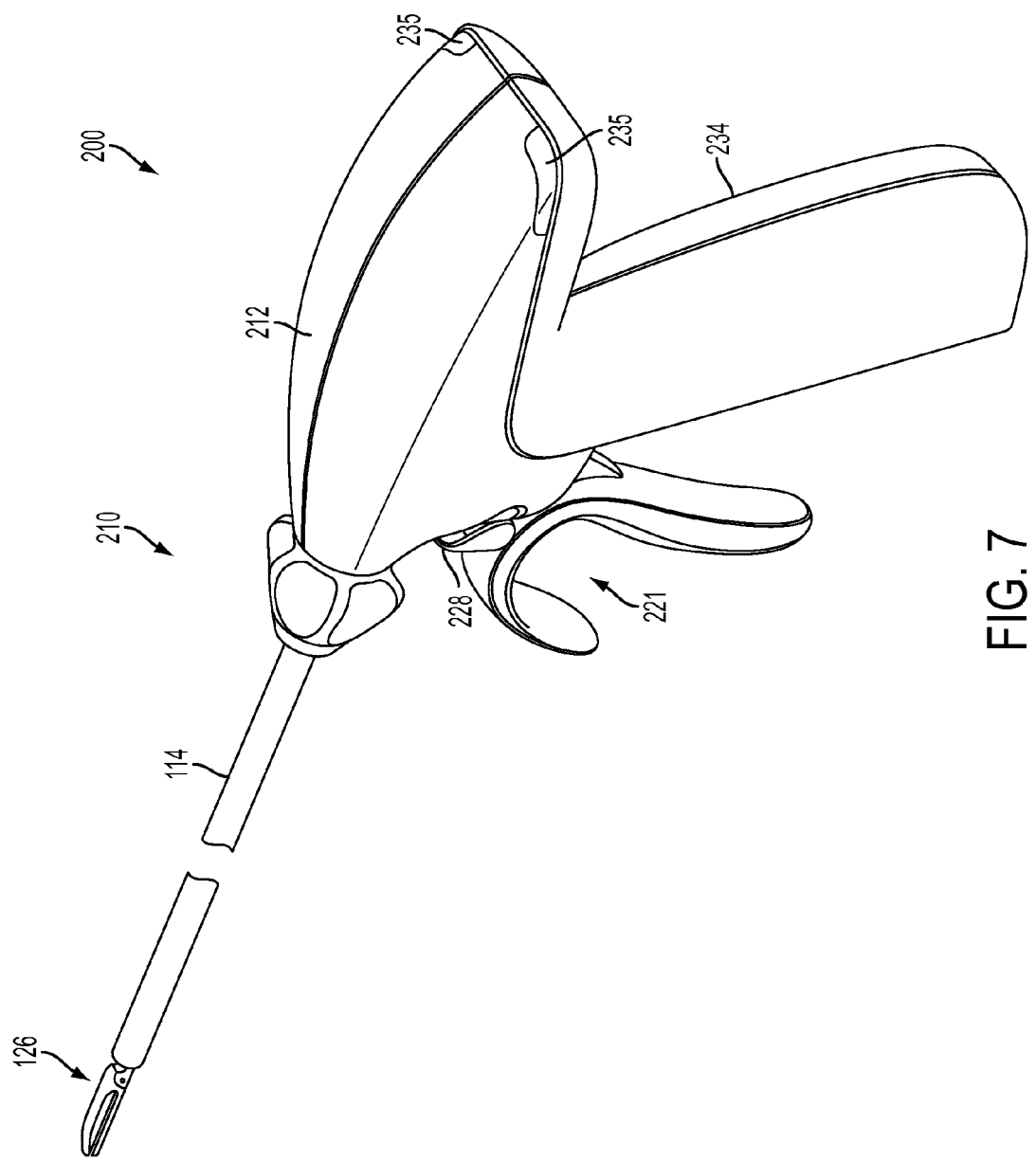
FIG. 7 shows a perspective view of one example embodiment of a surgical instrument system comprising a cordless electrical energy surgical instrument with an integral generator.

FIG. 7 shows a perspective view of one example embodiment of a surgical instrument system 200 comprising a cordless electrical energy surgical instrument 210 with an integral generator (not shown in FIG. 7). The electrosurgical system 200 is similar to the electrosurgical system 100. The electrosurgical system 200 can be configured to supply energy, such as electrical energy, ultrasonic energy, heat energy, or any combination thereof, to the tissue of a patient either independently or simultaneously as described in connection with FIG. 1, for example. The electrosurgical instrument 210 may utilize the end effector 126 and elongated shaft 114 described here in conjunction with a cordless proximal handle 212. In one example embodiment, the handle 212 includes the integral generator circuit 220 (see FIG. 8A). The generator circuit 220 performs a function substantially similar to that of generator 120. In one example embodiment, the generator circuit 220 is coupled to a controller or control circuit (e.g., 281 in FIG. 8B). In the illustrated embodiment, the control circuit is integrated into the generator circuit 220. In other embodiments, the control circuit may be separate from the generator circuit 220.

In one example embodiment, various electrodes in the end effector 126 (including the first and second jaws 164a, 164b thereof) may be coupled to the generator circuit 220. The control circuit may be used to activate the generator 220, which may serve as an electrical source. In various embodiments, the generator 220 may comprise an RF source, an ultrasonic source, a direct current source, and/or any other suitable type of electrical energy source, for example. In one example embodiment, a button 228 may be provided to activate the generator circuit 220 to provide energy to the end effector 126.

Figure 8A:
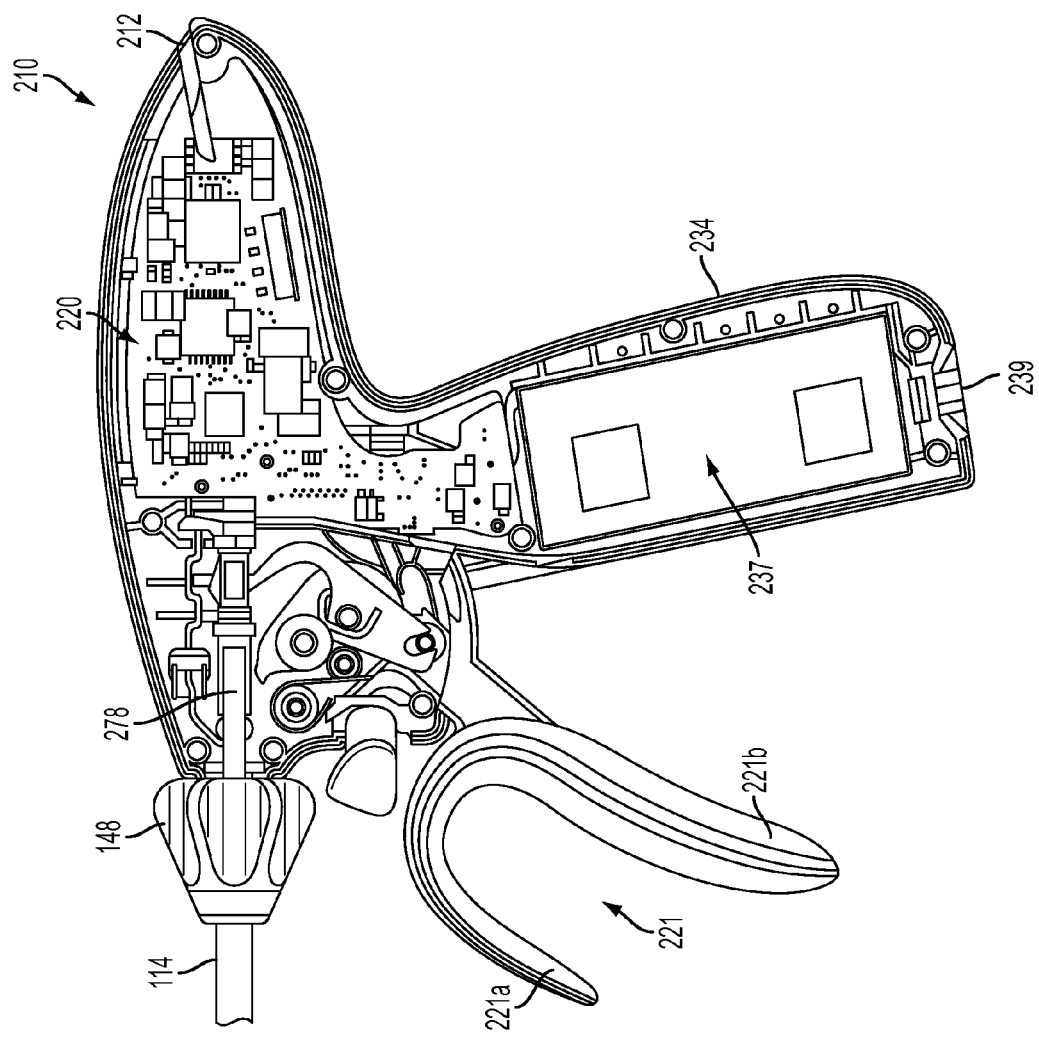
FIG. 8A shows a side view of a handle of one embodiment of the surgical instrument of FIG. 7 with half of the handle body removed to illustrate various components therein.

FIG. 8A shows a side view of one example embodiment of the handle 212 of the cordless surgical instrument 210 with half of a first handle body removed to illustrate various components within the second handle body 234. The handle 212 may comprise a lever arm 221 (e.g., a trigger) which may be pulled along a path 33 around a pivot point. The lever arm 221 may be coupled to an axially moveable member 278 disposed within the elongated shaft 114 by a shuttle operably engaged to an extension of lever arm 221. In one example embodiment, the lever arm 221 defines a shepherd's hook shape comprising a distal trigger hook 221a and a proximal trigger portion 221b. As illustrated, the distal trigger hook 221a may have a first length while the proximal trigger portion 221b may have a second length with the second length greater than the first length.

In one example embodiment, the cordless electrosurgical instrument comprises a battery 237. The battery 237 provides electrical energy to the generator circuit 220. The battery 237 may be any battery suitable for driving the generator circuit 220 at the desired energy levels. In one example embodiment, the battery 237 is a 1030 mAhr, triple-cell Lithium Ion Polymer battery. The battery may be fully charged prior to use in a surgical procedure, and may hold a voltage of about 12.6V. The battery 237 may have two fuses fitted to the cordless electrosurgical instrument 210, arranged in line with each battery terminal. In one example embodiment, a charging port 239 is provided to connect the battery 237 to a DC current source (not shown).

Figure 8B:
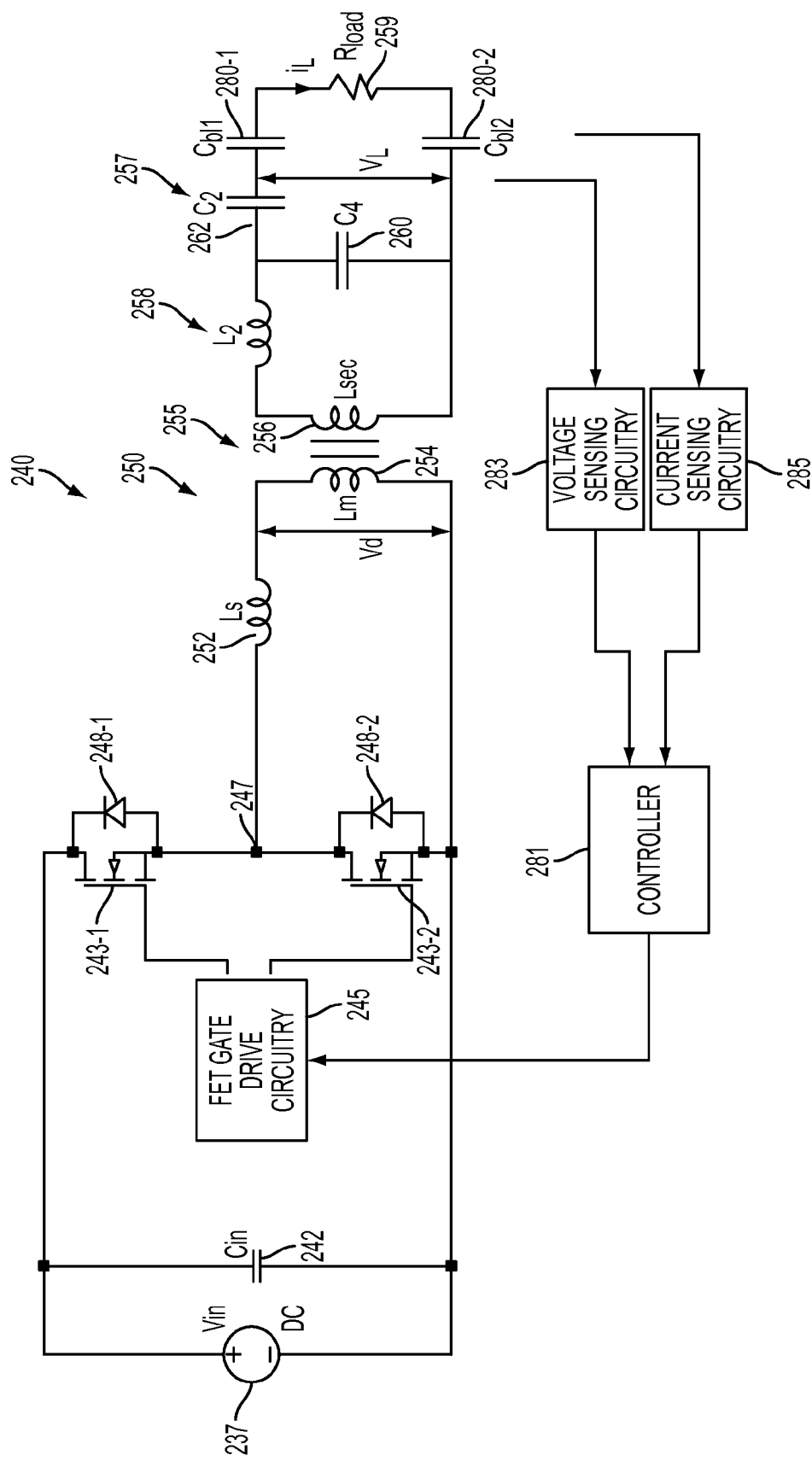
FIG. 8B shows one embodiment of an RF drive and control circuit.

The generator circuit 220 may be configured in any suitable manner. In some embodiments, the generator circuit comprises an RF drive and control circuit 240 and a controller circuit 282. FIG. 8B shows one embodiment of an RF drive and control circuit 240. FIG. 8B is a part schematic part block diagram illustrating the RF drive and control circuitry 240 used in this embodiment to generate and control the RF electrical energy supplied to the end effector 126. In this embodiment, the drive circuitry 240 is a resonant mode RF amplifier comprising a parallel resonant network on the RF amplifier output and the control circuitry operates to control the operating frequency of the drive signal so that it is maintained at the resonant frequency of the drive circuit, which in turn controls the amount of power supplied to the end effector 126. The way that this is achieved will become apparent from the following description.

As shown in FIG. 8B, the RF drive and control circuit 240 comprises the above described battery 237 are arranged to supply, in this example, about 0V and about 12V rails. An input capacitor ($C_{in}$) 242 is connected between the 0V and the 12V for providing a low source impedance. A pair of FET switches 243-1 and 243-2 (both of which are N-channel in this embodiment to reduce power losses) is connected in series between the 0V rail and the 12V rail. FET gate drive circuitry 245 is provided that generates two drive signals—one for driving each of the two FET's 243. The FET gate drive circuitry 245 generates drive signals that causes the upper FET (243-1) to be on when the lower FET (243-2) is off and vice versa. This causes the node 247 to be alternately connected to the 12V rail (when the FET 243-1 is switched on) and the 0V rail (when the FET 243-2 is switched on). FIG. 8B also shows the internal parasitic diodes 248-1 and 248-2 of the corresponding FET's 243, which conduct during any periods that the FET's 243 are open.

As shown in FIG. 8B, the node 247 is connected to an inductor-inductor resonant circuit 250 formed by inductor $L_s$ 252 and inductor $L_m$ 254. The FET gate driving circuitry 245 is arranged to generate drive signals at a drive frequency ($f_d$) that opens and crosses the FET switches 243 at the resonant frequency of the parallel resonant circuit 250. As a result of the resonant characteristic of the resonant circuit 250, the square wave voltage at node 247 will cause a substantially sinusoidal current at the drive frequency ($f_d$) to flow within the resonant circuit 250. As illustrated in FIG. 8B, the inductor $L_m$ 254 is the primary of a transformer 255, the secondary of which is formed by inductor $L_{sec}$ 256. The inductor $L_{sec}$ 256 of the transformer 255 secondary is connected to an inductor-capacitor-capacitor parallel resonant circuit 257 formed by inductor $L_2$ 258, capacitor $C_4$ 260, and capacitor $C_2$ 262. The transformer 255 up-converts the drive voltage ($V_d$) across the inductor $L_m$ 254 to the voltage that is applied to the output parallel resonant circuit 257. The load voltage ($V_L$) is output by the parallel resonant circuit 257 and is applied to the load (represented by the load resistance $R_{load}$ 259 in FIG. 8B) corresponding to the impedance of the forceps' jaws and any tissue or vessel gripped by the end effector 126. As shown in FIG. 8B, a pair of DC blocking capacitors $C_{b11}$ 280-1 and $C_{b12}$ 280-2 is provided to prevent any DC signal being applied to the load 259.

In one embodiment, the transformer 255 may be implemented with a Core Diameter (mm), Wire Diameter (mm), and Gap between secondary windings in accordance with the following specifications:

Core Diameter, D (mm)
D=19.9×10−3
Wire diameter, W (mm) for 22 AWG wire
W=7.366×10−4
Gap between secondary windings, in gap=0.125
G=gap/25.4

In this embodiment, the amount of electrical power supplied to the end effector 126 is controlled by varying the frequency of the switching signals used to switch the FET's 243. This works because the resonant circuit 250 acts as a frequency dependent (loss less) attenuator. The closer the drive signal is to the resonant frequency of the resonant circuit 250, the less the drive signal is attenuated. Similarly, as the frequency of the drive signal is moved away from the resonant frequency of the circuit 250, the more the drive signal is attenuated and so the power supplied to the load reduces. In this embodiment, the frequency of the switching signals generated by the FET gate drive circuitry 245 is controlled by a controller 281 based on a desired power to be delivered to the load 259 and measurements of the load voltage ($V_L$) and of the load current ($I_L$) obtained by conventional voltage sensing circuitry 283 and current sensing circuitry 285. The way that the controller 281 operates will be described in more detail below.

In one embodiment, the voltage sensing circuitry 283 and the current sensing circuitry 285 may be implemented with high bandwidth, high speed rail-to-rail amplifiers (e.g., LMH6643 by National Semiconductor). Such amplifiers, however, consume a relatively high current when they are operational. Accordingly, a power save circuit may be provided to reduce the supply voltage of the amplifiers when they are not being used in the voltage sensing circuitry 283 and the current sensing circuitry 285. In one-embodiment, a step-down regulator (e.g., LT1502 by Linear Technologies) may be employed by the power save circuit to reduce the supply voltage of the rail-to-rail amplifiers and thus extend the life of the battery 237.

Figure 8C:
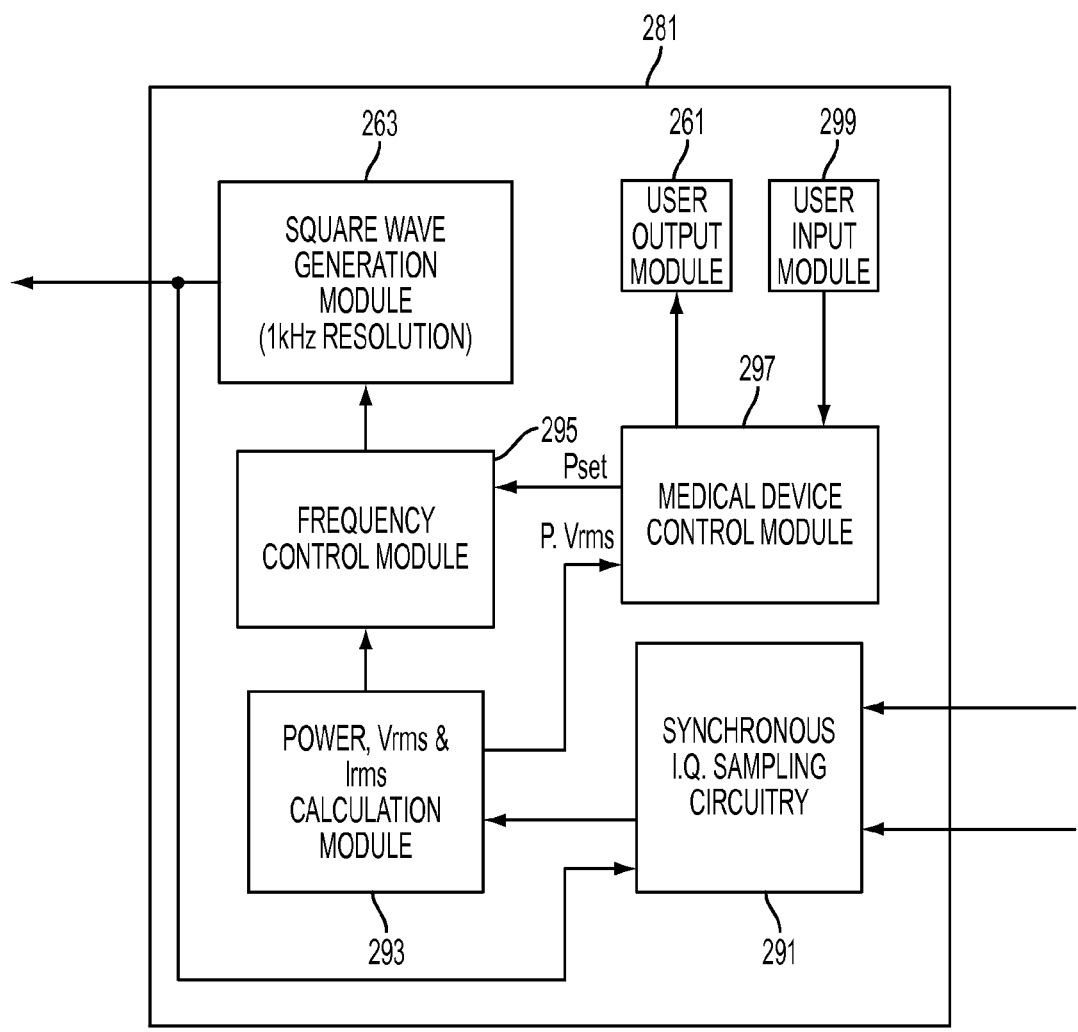
FIG. 8C shows one embodiment of the main components of a control circuit.

FIG. 8C shows the main components of the controller 281, according to one embodiment. In the embodiment illustrated in FIG. 8C, the controller 281 is a microprocessor based controller and so most of the components illustrated in FIG. 8c are software based components. Nevertheless, a hardware based controller 281 may be used instead such as, for example, a FPGA, ASIC, etc. As shown, the controller 281 includes synchronous I,Q sampling circuitry 291 that receives the sensed voltage and current signals from the sensing circuitry 283 and 285 and obtains corresponding samples which are passed to a power, $V_{rms}$ and $I_{rms}$, calculation module 293. The calculation module 293 uses the received samples to calculate the RMS voltage and RMS current applied to the load 259 (FIG. 8B; end effector 126 and tissue/vessel gripped thereby) and from them the power that is presently being supplied to the load 259. The determined values are then passed to a frequency control module 295 and a medical device control module 297. The medical device control module 297 uses the values to determine the present impedance of the load 259 and based on this determined impedance and a pre-defined algorithm, determines what set point power ($P_{set}$) should be applied to the frequency control module 295. The medical device control module 297 is in turn controlled by signals received from a user input module 299 that receives inputs from the user (for example pressing buttons 228 or activating the control levers 221 on the handle 212) and also controls output devices (lights, a display, speaker or the like) on the handle 212 via a user output module 261.

The frequency control module 295 uses the values obtained from the calculation module 293 and the power set point ($P_{set}$) obtained from the medical device control module 297 and predefined system limits (to be explained below), to determine whether or not to increase or decrease the applied frequency. The result of this decision is then passed to a square wave generation module 263 which, in this embodiment, increments or decrements the frequency of a square wave signal that it generates by 1 kHz, depending on the received decision. As those skilled in the art will appreciate, in an alternative embodiment, the frequency control module 295 may determine not only whether to increase or decrease the frequency, but also the amount of frequency change required. In this case, the square wave generation module 263 would generate the corresponding square wave signal with the desired frequency shift. In this embodiment, the square wave signal generated by the square wave generation module 263 is output to the FET gate drive circuitry 245, which amplifies the signal and then applies it to the FET 243-1. The FET gate drive circuitry 245 also inverts the signal applied to the FET 243-1 and applies the inverted signal to the FET 243-2.

The electrosurgical instrument 210 may comprise additional features as discussed with respect to the electrosurgical system 100 illustrated in FIGS. 1-6. Those skilled in the art will recognize that electrosurgical instrument 210 may include a rotation knob 148, an elongated shaft 114, and an end effector 126. These elements function in a substantially similar manner to that discussed above with respect to the electrosurgical system 100 illustrated in FIGS. 1-6. In one example embodiment, the cordless electrosurgical instrument 210 may include visual indicators 235. The visual indicators 235 may provide a visual indication signal to an operator. In one example embodiment, the visual indication signal may alert an operator that the device is on, or that the device is applying energy to the end effector. Those skilled in the art will recognize that the visual indicators 235 may be configured to provide information on multiple states of the device.

Various embodiments are directed to electrosurgical systems, such as 100 and 200 described above, that are capable of detecting short circuits between electrodes of an electrosurgical instrument. For example, it is desirable for a surgical system to distinguish between a short circuit and a low tissue impedance condition that occurs during tissue treatment. When a short circuit is encountered, it is typically desirable to halt the electrosurgical signal to allow the clinician to reposition the electrodes and/or remove the clip, staple or other non-tissue component causing the short. On the other hand, when a low tissue impedance condition is encountered, it is typically desirable to complete treatment.

Many electrosurgical systems detect short circuits by monitoring the impedance between the system electrodes, with a low impedance indicating a short. In various embodiments, a short circuit presents as a current sink, with minimal changes in voltage. This may be detected, for example, by monitoring impedance. For example, when impedance below a threshold impedance is detected and persists for a threshold time period, a short circuit may be indicated. The generator may cease providing the electrosurgical signal and give an audible and/or visual indication to the clinician to change the electrode placement and/or remove the short. Monitoring impedance between the electrodes alone, however, makes it difficult to distinguish short circuits from ordinary low tissue impedance conditions.

Figure 9:
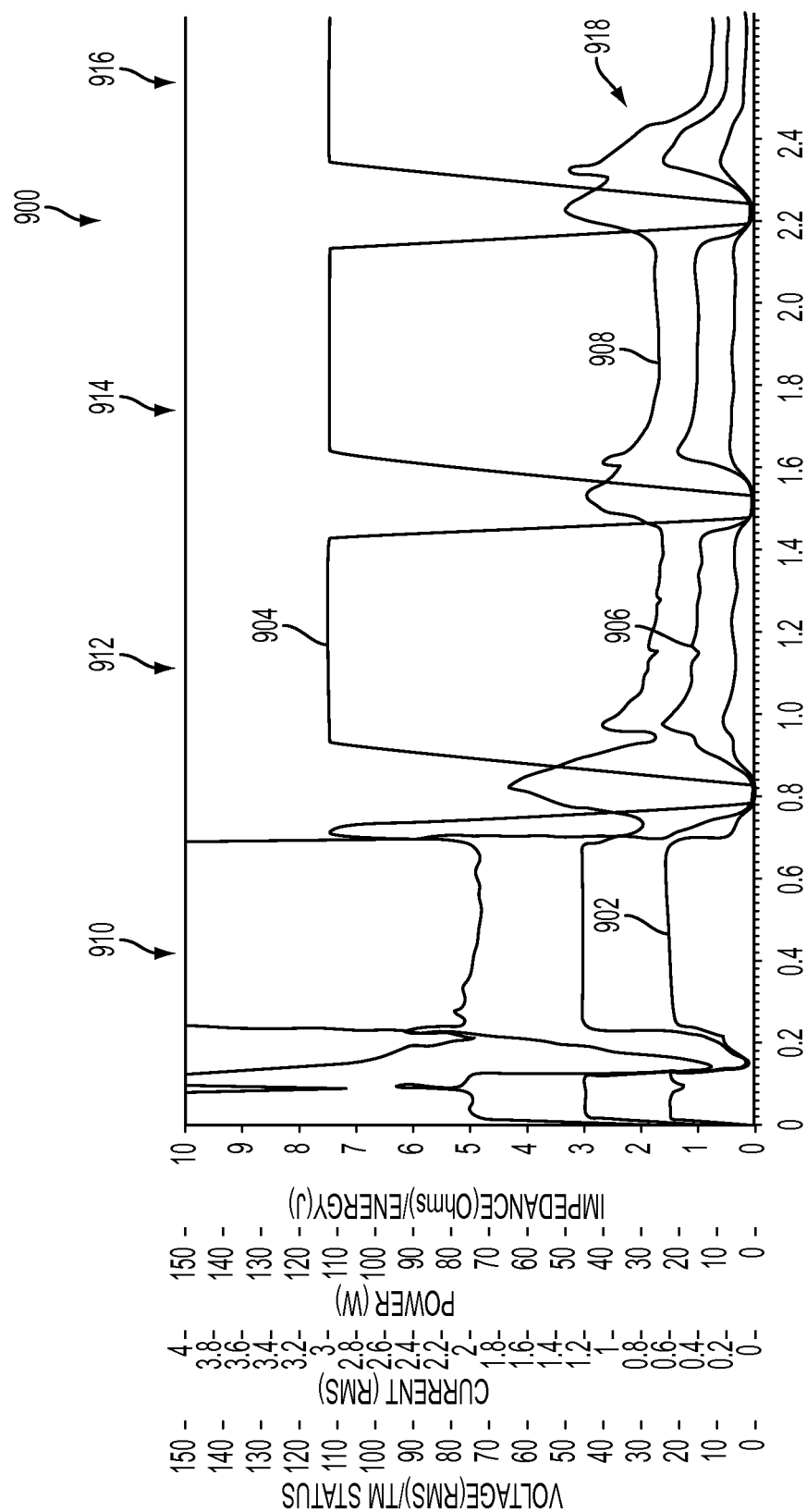
FIG. 9 is a chart showing the voltage, current, power and impedance of an example electrosurgical signal provided to human tissue and exhibiting a low tissue impedance condition.
Figure 10:
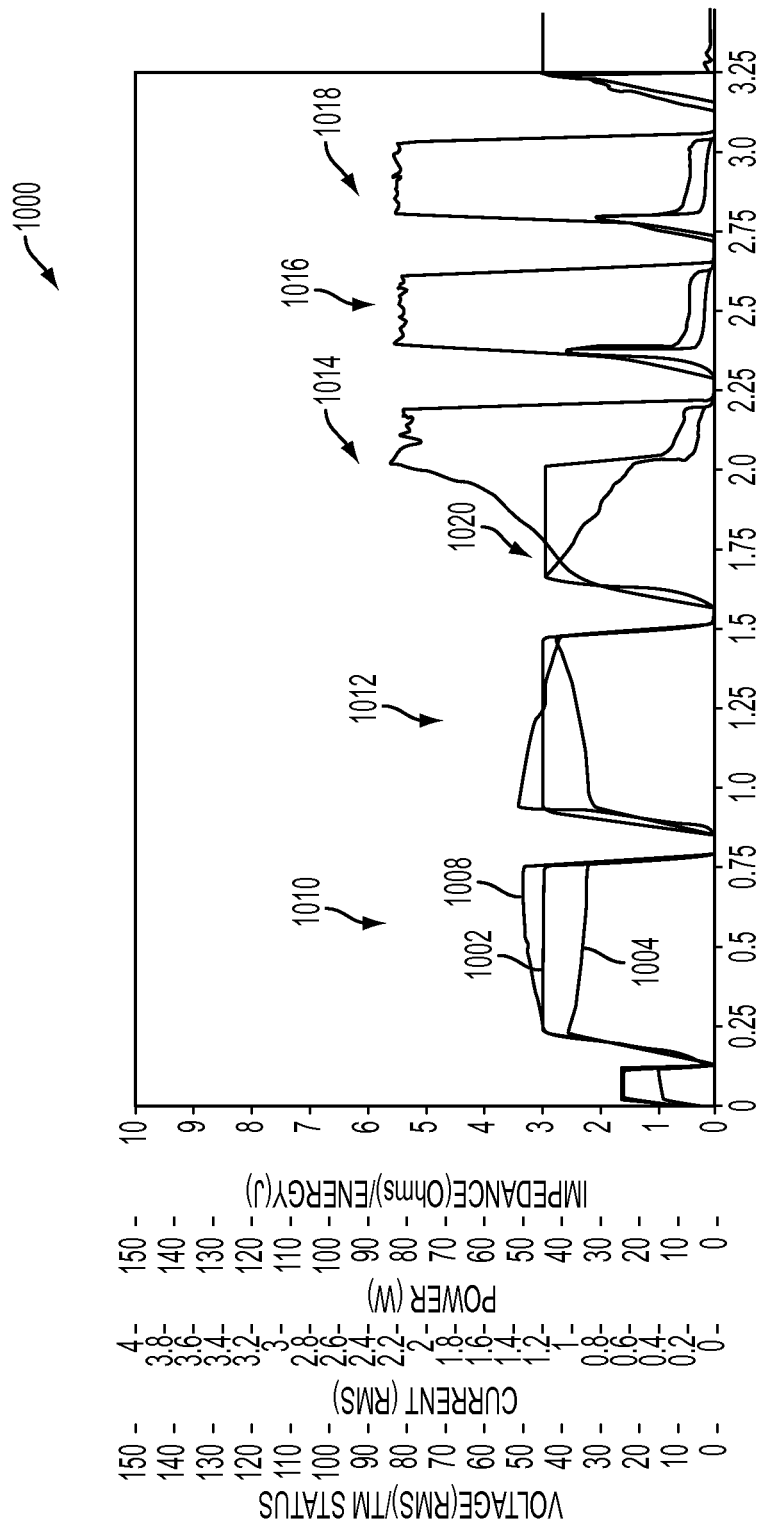
FIG. 10 is a chart showing voltage, current, power and impedance of an example electrosurgical signal provided to human tissue and exhibiting a short circuit.

FIG. 9 is a chart 900 showing the voltage 902, current 904, power 906 and impedance 908 of an example electrosurgical signal provided to human tissue and exhibiting a low tissue impedance condition. The electrosurgical signal comprises a plurality of pulses 910, 912, 914, 916. A low tissue impedance condition is illustrated at 918. Here, the impedance (e.g., the impedance between the instrument electrodes in response to the signal) drops well below two ohms with no short circuit present. FIG. 10 is a chart 1000 showing voltage 1002, current 1004, power and impedance 1008 of an example electrosurgical signal provided to human tissue and exhibiting a short circuit. The signal provided in FIG. 10 is also formed of a series of pulses 1010, 1012, 1014, 1016, 1018. A short circuit occurs at 1020 when the electrodes encounter a line of conducting staples. As illustrated, current 1004 spikes while impedance 1008 and voltage 1002 drop sharply.

It has been determined that during a low tissue impedance condition, the impedance level between the electrodes tends to change slightly at equivalent points of successive pulses. For example, referring to FIG. 9, the impedance 908 at the beginning of the pulse 914 is greater than the impedance 908 at the beginning of the pulse 916. Also, as indicated in FIG. 9, the tissue impedance tends to follow a common "bathtub" pattern of rising near the beginning of a pulse, falling in the middle of the pulse, and then rising again near the end of the pulse. In contrast, when a short circuit is encountered, as illustrated in FIG. 10, the "bathtub" pattern of impedance is not encountered. Further, when a short circuit is encountered, impedance does not typically vary from pulse to pulse.

Figure 11:
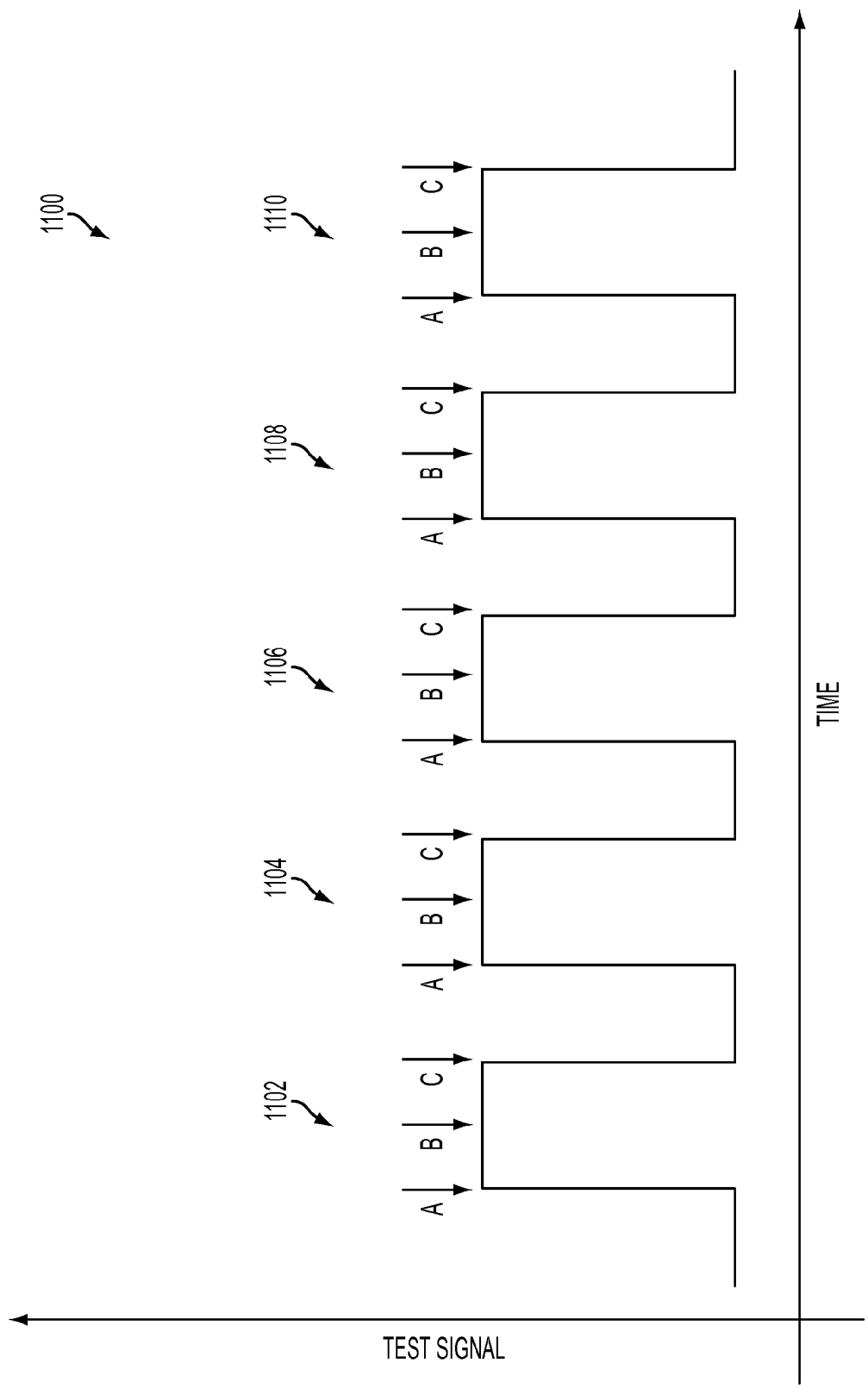
FIG. 11 is a chart illustrating one example embodiment of an electrosurgical signal comprising a plurality of pulses.

In various embodiments, these properties may be exploited to detect short circuits by comparing impedance values at different positions within a pulse. For example, FIG. 11 is a chart illustrating one example embodiment of an electrosurgical signal 1100 comprising a series of pulses 1102, 1104, 1106, 1108, 1110. The signal 1100, corresponding to the vertical axis, represents a current and/or voltage without considering load effects. Each of the pulses 1102 can be divided into a plurality of positions, indicated in FIG. 11 by A, B and C. Although three positions are shown for each pulse 1102, 1104, 1106, 1108, 1110, it will be appreciated that any suitable number of regions may be utilized. Also, for example, positions, such as A and C, that are adjacent to a rising or falling edge of the signal 1100 may be taken far enough away from the rising or falling edge so as to avoid capturing transient effects. Although five pulses are shown in FIG. 11, it will be appreciated that any suitable number of pulses may be used.

In practice, the surgical system may capture impedance readings at a plurality of points within each pulse. The surgical system (e.g., the generator 120, 220 or control circuit 125, 281, thereof) may detect a short circuit by comparing impedance values taken among the points. Various patterns may indicate a short circuit or simply a low tissue impedance condition. For example, if the impedance at position A is higher for a given pulse 1102, 1104, 1106, 1108, 1110 than it was a position A for the immediately preceding pulse, then the surgical system may conclude that it is experiencing a low tissue impedance condition rather than a short circuit. Also, for example, if the impedance at common positions among successive pulsing is changing, rather than constant, it may indicate a low tissue impedance condition rather than a short circuit.

Figure 12:
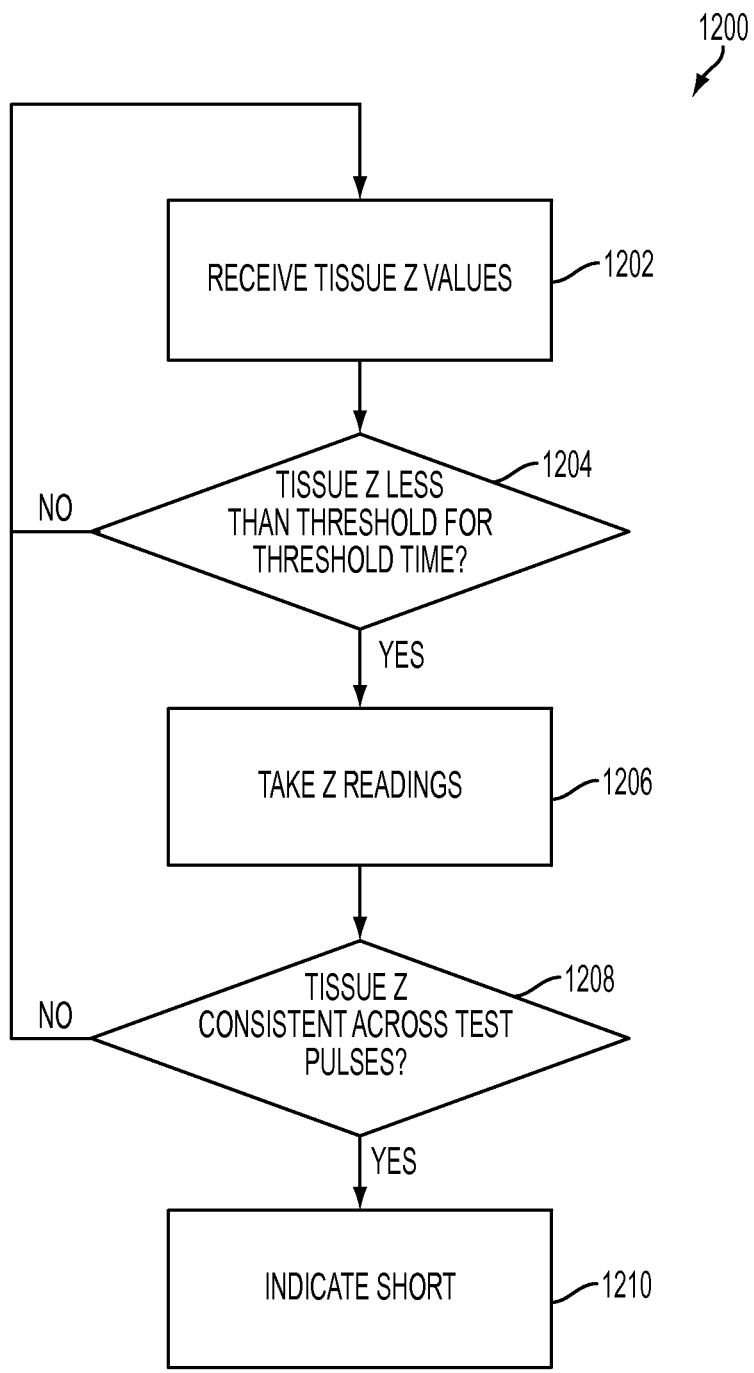
FIG. 12 is a flow chart illustrating one embodiment of a process flow for detecting short circuits based on inter-pulse impedance comparisons.

Impedance readings, as described, may be used in this manner to detect short circuits in any suitable manner. For example, FIG. 12 is a flow chart illustrating one embodiment of a process flow 1200 for detecting short circuits based on inter-pulse impedance comparisons. The process flow 1200 may be executed, for example, by a generator, such as 120, 220 and/or a control circuit thereof, such as 125, 281, thereof. At 1202, the electrosurgical system may receive impedance (or "Z") values based on an electrosurgical signal provided to the electrodes of the electrosurgical system. The electrosurgical system, in some embodiments, may first determine when the impedance drops below a threshold impedance (e.g. 0.5Ω-4Ω) for a threshold period of time (e.g., 50 ms-500 ms). If this condition is not detected at 1204, then the electrosurgical system may continue to provide the electrosurgical signal at 1202, for example, according to a predetermined algorithm. If the condition is detected at 1204, then the electrosurgical system may take additional impedance readings at 1206. The additional readings may be taken, for example, at predetermined pulse positions (similar to A, B, and C of FIG. 11). In some embodiments, the additional readings of 1206 may be taken as the original electrosurgical signal continues to be applied. Also, in some embodiments, the original electrosurgical signal may be paused at 1206 while a discrimination mode signal is provided for testing the condition of tissue between the electrodes. For example, the discrimination mode signal may comprise a series of discrete pulses (e.g., five pulses). In some embodiments, the impedance of the electrosurgical signal may be determined utilizing Ohm's law based on measured voltage and current.

Upon taking the impedance readings at 1206, the electrosurgical system may determine, at 1208, whether the impedance readings are consistent across pulses. If the readings are consistent, it may indicate a short circuit. This may cause the electrosurgical system to indicate the short at 1210, for example, by terminating the electrosurgical system and/or providing audible and/or visual feedback to the clinician. If the readings are not consistent, it may indicate a simple low tissue impedance condition. In response, the electrosurgical system may continue to provide the electrosurgical system, for example, according to a predefined algorithm. In some embodiments, upon detection of a simple low tissue impedance condition, the electrosurgical system may suspend the impedance thresholds of 1204 for a predetermined number of pulses and/or a predetermined time period in order to allow the tissue impedance to recover before again testing for a short circuit.

The electrosurgical system may determine whether the impedance readings are consistent in any suitable way using any suitable set of conditions. An example set of conditions is provided in TABLE 1 below, assuming that the impedance readings of 1206 are taken over five pulses. It will be appreciated that the readings of 1206 may be taken over more or fewer than five pulses. Also, although the conditions below indicate equality, it will be appreciated that the conditions may be true when the indicated values are substantially equal (e.g., within a threshold amount of one another.)

TABLE 1

| Condition | Inference |
| --- | --- |
| 1102A = 1104A | Short circuit |
| 1102B = 1104B | Short circuit |
| 1102C = 1104C | Short circuit |
| 1104A = 1106A | Short circuit |
| 1104B = 1106B | Short circuit |
| 1104C = 1106C | Short circuit |
| 1106A = 1108A | Short circuit |
| 1106B = 1108B | Short circuit |
| 1106C = 1108C | Short circuit |
| 1108A = 1110A | Short circuit |
| 1108B = 1110B | Short circuit |
| 1108C = 1110C | Short circuit |
| Average of 1102A, B, C = Average of 1104A, B, C | Short circuit |
| Average of 1104A, B, C = Average of 1106A, B, C | Short circuit |
| Average of 1106A, B, C = Average of 1108A, B, C | Short circuit |
| Average of 1108A, B, C = Average of 1110A, B, C | Short circuit |

It will be appreciated that other suitable permutations of conditions similar to those shown in TABLE 1 may be measured and utilized. Any suitable method for evaluating the conditions of TABLE 1 (or other suitable conditions) may be utilized. For example, a voting method may be used. When a threshold number of the conditions are true, then the electrosurgical system may indicate that a short circuit is present.

Figure 13:
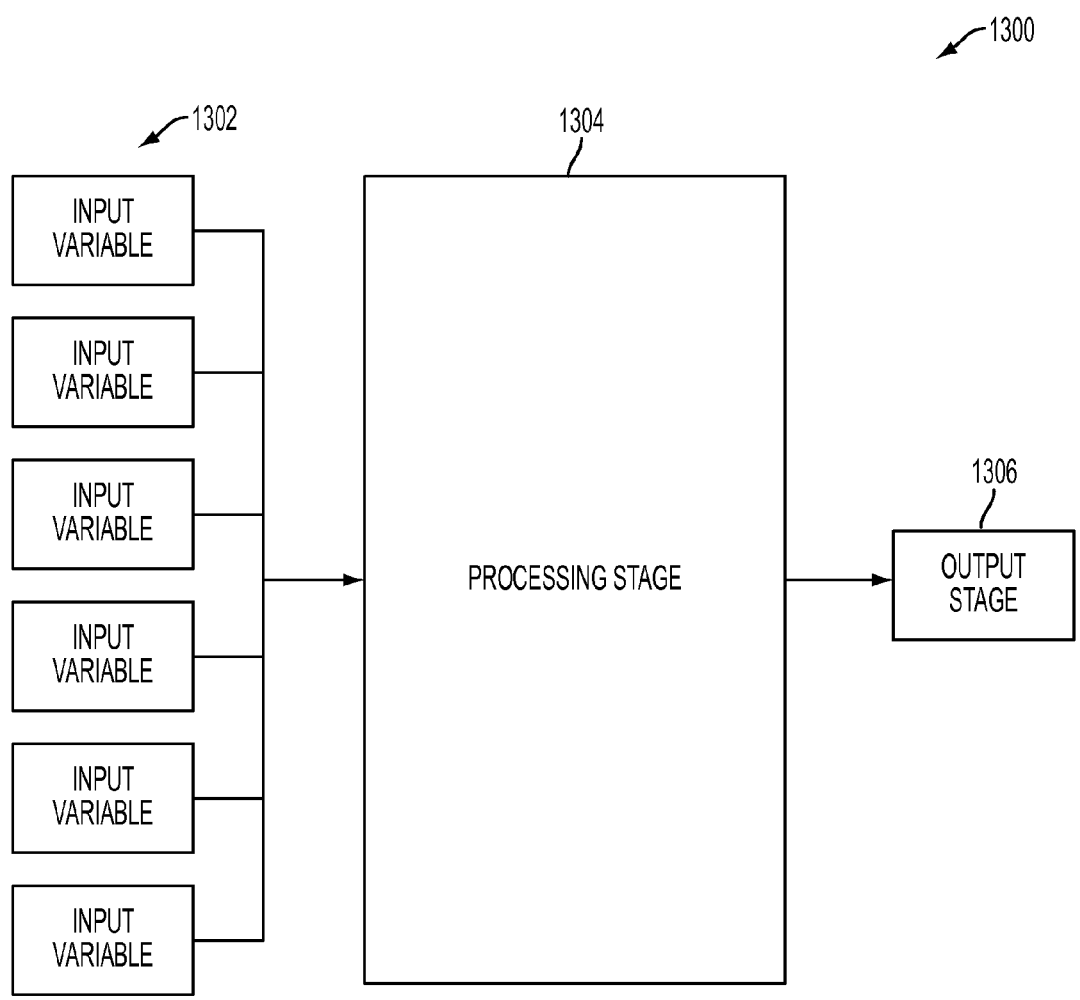
FIG. 13 is a workflow showing one embodiment of a fuzzy logic algorithm that may be utilized according to various embodiments to detect a short circuit.

According to various embodiments, a fuzzy logic algorithm may be utilized to detect short circuits. FIG. 13 is a workflow showing one embodiment of a fuzzy logic algorithm 1300 that may be utilized according to various embodiments to detect a short circuit. The algorithm 1300 may receive as input various input variables 1302. The input variables may be any variable or condition that tends to indicate the presence or absence of a short circuit. For example, the input variables may comprise the instantaneous impedance between the electrodes, any of the conditions indicated above in TABLE 1, etc. In some embodiments, the input variables 1302 may include the results of other calculations, such as any of the other calculations for detecting a short circuit described herein. A processing stage 1304 may be utilized to covert the input variables 1302 into an output stage 1306 indicating the presence or absence of a short circuit. The processing stage 1304 may consider the input variables 1302 according to a set of "if-then" rules. A cut-off rule or set of rules may indicate that a short circuit and may be applied when the last tissue state measured by the processing stage 1304 indicated no short circuit. Once a short circuit is detected at the processing stage (e.g., once a short circuit state is assumed), the processing stage 1304 may apply an intermediate rule or set of rules. The intermediate rules may be less indicative of a short circuit than the cut-off rules. Taking an example from TABLE 1 above, a cut-off rule may be expressed as (A) below:

(A) IF: 1102A is within 0.25 ohms of 1104A; THEN indicate short circuit;
   a. ELSE: Do not indicate a short circuit Once a short circuit is indicated, however, intermediate values may be used, for example, as indicated by rules (C) and (D) below:

(B) IF: Short circuit indicated; and 1102A is within 0.5 ohms of 1104A; THEN continue to indicate a short circuit
   a. ELSE—Do not indicate a short circuit In another example, a cut-off rule may be expressed by (C) below:

(C) IF: Impedance between the electrodes is less than 4Ω for 300 mS; THEN indicate a short circuit;
   a. ELSE: Do not indicate a short circuit A corresponding intermediate rule may be expressed as (D) below:

(D) IF: Short circuit indicated; AND impedance between the electrodes is less than 8Ω for 100 mS; THEN—continue to indicate a short circuit
   a. ELSE—Do not indicate a short circuit.

In some embodiments, the fuzzy logic algorithm may be implemented in stages. For example, a fuzzy logic cut-off or intermediate rule may be applied for a number of input variables or conditions (e.g., the conditions set forth in TABLE 1). The results may be combined in one or more additional stages of fuzzy logic rules to determine the value of the output stage 1306.

Figure 14:
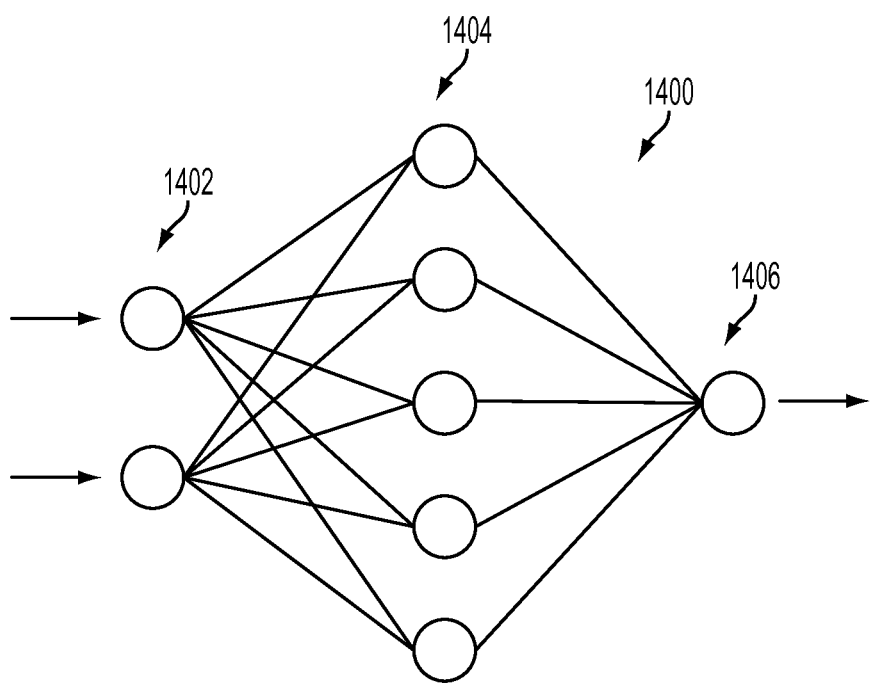
FIG. 14 is a diagram showing an example neural network for detecting short circuit conditions.

In various embodiments, the electrosurgical system may utilize a neural network algorithm to detect short circuit conditions. For example, a neural network may be effective for recognizing complex patterns in input variables, which may make them well suited to detect short circuit conditions. FIG. 14 is a diagram showing an example neural network 1400 for detecting short circuit conditions. The neural network 1400 comprises a group of interconnected nodes 1402, 1404, 1406 referred to as neurons. Connections between different neurons indicate how data is passed through the network. Input neurons 1402 are assigned values from input data (e.g., various parameters of the electrosurgical instrument, the electrosurgical signal, etc.). In various forms, the input variables are scaled to values between zero and one. The values of the input neurons 1402 (e.g., the input variables) are then utilized to calculate values of various hidden neurons 1404, which are, in turn, used to find the value of one or more output neurons 1406. The value of the output neuron 1406 may indicate, or not indicate, a short circuit condition. In practice, the number of respective input nodes 1402, hidden nodes 1404 and output nodes 1406 may vary, sometimes considerably, from what is shown in FIG. 14. In various forms, a neural network is operated on a data cycle. During each cycle, input values are provided to the input neurons 1402 and output values are taken at the output node 1406.

Neural networks may be fully connected, as shown in FIG. 14, meaning that each input neuron 1402 is connected to each hidden neuron 1404. Some forms may utilize a neural network that is not fully connected. For example not all of the input nodes may be connected to each hidden neuron 1404. Values for the hidden nodes 1404 may be determined according to an activation function. In various forms, the outputs of the activation function range from 0 to 1. For example, the output function may be selected to generate outputs between 0 and 1 or, in some forms, results of the output function may be scaled. In some forms, it is advantageous to select functions that are continuous and differentiable. This may facilitate training of the neural network. For example, back-propagation training utilizing a gradient method may require computing partial derivatives of the output function, which may be simplified when the optimization functions are continuous and differentiable. One example of such a function that may be utilized as the activation functions is the sigmoid function, as indicated by Equation (1) below:

$$x = \omega_1 \xi_1 + \omega_{22} \xi_2 + \omega_3 \xi_3 + \ldots + \theta \quad (1)$$

In Equation (1), ξ corresponds to the values of the input neurons, ω corresponds to the weights given to each input, θ corresponds to a constant. When the neural network is fully connected, the values of all input neurons are passed to all hidden neurons, meaning the activation function for each hidden neuron will include a ξ term corresponding to each input node. The weights given to each input (ω) may be unique for each hidden neuron and/or each input value. The constant θ may also be unique for each hidden neuron 1404. The results at each node may be given by Equations (2) and (3) below:

$$\sigma(s) = \frac{1}{1+e^{-x}} \quad (2)$$

Figure 15:
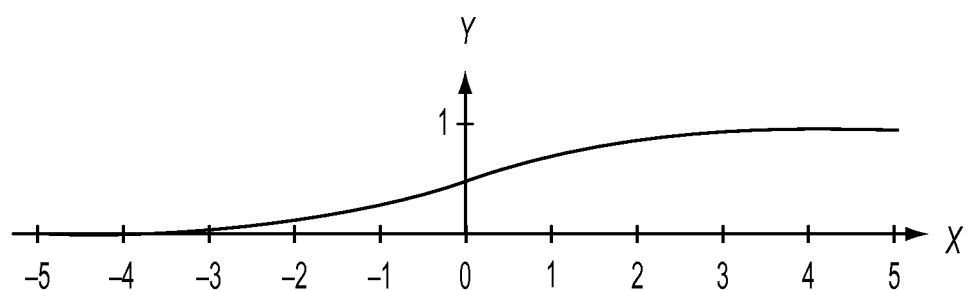
FIGS. 15 and 16 are plots of example implementations of equations for indicating results at the nodes of the neural network of FIG. 14.

FIG. 15 is a plot of one example implementation of Equation (2), demonstrating that the function is continuous and differentiable.

$$O = \sigma(x) \quad (3)$$

Figure 16:
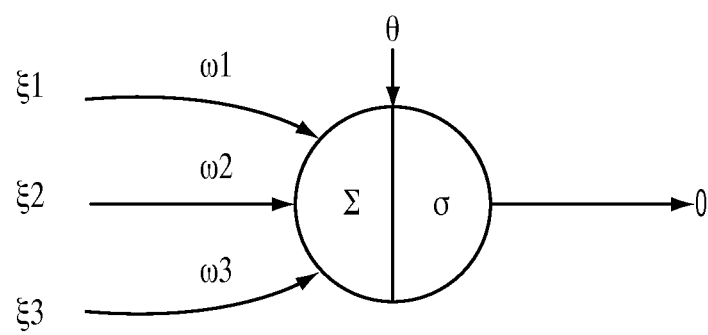

The output of the sigmoid function is illustrated in FIG. 16. For example, the output (O) may be calculated from the weighted sum of the input neurons plus theta (e.g., Equation (1)) applied to Equation (2).

In various forms, each hidden neuron has I inputs, which is equal to the number of inputs to the neural network. If there are J hidden neurons 1404, then there are I×J unique values for omega (ω) and J unique values for theta (θ). In some forms, the output neuron(s) 1406 may utilize the same activation equation. Accordingly, there may be J×K unique omega (ω) values connecting the hidden neurons 1404 to the output neuron 1406, where K is the number of output neurons, and K unique values of theta (θ) for the output node(s) 1406.

The output of the neural network may indicate the truth or falsity of a condition set comprising one or more conditions of the electrosurgical instrument, tissue acted upon by the surgical instrument, or some combination thereof. For example, a neural network may be used to model the presence or absence of a short circuit. Any suitable number or type of neurons 1402, 1404, 1406 may be used. For example, the neural network 1400 may comprise twelve input neurons 1402, (I=12), four hidden neurons (J=4), and one output neuron (K=1). The data cycle may be 10 milliseconds. Accordingly, values for the 12 inputs may be fed into the network 1400, and results calculated, every 10 milliseconds.

Input variables (e.g., variables corresponding to the input nodes 1402) may comprise any variables that could, in some circumstances, affect the value of an output node 1406. For example, input variables may include descriptors of the impedance between the first and second electrodes such as, for example, the impedance between the electrodes measured at any point of the various pulses, averages of the impedance across a pulse; averages of the impedance from one pulse to another, any of the conditions indicated at TABLE 1 above, including permutations thereof, etc. It will be appreciated that the input variables described herein may also be used any other suitable type of trainable model including, for example, genetic algorithm models, classification tree algorithm models, recursive Bayesian models, etc.

It will be appreciated that the neural network 1400 may utilize any of the input variables described herein above. In some forms, the neural network 1400 may be evaluated utilizing matrix algebra. For example, four matrices maybe used. A 1×I input matrix (O_i) may include (e.g., scaled) values for the I input neurons. An I×J hidden neuron omega matrix (W_ij) comprises omega (ω) values used to calculate values of hidden neurons 1404. A J×K output neuron omega matrix (W_jk) comprises omega (ω) values used to calculate the values of output neuron or neurons 1406. A 1×J hidden neuron constant matrix (O_j) comprises constant θ values for the hidden neurons 1404. A 1×K output neuron constant matrix (O_k) comprises constant θ values for the output neuron(s) 1406. For any given cycle, the output of the neural network may be calculated by evaluating the matrices as indicated by Equations (4)-(7) below:

$$x\_j = O\_i * W\_ij + O\_j \quad (4)$$

The result of Equation (4), x_j, may be the weighted sums of the input neuron values for each hidden neuron 1404. Matrix x_j may be processed element-by-element through an equation, such as Equation (5) below, resulting in a matrix of equal size, O_j.

$$O\_j = (1 + \exp(-x\_j))\textasciicircum(-1*Z) \quad (5)$$

The result of Equation (5), O_j may be the values for each of the hidden neurons 1404. In Equation (12), Z corresponds to an matrix of ones having a size K×J.

$$x\_k = O\_j * W\_jk + O\_k \quad (6)$$

The result of Equation (6), x_k, may be the weighted sums of the hidden neuron values for each output neuron 1406. Matrix x_k is processed element-by-element through an equation, e.g., Equation (7), resulting in a matrix of equal size, O_k.

$$O\_k = (1 + \exp(-x\_k))\textasciicircum(-1*Z1) \quad (7)$$

The result of Equation (7), O_k, may be the output of the neural network. In Equation (6), Z1 may be a matrix of ones having a size K×1.

Figure 17:
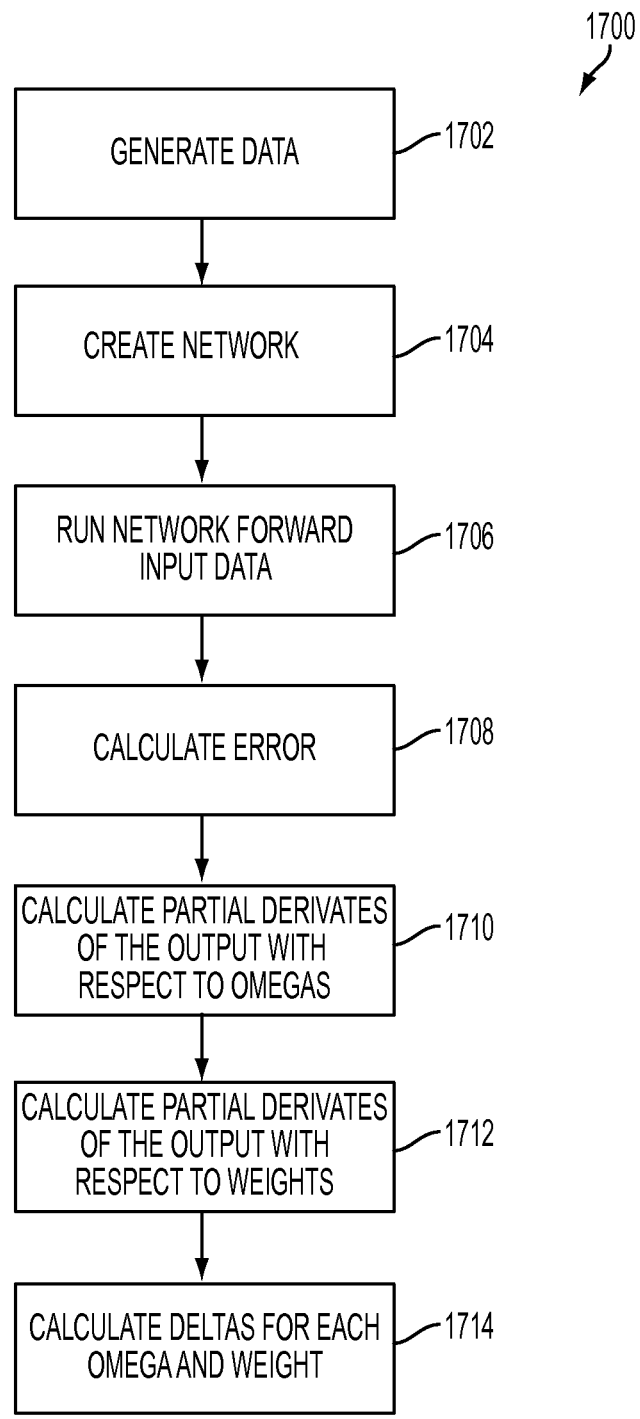
FIG. 17 is a logic flow diagram of one form of an algorithm for training a neural network, such as the neural network of FIG. 14, utilizing back-propagation.

The neural network may be trained in any suitable manner. For example, in some forms, the neural network may be trained utilizing back-propagation. During back-propagation training, the data flow of the neural network is reversed. For example, values for error versus actual output are used to modify individual weight and constant parameters. FIG. 17 is a logic flow diagram of one form of an algorithm 1700 for training a neural network, such as the neural network 1400, utilizing back-propagation. At 1702, relevant data sets may be generated. In some forms, separate data sets are generated for training and testing to ensure that actual pattern recognition is taking place instead of the network merely learning the data files being used for training. Each data set may comprise, for example, all of the necessary inputs. Each data set may also comprise actual values describing the state of the instrument and/or tissue corresponding to each set of input values, which represent the value modeled by the neural network. For example, in some forms, the actual values may comprise impedance data or other electrosurgical instrument descriptors, where each data set representing a set of input conditions is associated with an indication of whether a short circuit accompanied the input conditions. Neural networks trained in this manner may provide an output indicating whether a short circuit is present.

At 1704, the neural network may be created and trained. For example, the values for the weights and constants of the various neurons 1404, 1406 maybe randomly initialized (e.g., utilizing the MATLAB "rand" function, which generates a uniform distribution). In some forms, a value range of −2.5 to 2.5 may be utilized as these values tend to result in outputs in the range of 0-1 when processed by a sigmoid activation function. At 1706, the network 1400 may be run forward on the input data to generate a predicted output (or outputs if there are multiple output nodes). At 1708, an error may be calculated. The error is a difference between the predicted output from 1706 and the actual value of the tissue or instrument property, as described herein. In various forms, the output or outputs may be denoted as binary numbers where one (1) corresponds to the existence or truth of the condition and zero (0) corresponds to the non-existence or falsity of the condition. For example, when the condition is a short circuit, the output should be one (1) when a short circuit is present and zero (0) when no short circuit is present. In some forms, the condition may be considered true when the output of the neural network 1400 exceeds a threshold value (e.g., 0.85).

At 1710, the weights for each node are evaluated. For example, for each weight a partial derivative is found of the output or error (E) with respect to the weight (omega (ω)). This may be represented as $\delta E / \delta \, \omega_{ij}$ for connections between the input layer 1402 and the hidden layer 1404 and as $\delta E / \delta \, \omega_{jk}$ for connections between the hidden layer 1404 and the output layer 1406. At 1712, the constants for each node are evaluated. For example, for each constant, a partial derivative is found of the output or error (E) with respect to the constant θ. This may be represented as $\delta E / \delta \, \theta_i$ for connections between the input layer 1402 and the hidden layer 1404 and to $\delta E / \delta \, \theta_j$ for connections between the hidden layer 1404 and output layer 1406. At 1714, deltas may be calculated for each weight and constant. The deltas may found by multiplying each partial derivative by a gradient constant, η. In some forms, a value of 0.1 may be used for ii. The deltas may then be added to the original values of each weight and constant. Actions 1706, 1708, 1710, 1712, and 1714 may be repeated for subsequent cycles of the input data. In some form, the network 1400, once trained, may be tested. For example, the network 1400 may be tested, as described herein, on a testing data set distinct from the training data set. In various forms, a neural network or other multi-variable model may be pre-trained. Resulting model parameters (e.g., network configuration, values for weights and constants, etc.) may be determined and stored at a generator and/or instrument. The values may be utilized to execute the model during use.

It will be appreciated that various other signal processing and/or machine learning techniques may be used detect a short-circuit condition. Examples include naïve Bayes methods, support vector machine methods, decision tree methods, random forest methods, linear regression, adaptive filtering, etc. Many of these methods rely on common feature selection techniques including, but not limited to, mutual information and singular value decomposition. Some of these methods may also rely on common model selection techniques, which include, Akaike Information Criterea (AIC) or Bayesian information criteria. Some of these methods may also utilize metaheuristic concepts for searching a large parameter space, such as (and not limited to) simulated annealing.

Figure 18:
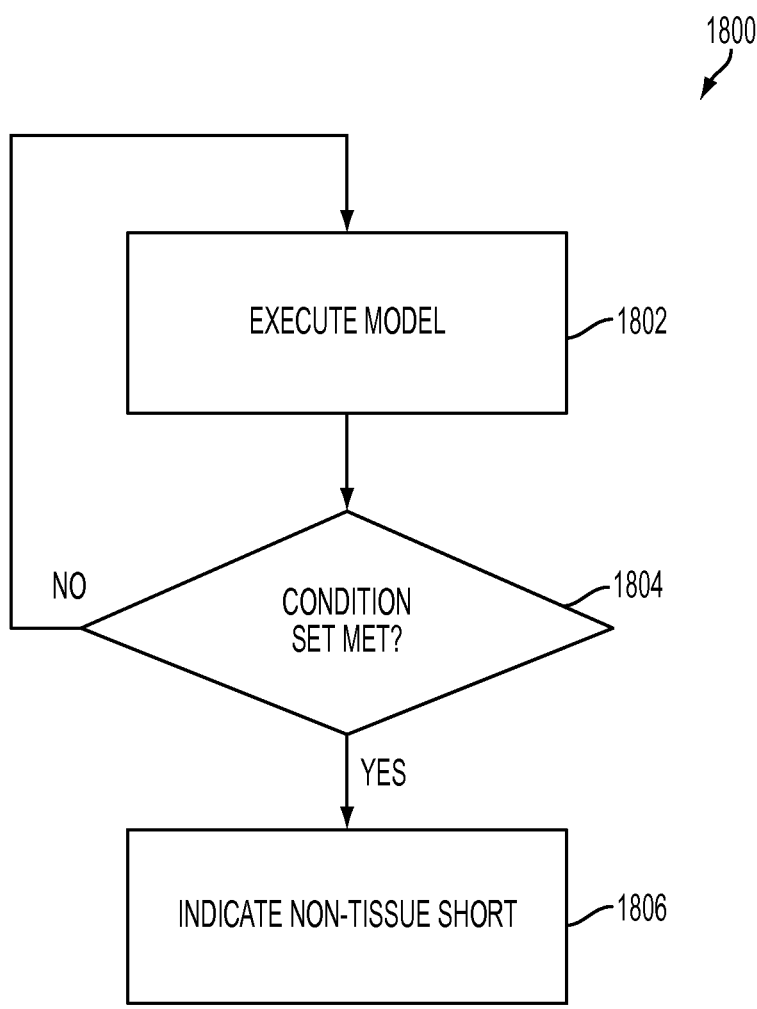
FIG. 18 is a logic flow diagram of one form of an algorithm for detecting a short circuit condition for an electrosurgical instrument utilizing a multi-variable model, such as the neural network described herein.

FIG. 18 is a logic flow diagram of one form of an algorithm 1800 for detecting a short circuit condition for an electrosurgical instrument utilizing a multi-variable model, such as the neural network 1400 described herein. As with the other instrument control algorithms described herein, the algorithm 1800 is described as being executed by a generator, such as generator 120, 220 described herein. Also, although a neural network is described herein, it will be appreciated that the algorithm 1800 may be executed utilizing any suitable type of model including, for example, genetic algorithm models, classification tree algorithm models, recursive Bayesian models, etc. At 1802, the electrosurgical system may execute the multi-variable model. Executing the multi-variable model may comprise providing input values to the model, processing the input values, and generating an output. For example, a process for executing an example neural network is described herein above in conjunction with Equations (4)-(7). At 1804, the generator may determine whether the modeled condition set is met. In the example above, this may involve determining whether a short circuit condition is present. If not, the model may continue to execute at 1802. If so, the short circuit condition may be indicated at 1806. For example, the electrosurgical instrument may cease the electrosurgical signal, provide visual and/or audible indications of the short circuit to the clinician, etc.

Figure 19:
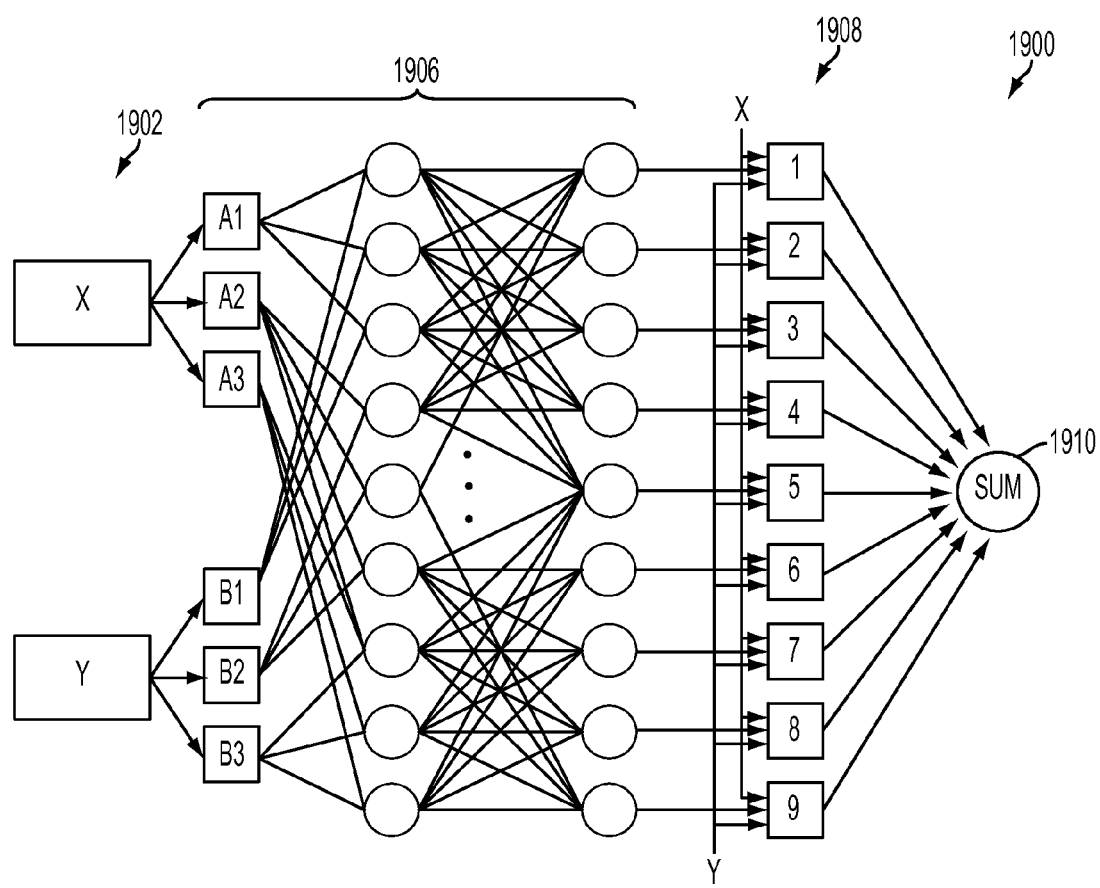
FIG. 19 is a workflow showing one embodiment of a neuro-fuzzy algorithm that may be utilized according to various embodiments to detect a short circuit.

According to various embodiments, the electrosurgical system may utilize a neuro-fuzzy algorithm to detect short circuits. FIG. 19 is a workflow showing one embodiment of a neuro-fuzzy algorithm 1900 that may be utilized according to various embodiments to detect a short circuit. A neuro-fuzzy algorithm may be based on neural networking and reinforced learning techniques. Such an algorithm may be referred to as an "Adaptive Neuro-Fuzzy Inference System" and may utilize Sugeno and Tsukamoto fuzzy models. These models are based on the number of inputs and can be multiple orders, with a series of rules and may also utilize back-propagation to train the network. For example, the algorithm 1900 may utilize output equations 1908 that are functions of the different inputs 1902 and layers 1906. This can result in multiple layers 1906 between in the inputs 1902 and the outputs 1910. This may be different than the neural network 1400 described herein above.

Depending on the nature of the inputs, different sets of statistical relationships may be used for conditioning of the signal. Example statistical relationships that may be used in some embodiments include a bell function, a Gaussian distribution, a trapezoidal distribution, etc. It will be appreciated that a statistical relationship or relationships may be selected to best match the inputs 1902 and learned outputs 1910. The selected statistical relationship or relationships are incorporated into one or more of the layers 1906 in the algorithm 1900. Due to the complexity of the "layers" 1906, some embodiments of the algorithm 1900 do not require that each layer be a function of all the layers before/after it. Layers that have multiple inputs but lead directly into a single layer (instead of nodes in a layer), may be used to determine firing strength, then a second set of calculations 1908 takes place. This final step then leads into a summation (single node) 1910, which is the final layer.

In some embodiments, the algorithm 1900 may be trained utilizing back propagation, for example, as described herein. Back propagation may be implemented utilizing various modes including, for example, batch mode and/or pattern mode. A pattern mode may require less storage when updating parameters in back propagation, however, a batch mode may result in better estimates of the calculated gradients. Both pattern and batch modes may rely on learning-rate parameters to be small.

Another obstacle to detecting short circuits is a regulatory requirement that a direct current (DC) blocking capacitor be used to prevent the transmission of a direct current voltage directly to the patient. For example, the International Electrotechnical Commission (IEC) regulation IEC60601-2-2 requires that a DC blocking capacitor of 47 nanofarads (nF) be placed in series with the electrosurgical signal to prevent transmission of a DC signal directly to the patient. The impedance of the blocking capacitor, therefore, is placed in series with the load, adding an impedance of: $-j\omega C$, where j is the square root of $-1$, co is the frequency of the electrosurgical signal in radians, or 2 it multipled by the frequency in Hertz, and C is the capacitance in Farads. The total impedance presented to the generator, then may be expressed as:

$$\text{Total Impedance} = \text{Impedance between electrodes} - j\omega k \quad (8)$$

For a 47 nF capacitor, the imaginary component comes to an impedance of $-j6.77\Omega$ at an electrosurgical signal frequency of 500 kHz. This makes it difficult to use a low cost output measurement circuit, such as a peak detection circuit, to measure the output phasor. For example, lowest voltage-to-current (V/I) ratio would be about seven ohms ($7\Omega$), and a short circuit is typically not indicated unless the impedance is less than approximately four ohms ($4\Omega$).

Various embodiments address this issue by measuring the phase difference or angle of the electrosurgical signal. When the impedance between the electrodes is greater than about ten ohms ($10\Omega$), the real component of the total impedance swamps the imaginary component due to the blocking capacitor and there is a relatively low phase angle between the current and the voltage of the current of the electrosurgical signal (e.g., less than about 45°). For example, when the impedance between the electrodes is equal to ten ohms ($10\Omega$), then the phase angle is about 34°. The calculation changes, however, when a short circuit condition exists between the electrodes. In this case, the real component of the impedance drops to zero, and the total impedance is $0-j\omega k$, causing the phase angle between voltage and current to approach 90°. Phase shifts of this magnitude may be detected without the need for precise measurement, for example, by measuring the time between zero crossings for voltage and current of the electrosurgical signal. Because the actual value of the phase shift is not calculated, such a method may be robust regardless of the actual frequency of the electrosurgical signal.

Figure 20:
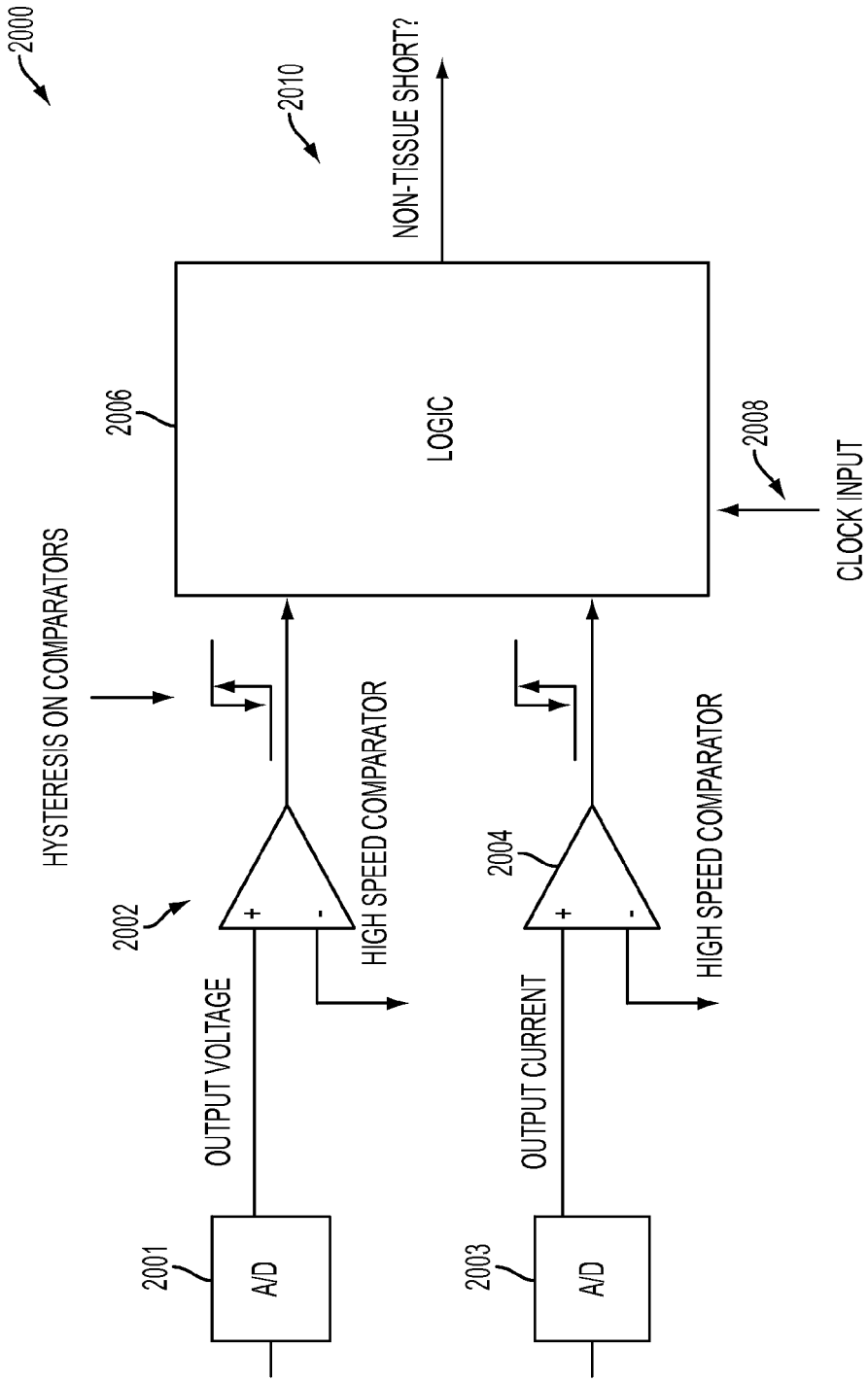
FIG. 20 shows a logical diagram of a circuit for detecting a short circuit based on phase difference.

FIG. 20 shows a logical diagram of a circuit 2000 for detecting a short circuit based on phase difference. The circuit 2000 may be executed by a generator 120, 220 or control circuit 125, 281 thereof. The circuit 2000 may be embodied by distinct components. Alternatively, in some embodiments, some or all of the components of the circuit 2000 may be implemented by a digital signal processor (DSP) or other microprocessor. The Output Voltage and Output Current of the electrosurgical signal may be provided to respective comparators 2002, 2004. For example, the Output Voltage and Output Current signals may be converted from analog to digital at respective A/D converters 2001, 2003. Comparators 2002, 2004 may be configured to detect rising and falling edges of respective Output Voltage and Output Current signals. For example, the comparator 2002 may have its input connected to provide, at a comparator output, indications of the zero crossings, (e.g., both rising and falling) of the voltage of the electrosurgical signal. The comparator 2002 may be configured to compare a scaled voltage signal representing the output current. The output of the comparator 2002 may represent the zero crossings, both rising and falling, of the current of the electrosurgical signal. In some embodiments, the comparators 2002, 2004 may be implemented with hysteresis, as shown in FIG. 20. In this way, the outputs of the comparators 2002, 2004 may be less sensitive to signal bounce and, therefore, less likely to falsely indicate a rising or falling edge.

Outputs of the comparators 2002, 2004 may be provided to implementation logic 2006. The implementation logic 2006 may also receive a clock input 2008. The implementation logic 2006 may be configured to measure the number of clock cycles between corresponding rising and/or falling edges of the Output Voltage and Output Current signals. When this indicates a phase difference of greater than a short threshold (e.g., 45°), the output 2010 of the implementation logic 2006 may indicate a short circuit. When a phase difference of less than the threshold is detected, the output 2010 of the implementation logic 2006 may indicate no short circuit. Because the circuit 2000 need not calculate actual phase differences, it may be implemented with relatively slower and less expensive components. For example, the A/D converters 2001, 2003 may be low-cost, low-speed converters. Also, the implementation logic 2006 may be executed utilizing simple gate logic and/or an inexpensive microprocessor.

In some embodiments, an adaptive short threshold may be used. For example, the generator 102 may utilize different phase different thresholds to indicate short circuits based on other parameters. For example, in some embodiments, the short threshold may vary based on the first derivative of the phase difference. For example, if the phase difference is rapidly increasing, a lower short threshold may be used. This may allow the electrosurgical system 100 to respond to short circuits faster, decreasing the amount of energy that is provided to the patient during the short.

Figure 21:
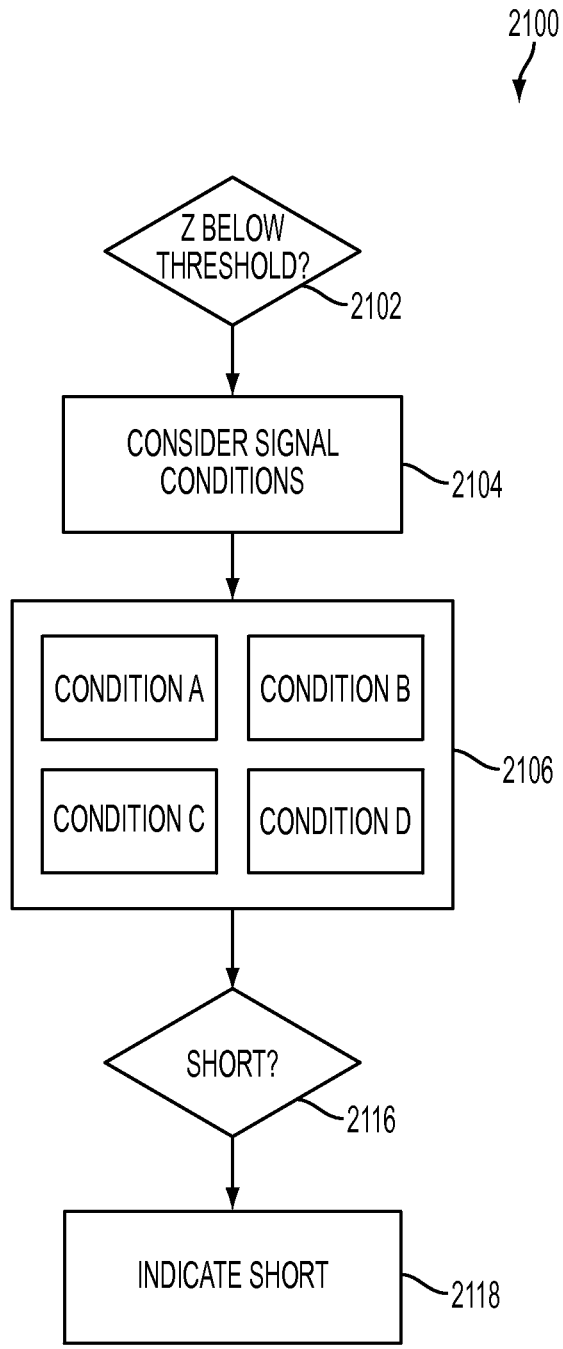
FIG. 21 is a flow chart showing one embodiment of a process flow for detecting a short circuit in an electrosurgical system.

FIG. 21 is a flow chart showing one embodiment of a process flow 2100 for detecting a short circuit in an electrosurgical system. The process flow 2100 may be implemented by any suitable component of an electrosurgical system such as, for example, a generator 120, 220 or control circuit 125, 281 thereof. In various embodiments, the process flow 2100 may be executed during the provision of an electrosurgical signal between the electrodes of the electrosurgical system. For example, the electrosurgical signal may be a pulsed signal, as described herein. At 2102, the electrosurgical system may determine if the impedance between the electrodes has dropped below a threshold impedance. This may be determined in any suitable manner. For example, a drop in tissue impedance may be indirectly sensed by monitoring differences in other electrical parameters (e.g., current, voltage, etc.), averages of various electrical parameters and/or cumulative measures of various electrical parameters over time. In some embodiments, the electrosurgical system may also determine whether the impedance between the electrodes has dropped below the threshold impedance for a threshold amount of time, for example, as described herein above. The decision 2102 may indicate a low tissue impedance event between the electrodes. This may be caused by a short circuit and/or by a low tissue impedance condition exhibited by tissue between the electrodes. Additional actions may be taken to distinguish between these possibilities. For example, if the decision 2102 is determined in the affirmative, the electrosurgical system may consider additional signal conditions at 2104. The additional signal conditions 2106 may be any conditions that tend to indicate the presence or absence of a short circuit. Example conditions A-D are shown in FIG. 21.

In some example embodiments, the conditions 2106 may comprise a change in impedance, an average impedance over time, a change in the average impedance, and an energy delivered between the electrodes. The change in impedance may indicate a short circuit, for example, if it exhibits a sudden drop in impedance. Such a sudden drop may correlate to a conductive staple, clip or other component coming into contact with both electrodes. The average impedance may be utilized, for example, in conjunction with a currently measured impedance. For example, if the currently measured impedance is less than the average impedance by greater than a threshold amount, it may indicate a short circuit. The change in average impedance may also indicate a short circuit. For example, a drop in the average impedance may indicate the presence of a short circuit. The energy and/or power provided between the electrodes may also be used to indicate a short circuit. For example, when a low impedance condition is due to tissue effects, the electrosurgical signal may still provide energy to the tissue. On the other hand, when a low-impedance condition is due to a conductive staple, clip or other object shorting between the electrodes, little energy is delivered. Accordingly, low energy levels may tend to indicate a short circuit. Various permutations of the conditions 2106 may also be considered. For example, conditions 2106 may be considered between adjacent pulses, averaged over multiple pulses, at different positions in a single pulse, etc. Also, in addition to or instead of some or all of the conditions shown, the conditions 2106 may include any suitable combination of changes, averages, or other statistical analysis of the current, voltage, impedance, power and/or energy delivered between the electrodes.

At 2116, the electrosurgical system may determine whether a short circuit is present considering the conditions 2106. The decision at 2116 may be made in any suitable manner using any logical construct. For example, each of the conditions 2106 may be assigned an inference based on the condition's value. Any logical calculation may be utilized to determine whether the totality of the conditions indicate a short circuit. For example, if all of the conditions 2106 indicate a short circuit, then a short circuit may be considered present. In some embodiments, if a majority of the conditions indicate a short circuit, then a short circuit may be considered present. If a short is present at 2116, the electrosurgical system may indicate the short at 2118, for example, as described herein.

Figure 22:
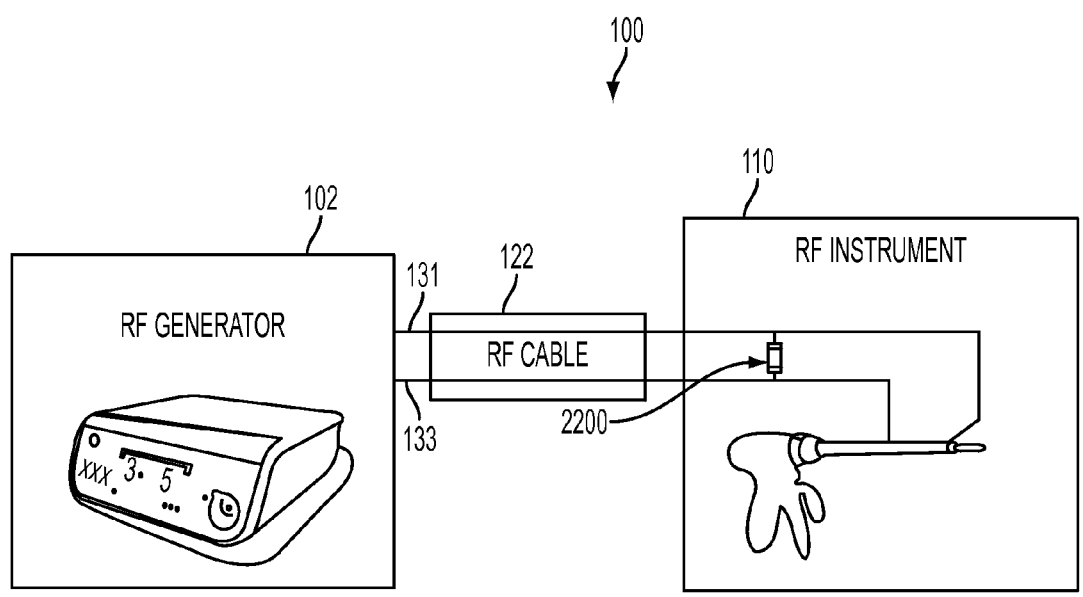
FIG. 22 is a diagram showing one embodiment of the electrosurgical system of FIG. 1 comprising a fuse.

According to various embodiments, the electrosurgical system may utilize a fuse to accurately determine the impedance of various components of the system including, for example, the generator 102, the instrument 110, the cable 122, etc. When a short circuit is present, the impedance between the electrodes in the jaws 164a, 164b may be zero, or very close to zero. The total system impedance, however, will not be zero. Impedance components due to the generator 102, the instrument 110, the cable 122 and, potentially, other system components may still be in place. To accurately measure and compensate for these impedances, the electrosurgical system may utilize a low-current fuse. FIG. 22 is a diagram showing one embodiment of the electrosurgical system 100 comprising a fuse 2200. The fuse 2200 may be physically positioned in the instrument 110 (e.g., in the handle 112 of the instrument 110) in such a position to allow the system to measure enough of the impedance of the cable 122 and internal electrical wiring and connections to accurately portray the intrinsic impedance of the entire electrosurgical system 100 and electrically connected between the supply conductor 131 and the return conductor 133.

Prior to clearing, the fuse 2200 may effectively short the electrodes of the instrument 110, allowing the generator 102 to determine the impedance of the cable 122, generator 102 and instrument 110 portions of the system 100. The measured impedance of the generator 102, cable 122 and instrument 110 may be utilized to set an impedance threshold for determining short circuits. For example, when the total impedance of the system 110 falls to within a threshold value of the sum of the instrument 110 impedance, the cable 122 impedance and the generator 102 impedance, it may indicate a short circuit. The resulting impedance threshold may be used in any suitable manner. For example, the generator 102 may apply the calculated impedance threshold in a straight manner. That is, if the measured impedance between the electrodes is less than the threshold, then a short circuit may be indicated. Also, in some embodiments, the calculated impedance threshold may be utilized as input to another algorithm such as, for example, the process flow 1200, the fuzzy logic algorithm 1300, the process flow 2100, etc.

Figure 23:
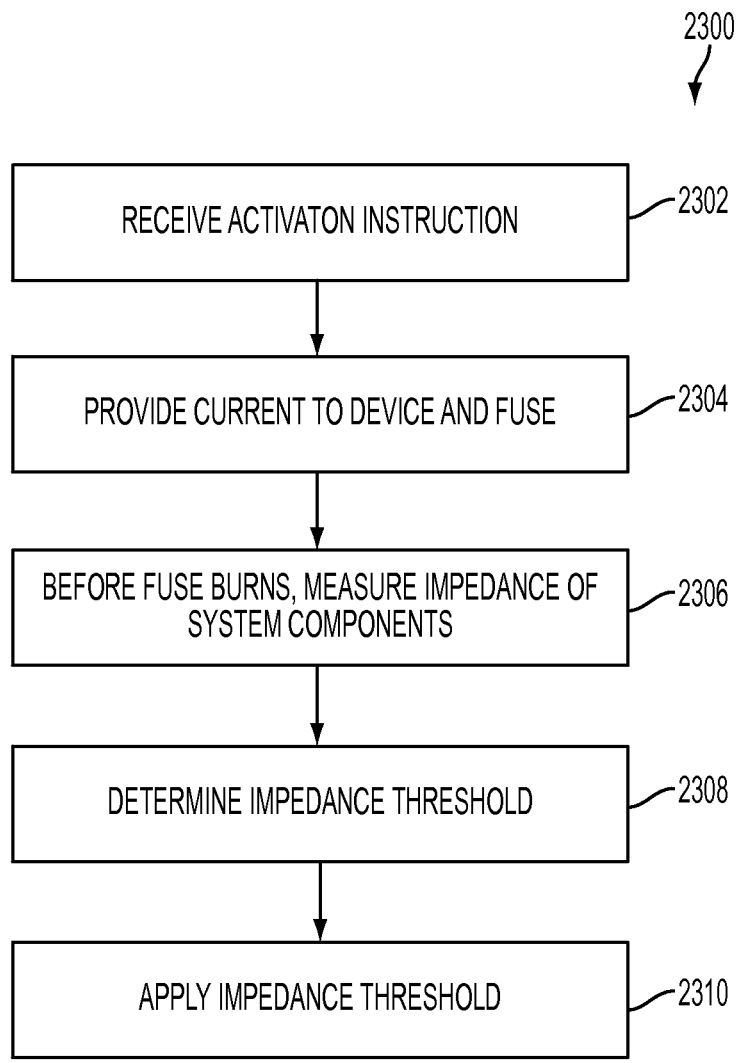
FIG. 23 is a flow chart showing one embodiment of a process flow for utilizing a fuse to generate an impedance threshold.

FIG. 23 is a flow chart showing one embodiment of a process flow 2300 for utilizing a fuse 2200 to generate an impedance threshold. At 2302, the electrosurgical system 100 receives an activation instruction. The activation instruction may be a request (e.g., initiated by the clinician) to provide RF energy to tissue. The instruction may be received, for example, via the button 128, 228. Upon receipt of the activation instruction, the generator 102 may, at 2304, provide a drive signal to the device 110 (and the fuse 2200). The drive signal may be provided at a current that is below a clearing threshold of the fuse 2200. At 2306, the generator 102 may measure the impedance of the generator 102, cable 122 and instrument 110, as described herein. Based on the measured impedances, the generator 102 may determine an impedance threshold at 2308. The impedance threshold may be applied at 2310, for example, as a straight threshold and/or as an input to another algorithm such as, for example, the process flow 1200, the fuzzy logic algorithm 1300, the process flow 2100, etc. Before clinical use, the fuse 2200 may be cleared. For example, the current of the drive signal may be raised above the clearing threshold of the fuse 2200.

In some embodiments, the fuse 2200 may be a single use fuse. Accordingly, the process flow 2300 may be executed once on the first activation of the electrosurgical system 100. Also, in some embodiments, the fuse 2200 is a resettable fuse that may be utilized multiple times. In such cases, the process flow 2300 may be executed each time the electrosurgical system 100 is activated. Between activations, the fuse 2200 may be reset in any suitable manner. For example, the generator 102 may provide a reset signal to the fuse 2200 between activations. Also, in some embodiments, the fuse 2200 may be configured to self-reset upon termination of an electrosurgical signal. Also, it will be appreciated that a fuse may be utilized to measure the impedance of various components of the system 100 in ways other than those described by the process flow 2300. For example, in some embodiments, the detection of the impedances of the various system components may be initiated when the instrument 110 is connected to the generator 102 rather than when the activation instruction is received. Also, in some embodiments, the fuse 2200 may be positioned in the cable 122 instead of in the instrument 110. This may reduce the number of electrical connections made in the instrument 110 itself and may also simplify the cleaning and/or sterilizing of the instrument 110 between uses. Positioning the fuse 2200 in the cable, however, may also prevent the generator 102 from measuring the impedance of the instrument 110 itself, as the fuse 2200, when positioned in the cable 122, may completely short out the instrument 110.

In some embodiments, a fuse 2200 may be utilized to measure the impedance of the instrument 110 and/or cable with the electrodes effectively shorted during the manufacturing and/or testing process. For example, the fuse 2200 may be utilized, as described herein, to measure the impedance during the manufacturing process. An indication of the measured impedance may be stored in the instrument 110 and/or cable 122 utilizing any sort of storage device including, for example, a potentiometer, a ferroelectric random-access memory (FRAM), a dynamic random access memory (DRAM), an electrically erasable programmable read only memory (EPROM), or any other non-volatile storage. The storage device may be positioned in the cable 122, in the instrument 110 or at any other suitable location. The fuse 2200 may be cleared before the manufacturing process is complete. In addition to, or instead of a storage device, the measured impedance and/or threshold may be physically indicated on the device, for example using text, a bar code, etc.

In some embodiments, the fuse 2200 may be omitted. The impedance of the instrument 110, cable 122 and/or other components of the system may be measured by shunting the electrodes of the instrument, for example, during the manufacturing or testing process. While the electrodes are shunted, a drive signal may be provided, as described above with respect to FIG. 23. A short threshold impedance may be found based on the measured system impedance. The measured system impedance and/or the calculated short threshold impedance may be stored with the device, for example, as described above. The shunt may be any conductive material such as, for example, a piece of foil or another metallic conductor. The shunt may be placed in any suitable position. For example, the shunt may be placed directly between the electrodes in the first and second jaws 164a, 164b.

According to various embodiments, an adaptive filter may be utilized to detect a short circuit. The output of an adaptive filter may be determined by a transfer function with a defined structure based on variables that change based on an error signal. The adaptive filter receives two input signals, a desired response signal and an actual output signal. An error is defined as the difference between the desired response signal and the output signal. The error is provided back to the adaptive filter, which based on its transfer function, determines changes to be made to minimize the error signal. An adaptive filter may be implemented by the generator 102 and/or instrument 110 in analog and/or digital form. For example, an adaptive filter may be implemented utilizing appropriate analog components with feedback loops and may be implemented as a complete package on a field-programmable gate array (FPGA). Also, an adaptive filter may be implemented by a digital device such as a digital signal processor or any other suitable processor of the generator 102 or instrument 110.

Figure 24:
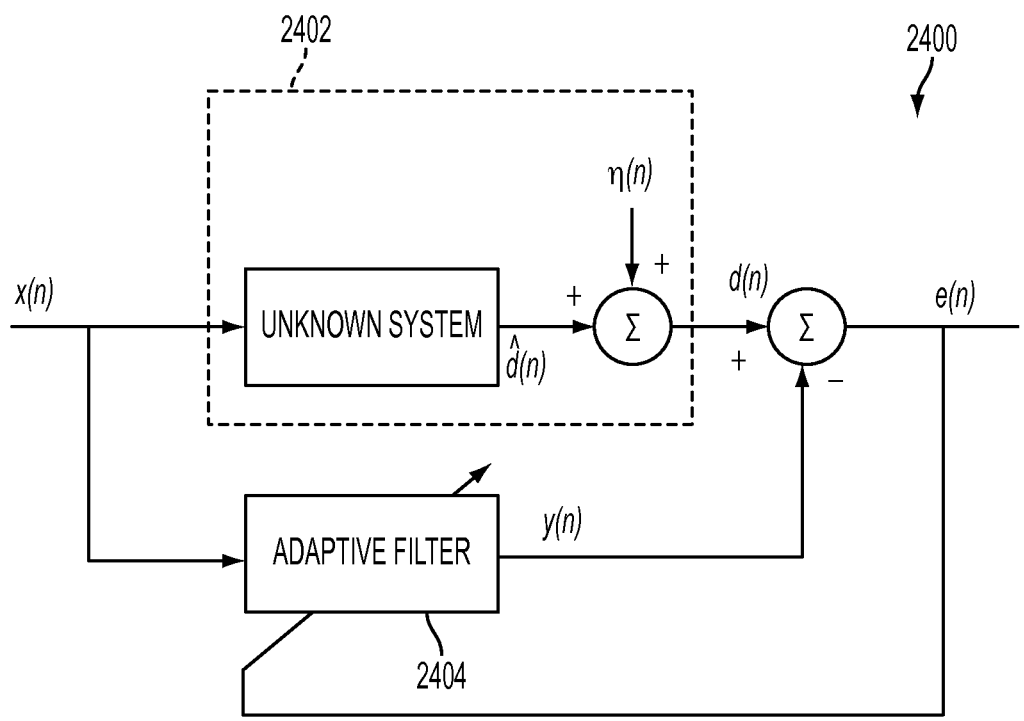
FIG. 24 is a diagram showing one embodiment of an adaptive filter for detecting short circuits.

FIG. 24 is a diagram showing one embodiment of an adaptive filter 2400 for detecting short circuits. The filter 2400 may receive an input signal x(n), where x(n) represents the drive signal of the electrosurgical system 100 as a function of time, n. The unknown system 2402 represents the electrosurgical system 100, with an output of the unknown system 2402 corresponding to the system impedance. The output d(n) may, in some embodiments, be affected by a noise signal n(n). Accordingly, the measured impedance of the electrosurgical system 100, including noise, is represented by d(n). The adaptive filter 2404 may also receive the drive signal x(n). An output y(n) of the adaptive filter 2404 indicates an estimate of the impedance of the system 100. An error signal e(n) represents the difference between the output y(n) of the adaptive filter 2404 and the actual impedance of the electrosurgical system 100. The error signal e(n) is received by the adaptive filter 2404, which adjusts the output y(n) to drive the error signal e(n) towards zero.

In various embodiments, one of the input parameters of the transfer function of the adaptive filter 2404 is an "acceptable level" below the short-circuit threshold that the measured impedance of the system d(n) can reach before a short circuit is indicated. In some embodiments, as the adaptive filter operates, the generator 102 may monitor the value of the acceptable level parameter. If the acceptable parameter level changes too quickly, the generator 102 may determine that a short circuit is present.

It will be appreciated that the transfer function of the adaptive filter 2404 may have any suitable form. For example, in some embodiments, the transfer function of the adaptive filter 2404 utilizes what is known as a method of steepest decent transfer function. A transfer function of this form may minimize changes in the output of the adaptive filter 2404. In various embodiments, this allows for tight bounds for applying energy to tissue and may quickly report a short circuit. In various embodiments, the adaptive filter 2404 may operate in real time or in near or pseudo-real time. For example, the adaptive filter 2404 may be set to operate at a speed matching the speed of data acquisition (e.g., the speed at which the generator 102 samples the drive signal to determine the system impedance). In some embodiments, changes to the adaptive filter 2404 may be made on a cycle-by-cycle basis meaning that affects in one sample or set of data may be corrected for in the next data set. This may allow the generator 102 to minimize the amount of energy provided to the instrument 110 and/or the patient after the creation of a short circuit. In some embodiments, the sampling rate of the generator 102, and therefore the time resolution of the adaptive filter 2404, is on the order of one microsecond.

Figure 25:
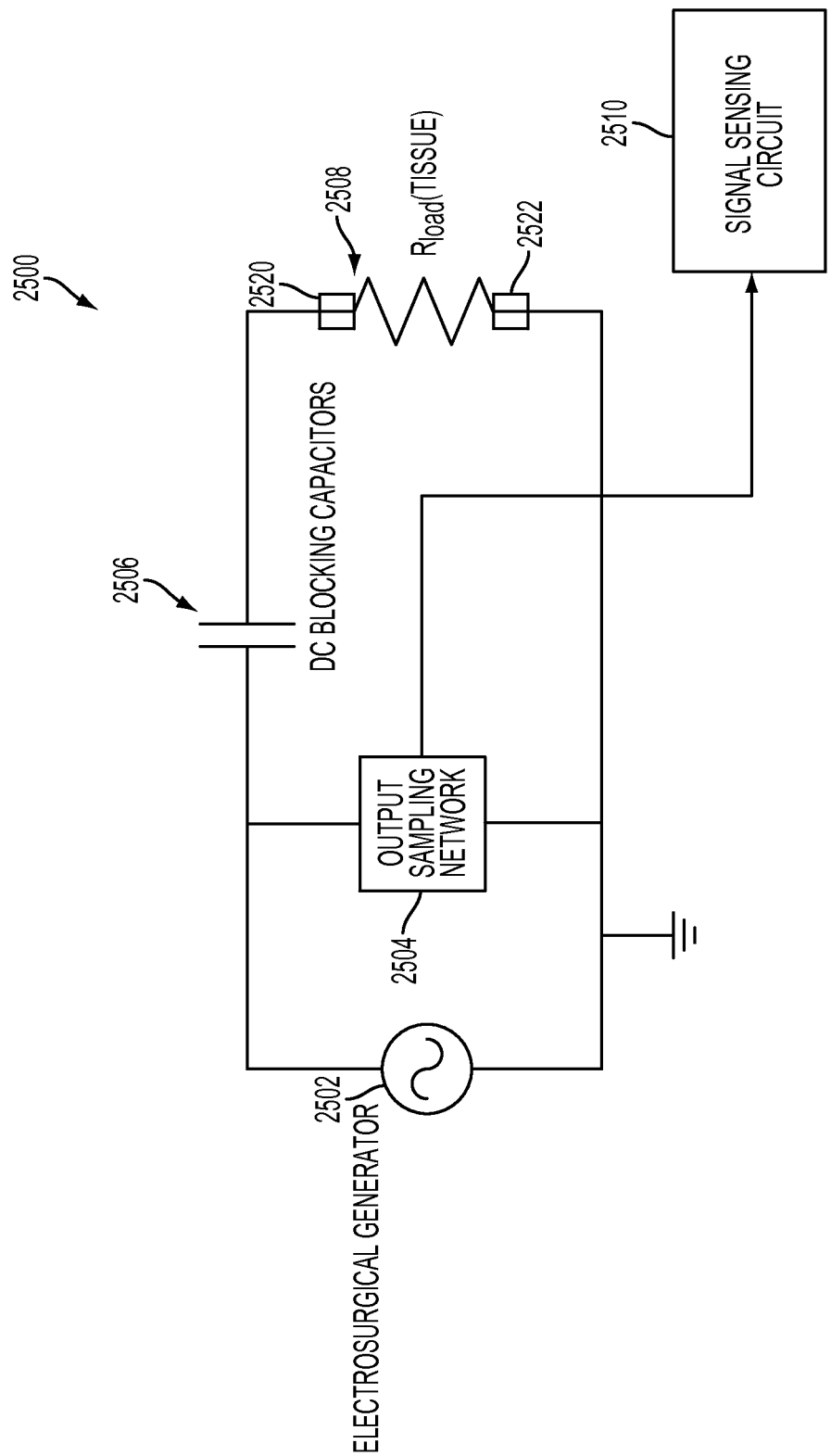
FIG. 25 is a diagram showing one embodiment of an electrosurgical instrument circuit demonstrating tissue impedance management.

According to various embodiments, detection of short circuits may be enhanced by measuring impedance on the patient side of the generator. For example, FIG. 25 is a diagram showing one embodiment of an electrosurgical device circuit 2500 demonstrating tissue impedance management. The circuit 2500 comprises a generator 2502, an output sampling network 2504, direct current (DC) blocking capacitors 2506, electrodes 2520, 2522, and signal sensing circuit 2510. A tissue impedance ($R_{load}$(tissue)) may be present between the electrodes 2520, 2522 when the device is in use. It will be appreciated that the various components of the circuit 2500 may be components of the generator 120, 220 and/or part of the instrument depending on the implementation. The generator 2502 may produce an electrosurgical drive signal, which may be provided to the electrodes 2520, 2522, for example, as described herein. The DC blocking capacitors 2506 may be positioned in series between the generator 2502 and the electrodes 2520, 2522 to prevent unintended DC stimulation of the patient. Accordingly, the circuit 2500 comprises a generator-side portion and a patient-side portion. The DC capacitors 2506 serve to isolate the patient-side portion from DC signals generated (e.g., inadvertently) by the generator-side.

An output sampling network 2504 may be positioned to sample the electrosurgical drive signal and provide an output to the signal sensing circuit 2510. For example, the output sampling network 2504 may comprise a resistive divider network. For example, the output sampling network may step down the voltage of the electrosurgical drive signal to a scale that can be sampled by the signal sensing circuit 2510. The signal sensing circuit may comprise, for example, an analog-to-digital (A/D) converter and any suitable processor or other digital circuit for measuring the provided voltage. From the voltage of the electrosurgical drive signal, for example, as measured through the output sampling network 2504, the tissue impedance 2508 may be derived. In some embodiments, the output sampling network 2504 may be omitted and the signal sensing circuit 2510 may directly receive the electrosurgical drive signal.

Because the output sampling network 2504 and signal sensing circuit 2510 are on the generator-side of the circuit, however, the voltage drop across the network 2504 indicates the impedance of both the load 2508 and the DC blocking capacitors 2506. For example, in some embodiments, the DC blocking capacitors may have a capacitance of fifty (50) nanofarads (nF). At an example drive signal frequency of 330 Hz, this generates a reactance of $1/(j\omega C)$ ohms, in this case $-j10.26$ ohms. It will be appreciated that when the tissue impedance 2508 is low, for example, during a tissue short condition, the reactance of the DC blocking capacitors 2506 may dominate, leading to less accuracy in the impedance measurement made by the signal sensing circuit 2510.

Figure 26:
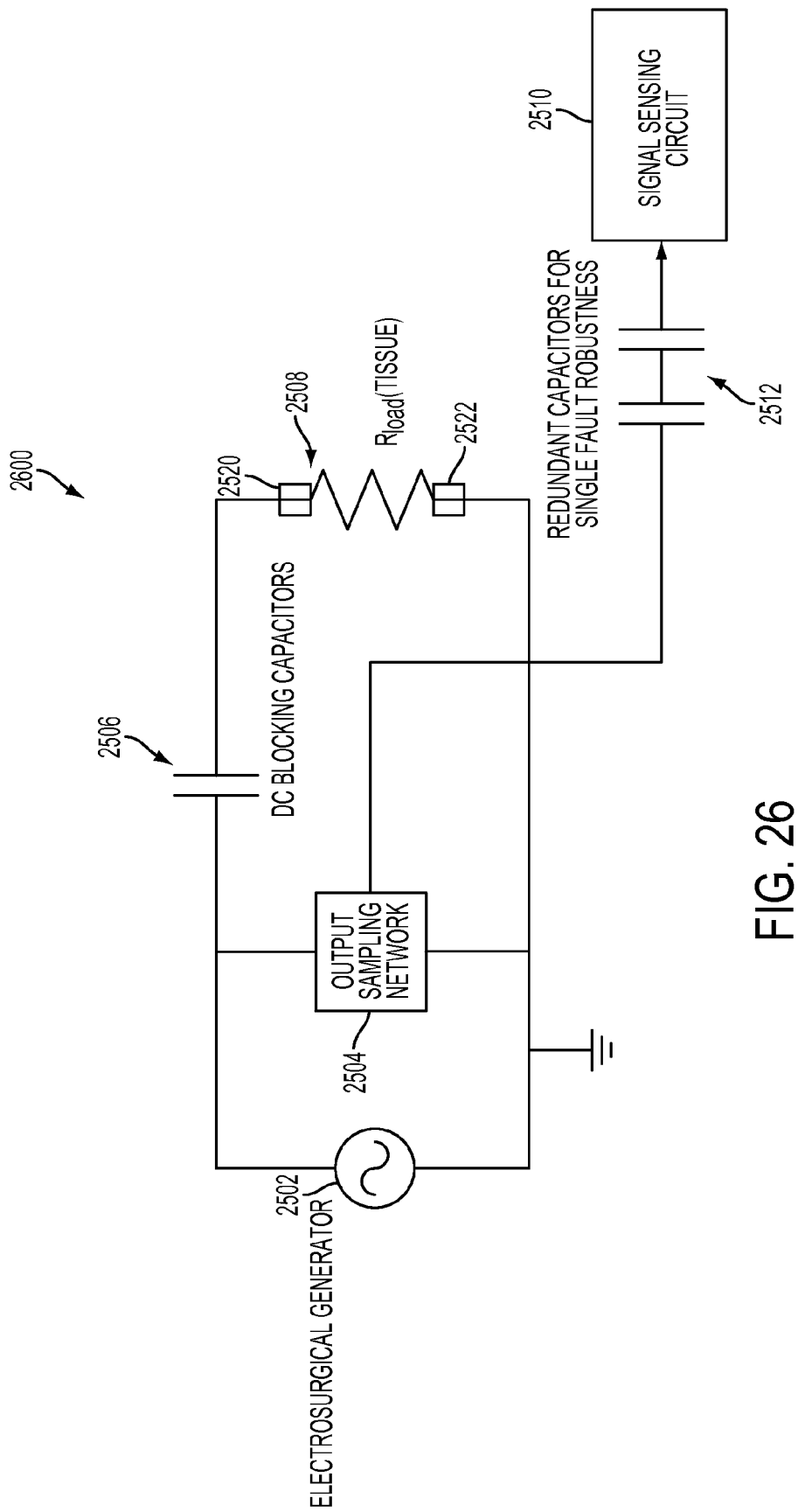
FIG. 26 is a diagram showing one embodiment of an electrosurgical device circuit with the output sampling network positioned on the patient-side of the DC blocking capacitors.

FIG. 26 is a diagram showing one embodiment of an electrosurgical device circuit 2600 with the output sampling network 2504 positioned on the patient-side of the DC blocking capacitors 2506. For example, the output sampling network 2504 may be electrically coupled to the electrode 2520 on the same side of the DC blocking capacitors 2506 as the electrode 2520. In this configuration, the output sampling circuit 2504 directly measures the tissue impedance 2508, thereby reducing distortion due to the DC blocking capacitors 2506. Placing the output sampling circuit 2504 on the patient-side of the DC blocking capacitors 2506, however, may lead to additional blocking capacitors 2512. For example, blocking capacitors 2512 are positioned, as shown, to isolate the signal sensing circuit 2510 from the patient-side. In some embodiments, multiple blocking capacitors 2512 may be used to prevent the passage of DC current to the patient in the event of capacitor failure. In various embodiments, the blocking capacitors 2512 need not have a capacitance as large as that of the DC blocking capacitors 2506. This may be because the signal sensing circuit 2510 may not have a limited ability to generate inadvertent DC signals. For example, in some embodiments, the capacitors 2512 may have a capacitance of 47 nF and/or 294 nF. It will be appreciated that, in some embodiments of the circuits 2500, 2600, the output sampling network 2504 may be omitted and the signal sensing circuit may receive an input direction from the generator 2502, for example, on the generator side of the circuit 2500 and the patient-side of the circuit 2600.

It will be appreciated that the terms "proximal" and "distal" are used throughout the specification with reference to a clinician manipulating one end of an instrument used to treat a patient. The term "proximal" refers to the portion of the instrument closest to the clinician and the term "distal" refers to the portion located furthest from the clinician. It will further be appreciated that for conciseness and clarity, spatial terms such as "vertical," "horizontal," "up," or "down" may be used herein with respect to the illustrated embodiments. However, surgical instruments may be used in many orientations and positions, and these terms are not intended to be limiting or absolute.

Various embodiments of surgical instruments and robotic surgical systems are described herein. It will be understood by those skilled in the art that the various embodiments described herein may be used with the described surgical instruments and robotic surgical systems. The descriptions are provided for example only, and those skilled in the art will understand that the disclosed embodiments are not limited to only the devices disclosed herein, but may be used with any compatible surgical instrument or robotic surgical system.

Reference throughout the specification to "various embodiments," "some embodiments," "one example embodiment," or "an embodiment" means that a particular feature, structure, or characteristic described in connection with the embodiment is included in at least one example embodiment. Thus, appearances of the phrases "in various embodiments," "in some embodiments," "in one example embodiment," or "in an embodiment" in places throughout the specification are not necessarily all referring to the same embodiment. Furthermore, the particular features, structures, or characteristics illustrated or described in connection with one example embodiment may be combined, in whole or in part, with features, structures, or characteristics of one or more other embodiments without limitation.

While various embodiments herein have been illustrated by description of several embodiments and while the illustrative embodiments have been described in considerable detail, it is not the intention of the applicant to restrict or in any way limit the scope of the appended claims to such detail. Additional advantages and modifications may readily appear to those skilled in the art. For example, it is generally accepted that endoscopic procedures are more common than laparoscopic procedures. Accordingly, the present invention has been discussed in terms of endoscopic procedures and apparatus. However, use herein of terms such as "endoscopic", should not be construed to limit the present invention to an instrument for use only in conjunction with an endoscopic tube (e.g., trocar). On the contrary, it is believed that the present invention may find use in any procedure where access is limited to a small incision, including but not limited to laparoscopic procedures, as well as open procedures.

It is to be understood that at least some of the figures and descriptions herein have been simplified to illustrate elements that are relevant for a clear understanding of the disclosure, while eliminating, for purposes of clarity, other elements. Those of ordinary skill in the art will recognize, however, that these and other elements may be desirable. However, because such elements are well known in the art, and because they do not facilitate a better understanding of the disclosure, a discussion of such elements is not provided herein.

While several embodiments have been described, it should be apparent, however, that various modifications, alterations and adaptations to those embodiments may occur to persons skilled in the art with the attainment of some or all of the advantages of the disclosure. For example, according to various embodiments, a single component may be replaced by multiple components, and multiple components may be replaced by a single component, to perform a given function or functions. This application is therefore intended to cover all such modifications, alterations and adaptations without departing from the scope and spirit of the disclosure as defined by the appended claims.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Various aspects of the subject matter described herein are set out in the following numbered clauses:

1. An electrosurgical system for providing an electrosurgical signal to a patient, the system comprising:
   a control circuit, wherein the control circuit is programmed to:
   provide the electrosurgical signal to first and second electrodes, wherein the electrosurgical signal defines a plurality of pulses;
   receive a first reading of an impedance between the first and second electrodes, wherein the first reading is taken at a first point of a first pulse of the electrosurgical signal;
   receive a second reading of the impedance between the first and second electrodes, wherein the second reading is taken at a first point of a second pulse of the electrosurgical signal, wherein the first point of the first pulse and the first point of the second pulse are at equivalent positions within the first and second pulses;
   based on a comparison of the first reading and the second reading, determine that a short circuit is present between the first and second electrodes;
   generate a signal indicating the short circuit between the first and second electrodes.

2. The electrosurgical system of clause 1, wherein the first pulse and the second pulse are adjacent pulses within the electrosurgical signal.

3. The electrosurgical system of clause 1, wherein the control circuit is further programmed to:
   receive a third reading of the impedance between the first and second electrodes at a second point of the first pulse;
   receive a fourth reading of the impedance between the first and second electrodes at a second point of the second pulse, wherein the second point of the first pulse and the second point of the second pulse are at equivalent positions within the first and second pulses, and wherein the determining that the short circuit is present between the first and second electrodes is also based on the third reading and the fourth reading.

4. The electrosurgical system of clause 1, wherein the control circuit is programmed to, prior to receiving the first and second readings, determine that the impedance between the first and second electrodes has fallen below a threshold impedance for a threshold amount of time.

5. The electrosurgical system of clause 1, wherein the electrosurgical signal is a measurement electrosurgical signal, and wherein the control circuit is further programmed to:
provide a first electrosurgical signal to the plurality of electrodes;
receive an indication of the impedance between the first and second electrodes during provision of the first electrosurgical signal; and
provide the measurement electrosurgical signal when the tissue impedance during provision of the standard electrosurgical signal drops below a threshold impedance for a threshold amount of time.

6. The electrosurgical system of clause 1, wherein the control circuit is further programmed to:
receive a third reading of the impedance between the first and second electrodes taken at a first point of a third pulse of the electrosurgical signal;
receive a fourth reading of the impedance between the first and second electrodes taken a first point of a fourth pulse of the electrosurgical signal, wherein the first point of the third pulse and the first point of the fourth pulse are at positions within the third and fourth pulses equivalent to the positions of the first point of the first pulse and the first point of the second pulse, and wherein the determining that the short circuit is present between the first and second electrodes is also based on a comparison of the first, second, third and fourth tissue impedances.

7. The electrosurgical system of clause 6, wherein determining that the short circuit is present between the first and second electrodes comprises:
counting a first number of tissue impedances selected from the first, second, third and fourth tissue impedances that are within a threshold impedance value of one another; and
when the first number of tissue impedance exceeds a threshold value, indicate a short circuit between the first and second electrodes.

8. An electrosurgical system for providing an electrosurgical signal to a patient, the system comprising:
a control circuit comprising, wherein the control circuit is programmed to:
provide the electrosurgical signal to first and second electrodes, wherein the electrosurgical signal is described by a voltage and a current;
measure a phase difference between the voltage of the electrosurgical signal and the current of the electrosurgical signal;
when the phase difference between the voltage of the electrosurgical signal and the current of the electrosurgical signal exceed a threshold phase difference, determine that a short circuit is present between the first and second electrodes; and
generate a signal indicating the short circuit between the first and second electrodes.

9. The electrosurgical system of clause 8, wherein the threshold phase difference is less than 45 degrees.

10. The electrosurgical system of clause 8, wherein the control circuit is further programmed to generate the threshold phase difference based on a rate of change of the phase difference between the voltage of the electrosurgical signal and the current of the electrosurgical signal.

11. The electrosurgical system of clause 8, wherein the control circuit comprises:
a voltage comparator connected to provide a voltage comparator output indicative of the voltage of the electrosurgical signal;
a current comparator connected to provide a current comparator output indicative of the current of the electrosurgical signal;
a logic circuit configured to receive the voltage comparator output and the current comparator output and provide a logic circuit output, wherein the logic circuit output is asserted when the phase difference between the voltage of the electrosurgical signal and the current of the electrosurgical signal exceeds the threshold phase difference and is un-asserted when the phase difference between the voltage of the electrosurgical signal and the current of the electrosurgical signal does not exceed the threshold phase difference.

12. The electrosurgical system of clause 11, wherein the voltage comparator and the current comparator are configured to provide a hysteresis function on the voltage comparator output and the current comparator output.

13. The electrosurgical system of clause 11, wherein the control circuit further comprises a clock, and wherein the logic circuit output is asserted when a number of clock cycles between a rising edge of the voltage comparator output and a rising edge of the current comparator output exceeds a threshold number.

14. The electrosurgical system of clause 11, wherein the control circuit further comprises a clock, and wherein the logic circuit output is asserted when a number of clock cycles between a rising edge of the voltage comparator output and a falling edge of the current comparator output exceeds a threshold number.

15. An electrosurgical system for providing an electrosurgical signal to a patient, the system comprising:
a control circuit, wherein the control circuit is programmed to:
provide the electrosurgical signal to first and second electrodes, wherein the electrosurgical signal defines a plurality of pulses;
when an impedance between the first and second electrodes is less than an impedance threshold value, determine whether a short circuit is present between the first and second electrodes, wherein the determining comprises comparing an energy delivered between the first and second electrodes to an energy threshold value; and
when the energy delivered between the first and second electrodes is less than the threshold value, generate a signal indicating the short circuit between the first and second electrodes.

16. The electrosurgical system of clause 15, wherein the determining whether the short circuit is present between the first and second electrodes further comprises considering a change in the impedance between the first and second electrodes.

17. The electrosurgical system of clause 15, wherein the determining whether the short circuit is present between the first and second electrodes further comprises considering an average impedance between the first and second electrodes over a first time period.

18. The electrosurgical system of clause 15, wherein the determining whether the short circuit is present between the first and second electrodes further comprises considering a change in an average impedance between the first and second electrodes.

19. An electrosurgical system for providing an electrosurgical signal to a patient, the system comprising:
a control circuit, wherein the control circuit is programmed to:
provide the electrosurgical signal to first and second electrodes;
monitor an impedance between the first and second electrodes during the provision of the electrosurgical signal;
apply at least one cut-off rule to the impedance to indicate a short circuit, wherein the rule indicates a non-short condition between the first and second electrodes when the impedance meets a first set of conditions;
indicate the non-short condition; and
after indicating the non-short condition, apply at least one intermediate rule to the impedance, wherein the intermediate rule indicates a non-short condition between the first and second electrodes when the impedance meets a second set of conditions, wherein the second set of conditions is less indicative of a non-short condition than the first set of conditions.

20. The electrosurgical system of clause 19, wherein the at least one cut-off rule indicates a short circuit when the impedance between the first and second electrodes at a first point of a first pulse is within a first threshold of the impedance between the first and second electrodes at the first point of a second pulse, and wherein the at least one intermediate rule indicates a short circuit when the impedance between the first and second electrodes at the first point of a third pulse is within a second threshold of the impedance between the first and second electrodes at the first point of a fourth pulse, wherein the second threshold is greater than the first.

21. The electrosurgical system of clause 19, wherein the at least one cut-off rule indicates a short circuit when the impedance between the first and second electrodes is less than a first threshold impedance for a first threshold time, wherein the at least one intermediate rule indicates a short circuit when the impedance between the first and second electrodes is less than a second threshold impedance for a second threshold time, wherein the first threshold impedance is less than the second threshold impedance.

22. The electrosurgical system of clause 22, wherein the first threshold time is longer than the second threshold time.

23. An electrosurgical system for providing an electrosurgical signal to a patient, the system comprising:
a control circuit, wherein the control circuit is programmed to:
provide the electrosurgical signal to first and second electrodes;
monitor an impedance between the first and second electrodes during the provision of the electrosurgical signal;
generate a plurality of descriptors of the impedance;
apply a trainable model wherein the descriptors of the impedance are inputs to the trainable model, and wherein the output of the trainable model is an indication of the presence or absence of a short circuit.

24. The electrosurgical system of clause 23, wherein the trainable model is a neural network.

25. The electrosurgical system of clause 24, wherein the descriptors of the impedance comprise at least one value selected from the group consisting of: a value for the impedance at a first position of a pulse; an average of the impedance across a pulse; an average of the impedance at the first position across a plurality of pulses, and a condition indicating an equality between the impedance at the first point of a first pulse and the first point of a second pulse.

26. The electrosurgical system of clause 24, wherein the neural network is a neuro-fuzzy network.

27. An electrosurgical system for providing an electrosurgical signal to a patient, the system comprising:
an electrosurgical instrument comprising an end effector, wherein the end effector comprises a first electrode and a second electrode;
an electrosurgical generator coupled to the electrosurgical instrument via a cable;
a fuse electrically connected between the first and second electrodes; and
a control circuit, wherein the control circuit is programmed to:
provide an electrosurgical signal to the electrosurgical instrument at a current below a clearing threshold of the fuse;
based on at least one property of the electrosurgical signal, determine an impedance of at least one of the electrosurgical generator, the electrosurgical instrument, and the cable; and
determine a short circuit impedance threshold considering the impedance of at least one of the electrosurgical generator, the electrosurgical instrument, and the cable.

28. The electrosurgical system of clause 27, wherein the control circuit is further programmed to provide the electrosurgical signal in response to an activation instruction.

29. The electrosurgical system of clause 28, wherein the fuse is a single use fuse.

30. The electrosurgical system of clause 28, wherein the fuse is a resettable fuse, and wherein the control circuit is further configured to:
receive a second activation instruction;
in response to the second activation instruction, provide a second electrosurgical signal to the electrosurgical instrument at a current below a clearing threshold of the fuse;
based on at least one property of the second electrosurgical signal, determine an impedance of at least one of the electrosurgical generator, the electrosurgical instrument, and the cable; and
determine a second short circuit impedance threshold considering the impedance of at least one of the electrosurgical generator, the electrosurgical instrument, and the cable.

31. A method of configuring an electrosurgical system for providing an electrosurgical signal to a patient, the electrosurgical instrument comprising first and second electrodes, the method comprising:
creating an electrical short between the first and second electrodes;
while the electrical short is present between the first and second electrodes, providing a drive signal to the first and second electrodes;
measuring an impedance of the surgical system based on the drive signal; and
recording an indication of the impedance of the surgical system at the surgical system.

32. The method of clause 31, wherein creating the electrical short comprises providing a fuse creating an electrical connection between the first and second electrodes, wherein the method further comprises, after measuring the impedance of the surgical system, clearing the fuse.

33. The method of clause 31, wherein creating the electrical short comprises providing a shunt between the first electrode and the second electrode.

34. An electrosurgical system for providing an electrosurgical signal to a patient, the system comprising:
an electrosurgical instrument comprising an end effector, wherein the end effector comprises a first electrode and a second electrode;
an electrosurgical generator coupled to the electrosurgical instrument via a cable; and
a control circuit, wherein the control circuit is programmed to:
implement an adaptive filter, wherein a first input of the adaptive filter is a drive signal of the electrosurgical system, an output of the adaptive filter is an estimate of the impedance of the electrosurgical system, and a second input of the adaptive filter is an error signal between the estimate of the impedance of the electrosurgical system and a measured impedance of the electrosurgical system, and wherein a transfer function of the adaptive filter comprises an input variable representing an acceptable level below a short-circuit threshold that the measured impedance of the electrosurgical system may reach before a short circuit is indicated; and
when a change in the input variable exceeds a threshold, indicate a short circuit.

35. An electrosurgical system for providing an electrosurgical signal to a patient, the system comprising:
an electrosurgical instrument comprising an end effector, wherein the end effector comprises a first electrode and a second electrode;
an electrosurgical generator electrically coupled to the first and second electrodes to provide an electrosurgical drive signal to the first and second electrodes, wherein the electrosurgical generator comprises:
at least one direct current (DC) blocking capacitor positioned in series between the generator and the first electrode; and
a signal conditioning circuit positioned to receive a signal indicative of a voltage potential between the at least one DC blocking capacitor and the first electrode, wherein the signal conditioning circuit is electrically coupled to the first electrode on the same side of the at least one DC blocking capacitor as the first electrode; and
a second at least one DC blocking capacitor positioned in series between the first electrode and the signal conditioning circuit.

36. The electrosurgical system of clause 35, further comprising an output sampling network electrically coupled between the first electrode and the signal conditioning circuit.

37. The electrosurgical system of clause 35, wherein the output sampling circuit comprises a resistive divider network configured to step down a voltage of the electrosurgical drive signal.

38. The electrosurgical system of clause 35, wherein the electrosurgical system is a monopolar system and the second electrode is a return electrode configured to be electrically coupled to a patient.

What is claimed is:

1. An electrosurgical system for providing an electrosurgical signal to a patient, the system comprising:
a control circuit, wherein the control circuit is programmed to:
provide the electrosurgical signal to first and second electrodes, wherein the electrosurgical signal defines a plurality of pulses;
receive a first reading of an impedance between the first and second electrodes, wherein the first reading is taken at a first point of a first pulse of the electrosurgical signal;
receive a second reading of the impedance between the first and second electrodes, wherein the second reading is taken at a first point of a second pulse of the electrosurgical signal, wherein the first point of the first pulse and the first point of the second pulse are at equivalent positions within the first and second pulses;
based on comparing the first reading with the second reading, determine that a short circuit is present between the first and second electrodes, wherein comparing the first reading with the second reading comprises computing a difference in impedance between the first reading and the second reading, and the determination that the short circuit is present between the first and second electrodes is based further on determining that a magnitude of the difference is less than a predetermined impedance threshold value;
generate a signal indicating the short circuit between the first and second electrodes.

2. The electrosurgical system of claim 1, wherein the first pulse and the second pulse are adjacent pulses within the electrosurgical signal.

3. The electrosurgical system of claim 1, wherein the control circuit is further programmed to:
receive a third reading of the impedance between the first and second electrodes at a second point of the first pulse;
receive a fourth reading of the impedance between the first and second electrodes at a second point of the second pulse, wherein the second point of the first pulse and the second point of the second pulse are at equivalent positions within the first and second pulses, and wherein the determination that the short circuit is present between the first and second electrodes is also based on the third reading and the fourth reading.

4. The electrosurgical system of claim 3, wherein the control circuit is further programmed to:
compute a first average of the first and third readings and a second average of the second and fourth readings, and
compare the first average with the second average by computing a difference between the first average and the second average,
wherein the determination that the short circuit is present between the first and second electrodes is further based on determining that the difference between the first average and the second average is less than the predetermined impedance threshold value.

5. The electrosurgical system of claim 1, wherein the control circuit is programmed to, prior to receiving the first and second readings, determine that the impedance between the first and second electrodes has fallen below a threshold impedance for a threshold amount of time.

6. The electrosurgical system of claim 1, wherein the electrosurgical signal is a measurement electrosurgical signal, and wherein the control circuit is further programmed to:
provide a first electrosurgical signal to the first and second electrodes;
receive an indication of the impedance between the first and second electrodes during the provision of the first electrosurgical signal; and provide the measurement electrosurgical signal when the impedance between the first and second electrodes during the provision of the first electrosurgical signal drops below a threshold impedance for a threshold amount of time.

7. The electrosurgical system of claim 1, wherein the control circuit is further programmed to:
  receive a third reading of the impedance between the first and second electrodes taken at a first point of a third pulse of the electrosurgical signal;
  receive a fourth reading of the impedance between the first and second electrodes taken at a first point of a fourth pulse of the electrosurgical signal, wherein the first point of the third pulse and the first point of the fourth pulse are at positions within the third and fourth pulses equivalent to the positions of the first point of the first pulse and the first point of the second pulse, and wherein the determination that the short circuit is present between the first and second electrodes is also based on a comparison of the first, second, third and fourth readings.

8. The electrosurgical system of claim 7, wherein the determination that the short circuit is present between the first and second electrodes comprises:
  counting a first number of tissue impedances selected from the first, second, third and fourth readings that are within a threshold impedance value of one another; and
  when the first number of tissue impedances exceeds a threshold value, indicate a short circuit between the first and second electrodes.

9. The electrosurgical system of claim 1, wherein the control circuit is further programmed to terminate the electrosurgical system in responsive to the determination that the short circuit is present.

* * * * *